US009260713B2

(12) United States Patent
Wigley et al.

(10) Patent No.: US 9,260,713 B2
(45) Date of Patent: *Feb. 16, 2016

(54) ACCELERATED DIRECTED EVOLUTION OF MICROBIAL CONSORTIA FOR THE DEVELOPMENT OF DESIRABLE PLANT PHENOTYPIC TRAITS

(71) Applicant: BioDiscovery New Zealand Limited, Parnell (NZ)

(72) Inventors: Peter Wigley, Parnell (NZ); Caroline George, Parnell (NZ); Susan Turner, Parnell (NZ)

(73) Assignee: BIODISCOVERY NEW ZEALAND LIMITED, Parnell (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 14/835,867

(22) Filed: Aug. 26, 2015

(65) Prior Publication Data

US 2015/0368637 A1    Dec. 24, 2015

Related U.S. Application Data

(63) Continuation of application No. 14/218,920, filed on Mar. 18, 2014, now Pat. No. 9,150,851, which is a continuation-in-part of application No. PCT/NZ2013/000171, filed on Sep. 19, 2013.

(30) Foreign Application Priority Data

Sep. 19, 2012   (NZ) ........................................ 602532

(51) Int. Cl.
| | | |
|---|---|---|
| *C40B 30/06* | (2006.01) | |
| *C12N 1/20* | (2006.01) | |
| *C12N 15/10* | (2006.01) | |

(52) U.S. Cl.
CPC .................................. *C12N 15/1058* (2013.01)

(58) Field of Classification Search
None
See application file for complete search history.

(56) References Cited

U.S. PATENT DOCUMENTS

| | | | |
|---|---|---|---|
| 4,647,533 | A | 3/1987 | Weller et al. |
| 5,157,207 | A | 10/1992 | Carlson et al. |
| 5,415,672 | A | 5/1995 | Fahey et al. |
| 5,997,269 | A | 12/1999 | Feitelson |
| 7,232,565 | B2 | 6/2007 | Henson et al. |
| 7,786,344 | B2 | 8/2010 | Kock et al. |
| 9,113,636 | B2 | 8/2015 | Von Maltzahn et al. |
| 2003/0228679 | A1 | 12/2003 | Smith |
| 2014/0082770 | A1 | 3/2014 | Wigley et al. |
| 2014/0109249 | A1 | 4/2014 | Turner et al. |
| 2014/0115731 | A1 | 4/2014 | Turner et al. |
| 2015/0080261 | A1 | 3/2015 | Wigley et al. |
| 2015/0150161 | A1 | 5/2015 | Spangenberg et al. |
| 2015/0156982 | A1 | 6/2015 | Spangenberg et al. |
| 2015/0191720 | A1 | 7/2015 | Beilinson et al. |
| 2015/0218568 | A1 | 8/2015 | Jones et al. |
| 2015/0250116 | A1 | 9/2015 | Wigley et al. |

FOREIGN PATENT DOCUMENTS

| | | |
|---|---|---|
| NZ | 588048 | 3/2012 |
| WO | WO 2012/125050 A1 | 9/2012 |
| WO | WO 2013/177615 A1 | 12/2013 |
| WO | WO 2013/177616 A1 | 12/2013 |
| WO | WO 2014/046553 A1 | 3/2014 |
| WO | WO 2014/210372 A1 | 12/2014 |
| WO | WO 2015/035099 A1 | 3/2015 |
| WO | WO 2015/100432 A2 | 7/2015 |
| WO | WO 2015/105993 A1 | 7/2015 |
| WO | WO 2015/116838 A1 | 8/2015 |
| WO | WO 2015/142185 A1 | 9/2015 |

OTHER PUBLICATIONS

"Directed Evolution" from Wikipedia, the free encyclopedia, http://en.wikiQedia.org/wiki/Directed evolution, accessed Mar. 5, 2012, 2 pages.
Allen, O.N. and Allen, E.K., "The Leguminosae. A Source Book of Characteristics, Uses, and Nodulation", Macmillan Publishers Ltd. (Scientific and Medical Division), London and Basingstoke, UK, ISBN 0-333-32221-5, pp. xvi-xvii (1981).
Bacon, C.W., "Isolation and culture of endophytic bacteria." In: Hurst et al (Eds) *Manual of Environmental Microbiology*, ASM Press, Washington, DC, Chapter 45, pp. 413-421 (1997).
Chi, F. et al., "Ascending migration of endophytic rhizobia, from roots to leaves, inside rice plants and assessment of benefits to rice growth physiology", *Applied and Environmental Microbiology*, 71(11):7271-7278 (2005).
Colby, R.S., "Calculating Synergistic and Antagonistic Responses of Herbicide Combinations", *Weeds*, 15(1):20-22 (1967).
Cook, R. James, "A customized approach to biological control of wheat root diseases", *NATO ASI Series a Life Sciences; Biological Control of Plant Diseases: Progress and Challenges for the Future*, Plenum Press, pp. 211-222 (1992).
Eckford, R. et al., "Free-living heterotrophic bacteria isolated from fuel-contaminated Antarctic soils", *Applied and Environmental Microbiology*, 68(10):5181-5185 (2002).
Egamberdieva and Kucharova, "Selection for root colonizing bacteria stimulating wheat growth in saline soils", *Biol Fertil Soils*, 45: 563-571 (2009).
Elo, S. et al., "Humus bacteria of Norway spruce stands: plant growth promoting properties and birch, red fescue and alder colonizing capacity", *Microbiology Ecology*, 31:143-152 (2000).
Fahraeus, G., "The infection of clover root hairs by nodule bacteria studied by a simple glass slide technique", *J. Gen Microbiol.*, 16:374-381 (1957).
Forum for Nuclear Cooperation in Asia (FNCA), Biofertilizer Project Group, Biofertilizer Manual. Tokyo: Japan Atomic Industrial Forum (JAIF), 138 pages. (2006).

(Continued)

*Primary Examiner* — Kade Ariani
(74) *Attorney, Agent, or Firm* — Cooley LLP

(57) ABSTRACT

The disclosure relates to methods for the screening, identification, and/or application of one or more microorganisms of use in imparting one or more beneficial properties to one or more plants.

30 Claims, 18 Drawing Sheets

(56) References Cited

OTHER PUBLICATIONS

Gangwar, M. and Kaur, G., "Isolation and characterization of endophytic bacteria from endorhizosphere of sugarcane and ryegrass", *The Internet Journal of Microbiology*, 7(1):1-7 (2008).
Gordon, J.C. and Wheeler, C.T., "Biological Nitrogen Fixation in Forest Ecosystems: Foundations and Applications", Martinus Nijhoff/ Dr W. Junk Publishers, The Hague, pp. 102-105, ISBN 90-247-2849-5 (1983).
Gyaneshwar, P. et al., "Herbaspirillum colonization increases growth and nitrogen accumulation in aluminum-tolerant rice varities", *New Phytologist*, 154:131-145 (2002).
Infantino, A. et al., "Screening techniques and sources of resistance to root diseases in cool season food legumes", *Euphytica*, 147: 201-221 (2006).
Jetiyanon, K et al., "Film coating of seeds with Bacillus cereus RS87 spores for early plant growth enhancement", *Canadian Journal of Microbiology*, 54(10):861-867 (2008).
Ji, X et al., "Colonization of Morus alba L. by the plant-growth-promoting and antagonistic bacterium Burkholderia cepacia strain Lu10-1", *BMC Microbiology*, 10:243 (2010).
Jiangen, L. et al., "Study on Isolation and Screening of Plant-growth Promoting Rhizobacteria and its Biocontrol Action to Soil-borne Diseases of Cucumber", *Chinese Agricultural Science Bulletin*, vol. 23, No. 12, and English translation (2007).
Johnsen, A.R. et al., "Strong Impact on the Polycyclic Aromatic Hydrocarbon (PAH)-Degrading Community of a PAH-Polluted Soil but Marginal Effect on PAH Degradation when Priming with Bioremediated Soil Dominated by Mycobacteria", *Applied and Environmental Microbiology*, 73(5):1474-1480 (2007).
Kamilova, F. et al., "Enrichment for enhanced competitive plant root tip colonizers selects for a new class of biocontrol bacteria", *Environmental Microbiology*, 7(11):1809-1817 (2005).
Kim, Yeon-Ju et al., "*Microbacterium ginsengiterrae* sp. nov., a β-glucosidase-producing bacterium isolated from soil of a ginseng field", *International Journal of Systematic and Evolutionary Microbiology*, 60(12):2808-2812 (2010).
Kirchhof, G. et al., "*Herbaspirillum frisingense* sp. nov., a new nitrogen-fixing bacterial species that occurs in C4-fibre plants", *International Journal of Systematic and Evolutionary Microbiology*, 51(1):157-168 (2001).
"Koch's Postulates", Wikipedia, retrived from the Internet on Sep. 17, 2014, http://en.wikipedia.org/wiki/Koch's_postulates.
Kuiper, I. et al., "Selection of a plant-bacterium pair as a novel tool for rhizostimulation of polycyclic aromatic hydrocarbon-degrading bacteria", *Molecular Plant—Microbe Interactions*, American Pathological Society, USA, 14(10):1197-1205 (2001).
Lee, D.W. and Lee, S.D. "*Aeromicrobium ponti* sp. nov., isolated from seawater", International Journal of Systematic and Evolutionary Microbiology, 58:987-991 (2008).
Martani, E. et al., "Isolation and Selection of Rhizobium Tolerant to Peticides and Aluminium from Acid Soils in Indonesia", *Journal of Tropical Soils*, 16(1):47-54 (2011).
Mavingui et al., "Generation of *Rhizobium* strains with improved symbiotic properties by random DNA amplification (RDA)", *Nature Biotechnology*, 15: 564-569 (1997).
Mehnaz, S. and Lazarovits, G. et al., "Inoculation effects of Pseudomonas putida, Gluconacetobacter azotocaptans, and Azospirillum lipoferum on corn plant growth under greehouse conditions", *Microbial Ecology*, 51(3):326-335 (2006).
Miché, L. et al., "Effects of rice seed surface sterilization with hypocholorite on inoculated Burkholderiavietamiensis", *Applied and Environmental Microbiology*, 67(7):3046-3052 (2001).
Mueller and Sachs, "Engineering Microbiomes to Improve Plant and Animal Health", *Trends in Microbiology*, TIMI 1227, 12 pages. (2015). http://dx.doi.org/10.1016/j.tim.2015.07.009.
Murashige, T. et al., "A revised medium for rapid growth and bioassays with tobacco tissue cultures", *Physiologia Plantarum*, 15(3):473-497 (1962).

Pandey, P. et al., "Isolation of endophytic plant growth promoting Burkholderia sp. MSSP from root nodules of *Mimosa pudica*", *Current Science*, 89(1):177-180 (2005).
Panke-Buisse, P. et al., "Selection on soil microbiomes reveals reproducible impacts on plant function", *The ISME Journal*, 9: 980-989 (2015).
Pikovskaya, R.I., "Mobilization of phosphorus in soil connection with the vital activity of some microbial species", *Microbiologia*, 17:362-370 (1948) (and English Abstract).
"Pikovskaya's Broth (medium): Pikovskaya's Broth is recommended for cultivation of phosphate solubilizing microorganisms", M1719, HIMEDIA, Technical Data, 2 pages. (2011).
"Pikovskayas Agar: Pikovskayas Agar is recommended for detection of phosphate-solubilizing soil microorganisms", M520, HIMEDIA, Technical Data, 2 pages. (2011).
Pliego, C. et al., "Screening for candidate bacterial biocontrol agents against soilborne fungal plant pathogens", *Plant Soil*, 340(1-2):505-520 (2010).
Pliego, C. et al., "Plant Growth-Promoting Bacteria: Fundamentals and Exploitation", *Bacteria in Agrobiology: Crop Ecosystems*, Springer, USA, pp. 295-343 (2011).
Rao, A.V. et al., "Pattern of modulation and nitrogen fixation in mothbean", *Indian Journal of Agricultural Science*, 53(12):1035-1038 (1983).
Rodriguez, R.J. et al., "Stress tolerance in plants via habitat-adapted symbiosis", *The ISME Journal*, 2:404-416 (2008).
Ryan, R.P. et al., "Bacterial endophytes: recent developments and applications", *FEMS Microbiology Letters*, 278:1-9 (2008).
Saraf, M. et al., Chapter 13, "Perspectives of PGPR in Agri-Ecosystems", "Bacteria in Agrobiology: Crop Ecosystems," Springer, Dinesh K. Maheshwari, Editor, p. 361-385 (2011).
Scoholthof, H.B., "Molecular plant-microbe interactions that cut the mustard", *Plant Physiology*, 127:1476-1483 (2001).
Singer, A.C. et al., "Perspectives and vision for strain selection in bioaugmentation", *TRENDS in Biotechnology*, 23(2):74-77 (2005).
Stewart, Gordon S.A.B. et al., "Commitment of bacterial spores to germinate. A measure of the trigger reaction", *Biochem. J.*, 198:101-106 (1981).
Strobel, G. et al., "Bioprospecting for microbial endophytes and their natural products", *Microbiology and Molecular Biology Reviews*, 67(4):491-502 (2003).
Swenson et al., "Artificial ecosystem selection", *PNAS*, 97(16): 9110-9114 (2000).
Takeuchi, M. et al., "Taxonomic study of bacteria isolated from plants: proposal of *Sphingomonas rosa* sp. nov., *Sphingomonas pruni* sp. nov., *Sphingomonas asaccharolytica* sp. nov., and *Sphingomonas mali* sp. nov.", *International Journal of Systematic Bacteriology*, 45(2):334-341 (1995).
Venkateswarlu, B., et al., "Nitrogen fixation in Arid and Semi-arid agriculture: Opportunities and Contraints", *Agricultural Nitrogen Use & Its Environmental Implications*, New Delhi, pp. 415-436 (2007).
Wu, J et al., "Rhizoctonia fungi enhance the growth of the endangered orchid Cymbidium goeringii", *Botany*, 88(1):20-29 (2010).
Yanni, Y. G. et al., "Natural endophytic association between Rhizobium leguminosarum bv. trifolii and rice roots and assessment of its potential to promote rice growth", *Plant and Soil*, 194:99-114 (1997).
Yemm, E.W. and Willis, A.J., "The estimation of carbohydrates in plant extracts by anthrone", *Biochem. J.*, 57:508-514 (1954).
Zarraonaindia, I. et al., "The Soil Microbiome Influences Grapevine-Associated Microbiota", *mBio (American Society for Microbiology)*, 6(2): e02527-14, pp. 1-10 (2015).
Zhao, L.F. et al., "Colonization and plant growth promoting characterization of endophytic Pseudomonas chlororaphis strain Zong1 isolated from Sophora alopecuroides", Brazilian Journal of Microbiology, 44(2):623-631 (2013).
Zhao, L. et al., "Identification and characterization of the endophytic plant growth prompter Bacillus cereus strain MQ23 isolated from Sophora alopecuroides root nodules", *Brazilian Journal of Microbiology*, 42:567-575 (2011).

(56) References Cited

OTHER PUBLICATIONS

Zinniel, D.K. et al, "Isolation and characterisation of endophytic colonising bacteria from agronomic crops and prairie plants", *Applied and Environmental Microbiology*, 68(5):2198-2208 (2002).
Extended European Search Report in EP Application No. 12757224.6 dated Aug. 6, 2014, 7 pages.
International Search Report in International Application No. PCT/NZ2012/000041, mailed Jul. 17, 2012, 5 pages.
Written Opinion in International Application No. PCT/NZ2012/000041, mailed Jul. 17, 2012, 8 pages.
ternational Preliminary Report on Patentability in International Application No. PCT/NZ2012/000041, mailed Sep. 17, 2013, 2012, 9 pages.
International Search Report and Written Opinion in International Application No. PCT/NZ2013/000171, mailed Jan. 2, 2014, 14 pages.
International Preliminary Report on Patentability in International Application No. PCT/NZ2013/000171, dated Mar. 24, 2015, 9 pages.
International Search Report and Written Opinion in International Application No. PCT/NZ2014/000044, mailed May 21, 2014, 12 pages.

AMS drives dynamic changes in relative microbial abundance (NextGen seq.)

FIGURE 16

Microbiome analysis: Consortium candidates linked to trait improvement by changes in relative abundance

| Species | Soil | MC | R1 | |
|---|---|---|---|---|
| Species 194 | 0 | 2 | 0 | |
| Species 195 | 0 | 4 | 0 | |
| Species 196 | 0 | 20 | 131 | Isolation target |
| Species 197 | 0 | 1 | 0 | |
| Species 198 | 0 | 2 | 3 | |
| Species 199 | 0 | 182 | 103 | Isolation target |
| Species 200 | 0 | 0 | 1 | |
| Species 201 | 0 | 0 | 13 | |
| Species 202 | 0 | 0 | 2 | |
| Species 203 | 0 | 2 | 1 | |
| Species 204 | 0 | 0 | 2 | |
| Species 205 | 0 | 1642 | 2487 | Isolation target |
| Species 206 | 0 | 0 | 1 | |
| Species 207 | 0 | 2 | 3 | |

Broad Scope of Plants and Traits

| Accelerated Microbial Selection Target | Result Increase over microbe-free controls | Parameter Measured |
|---|---|---|
| GROWTH via ENDOPHYTES Corn | 12% - 10% 8 Treatments | Plant biomass (BM) |
| GROWTH Ryegrass | 28% - 10% 8 Treatments | Foliar weight (FW) |
| SUGAR CONTENT Basil | 14% - 10% 3 Treatments | mg WSC/g BM |

FIGURE 17

ACCELERATED DIRECTED EVOLUTION OF MICROBIAL CONSORTIA FOR THE DEVELOPMENT OF DESIRABLE PLANT PHENOTYPIC TRAITS

CROSS REFERENCE TO RELATED APPLICATIONS

This application is a Continuation Application of U.S. application Ser. No. 14/218,920, filed Mar. 18, 2014, which is a U.S. Utility Application under 35 U.S.C. §1.111(a) that claims priority pursuant to 35 U.S.C. §120, as a Continuation-in-Part Application, to International Application No. PCT/NZ2013/000171, filed on Sep. 19, 2013, which itself claims priority to New Zealand Application No. 602532, filed on Sep. 19, 2012.

The entire contents of: U.S. application Ser. No. 14/218,920, International Application No. PCT/NZ2013/000171, and New Zealand Application No. 602532 are hereby incorporated by reference in their entirety for all purposes.

FIELD

The present disclosure relates to methods for the screening, identification, and application of microorganisms of use in imparting beneficial properties to plants.

In particular aspects, the present disclosure provides for methods of developing microbial consortia through directed evolution and accelerated microbial selection. The microbial consortia developed by the methods of the present disclosure are capable of producing desirable plant phenotypic responses. Other aspects of the disclosure identify individual microbes, such as one or more microorganisms.

BACKGROUND

Known processes of imparting beneficial properties to plants, such as selective breeding, can be extremely costly, slow, limited in scope, and fraught with regulatory difficulties. Few commercial successes have eventuated from over two decades of large-scale investment into this technology.

Despite many decades of successful scientific research into the conventional breeding of highly-productive crops and into development of transgenic crops, relatively little research effort has been directed at development of plant traits via other means.

Thus, there is a great need in the art for the development of methods to improve plant traits that do not suffer from the drawbacks associated with the present technology.

BRIEF SUMMARY OF THE DISCLOSURE

The disclosure provides for an efficient, fast, and broadly applicable platform that can be utilized to develop microbes and microbial consortia that promote one or more desirable plant properties. In some embodiments, a single microbe is identified.

In certain aspects, the disclosure provides for the development of highly functional microbial consortia that help promote the development of a desired phenotypic or genotypic plant trait.

It is one object of the present disclosure to provide a method for the selection of one or more microorganism or composition of microorganisms that are of use in imparting one or more beneficial properties to a plant.

It is a further object of the disclosure to provide a system for assisting in the improvement of one or more plants.

Selective-Pressure Independent Accelerated Microbial Selection Methodology

In a first broad aspect of the present disclosure there is provided a method for the selection of one or more microorganisms capable of imparting one or more beneficial properties to a plant, the method comprising at least the steps of:
a) subjecting one or more plant (including for example seeds, seedlings, cuttings, and/or propagules thereof) to a growth medium in the presence of a first set of one or more microorganisms;
b) selecting one or more plant following step a);
c) acquiring a second set of one or more microorganisms associated with said one or more plant selected in step b) or plant growth media;
d) repeating steps a) to c) one or more times, wherein the second set of one or more microorganisms acquired in step c) is used as the first set of microorganisms in step a) of any successive repeat.

In one embodiment, the second set of one or more microorganisms are isolated from said one or more plant in step c).

In one embodiment, the first set of one or more microorganisms and/or the second set of one or more microorganisms are selected from the microorganisms detailed herein after.

In one embodiment, the growth medium is selected from the growth media detailed herein after.

In one embodiment, the step of subjecting one or more plant to a growth medium involves growing or multiplying the plant.

In one embodiment, two or more plants are subjected to a growth medium in the presence of one or more microorganisms. In other embodiments 1 to 10, or 1 to 20, or 1 to 30, or 1 to 40, or 1 to 50, or 1 to 60, or 1 to 70, or 1 to 80, or 1 to 90, or 1 to 100, or 1 to 200, or 1 to 500, or 1 to 1000, or 1 to 10,000 plants are subjected to a growth medium in the presence of the first set of microorganisms. In other embodiments, 10 or more, 20 or more, 100 or more, 300 or more, 500 or more, or 1000 or more plants are subjected to a growth medium in the presence of the first set of microorganisms.

In one embodiment, the one or more plant is selected (step b) on the basis of one or more selection criterion.

In one embodiment, the one or more plant is selected on the basis of one or more phenotypic trait. In one embodiment, the one or more plant is selected based on the presence of a desirable phenotypic trait. In one embodiment, the phenotypic trait is one of those detailed herein after.

In one embodiment, the one or more plant is selected on the basis of one or more genotypic trait. In one embodiment, the one or more plant is selected based on the presence of a desirable genotypic trait.

In one embodiment, the one or more plant is selected based on a combination of one or more genotypic and one or more phenotypic traits. In one embodiment, different selection criteria may be used in different iterations of a method of the disclosure.

In one embodiment, the second set of one or more microorganisms (step c) are isolated from the root, stem and/or foliar (including reproductive) tissue of the one or more plants selected. Alternatively, the second set of one or more microorganisms are isolated from whole plant tissue of the one or more plants selected. In another embodiment, the plant tissues may be surface sterilised and then one or more microorganisms isolated from any tissue of the one or more plants. This embodiment allows for the targeted selection of endophytic microorganisms. In another embodiment, the second set of one or more microorganisms may be isolated from the growth medium surrounding selected plants. In another embodiment, the second set of one or more microorganisms are acquired in crude form.

In one embodiment, the one or more microorganisms are acquired in step c) any time after germination.

In one embodiment, where two or more microorganisms are acquired in step c), the method further comprises the steps of separating the two or more microorganisms into individual isolates, selecting two or more individual isolates, and then combining the selected two or more isolates.

In another embodiment, the method further comprises repeating steps a) to c) one or more times, wherein where two or more microorganisms are acquired in step c), the two or more microorganisms are separated into individual isolates, two or more individual isolates are selected and then combined, and the combined isolates are used as the first set of one or more microorganism in step a) of the successive repeat. Accordingly, where reference is made to using the one or more microorganisms acquired in step c) in step a) of the method, it should be taken to include using the combined isolates of this embodiment of the disclosure.

In another embodiment, two or more methods of the disclosure may be performed separately and the second set of one or more microorganisms acquired in step c) of each separate method combined. In one embodiment, the combined microorganisms are used as the first set of one or more microorganisms in step a) of any successive repeat of the method of the disclosure.

In one embodiment, the methods of the first aspect of the disclosure may also be useful in identifying and/or selecting one or more endophytic microorganism capable of imparting one or more beneficial property to a plant.

In one embodiment, plant material (including for example seeds, seedlings, cuttings, and/or propagules thereof) may be used as the source of microorganisms for step a). In a preferred embodiment, the plant material used as a source for microorganisms in step a) is seed material. The plant material may be surface sterilised.

In another embodiment, the methods of the first aspect of the disclosure may be useful in identifying and/or selecting one or more unculturable microorganism capable of imparting one or more beneficial property to a plant. In this embodiment, plant material (including for example seeds, seedlings, cuttings, and/or propagules thereof) may be used as the source of microorganisms for step a). In a preferred embodiment, the plant material used as a source for microorganisms in step a) is explant material (for example, plant cuttings). The plant material may be surface sterilised.

In a second broad aspect, there is provided a method for assisting in the improvement of one or more plants according to a method as herein described, comprising arranging for the evaluation of said plant(s) in the presence of one or more microorganisms and/or compositions. The method preferably comprises at least the steps of a method of the first, seventh (and/or related) aspect, and/or the eighth (and/or related) aspect of the disclosure.

According to one embodiment, the plant(s) are for growing in a first region. The microorganism(s) may or may not (or at least to a significant extent) be present in the first region.

"Region" and "first region" are to be interpreted broadly as meaning one or more areas of land. The land areas may be defined by geographical/political/private land boundaries or by land areas having similar properties such as climate, soil properties, presence of a particular pest, predominant plant community, predominant climate, predominant geological formation, etc.

In an aspect, the evaluation is performed in a second region in which the microorganism(s) are present. Microorganisms may be obtained from other sources including microorganism depositaries and artificially associated with plant material and/or soil. Furthermore, while plant(s) may be cultivated in essentially a conventional manner, but in a region having microorganisms not normally associated with the plant(s), at least in the first region, artificial growing environments may alternatively be used as would be appreciated by those skilled in the art. Thus, possible beneficial microorganism/plant relationships may be identified that would not necessarily normally be utilised.

Preferably, the step of arranging comprises arranging for one or more of:
receipt or transmission of an identity of one or more plants or plant types to be evaluated;
receipt or transmission of plant material from one or more plants or plant types to be evaluated;
identification and/or selection of the microorganism(s) and/or composition(s);
acquisition of the microorganism(s) and/or composition(s); and
associating the microorganism(s) and/or composition(s) with the plant material.

Preferably, the method comprises evaluating (or arranging for said evaluation of) said plant(s) in the presence of said microorganism(s) and/or composition(s).

The step of evaluating preferably comprises performing one or more of the steps of a method described herein, in particular embodiments a method of one or more of the first aspect, seventh (and/or related) aspect or eighth (and/or related) aspect of the disclosure.

The various steps identified above may be performed by a single entity although at least two parties may be involved, a first party which makes a request and a second party which actions the request. Note that various agents may act for one or both parties and that varying levels of automation may be used. For example, in response to a particular request the microorganism(s) may be selected by a processor querying a database based on known microorganism associations for that or similar plant(s) with little or no input required from an operator.

Furthermore, the evaluation may be performed by the requesting party and/or in the first region. Performing the evaluation in the first region better ensures that the evaluation is accurate and that no unforeseen environmental factors that may impact on the plant(s) or the microorganism(s) are not considered.

Following the evaluation or during the course thereof, the method preferably further comprises one or more of:
receiving or sending one or more microorganisms (or at least the identity thereof) and/or composition(s) to the first region, including in combination with plant material; and
growing said plant(s) or other plants (preferably having similar properties) in the first region in the presence of said microorganism(s) and/or composition(s).

The method of the second aspect may be embodied by a first party:
identifying a need for an improvement in a plant(s);
sending the identity thereof and/or relevant plant material to a second party together with any relevant information, and
receiving plant material and/or one or more microorganisms and/or the identities thereof and/or composition(s).

The step of receiving is preferably performed following or as a result of an assessment of plant/microorganism and/or plant/composition associations. Preferably, the assessment is made using a method as described herein, in particular embodiments a method of the first aspect, the seventh (and/or related) aspect or the eighth (and/or related) aspect.

The method of the second aspect may additionally or alternatively be embodied by a second party:

receiving an identity of a plant(s) and/or relevant plant material from a first party together with any relevant information, and sending plant material and/or one or more microorganism(s) and/or the identities thereof and/or composition(s) to the first party.

The step of sending is preferably performed following or as a result of an assessment of plant/microorganism and/or plant/composition associations. Preferably, the assessment is made using a method described herein, in particular embodiments a method of the first aspect, the seventh (and/or related) aspect or the eighth (and/or related) aspect.

According to a third aspect, there is provided a system for implementing the method of the second aspect.

The system of the third aspect preferably includes one or more of:

means for receiving or transmitting an identity of one or more plants or plant types to be evaluated;

means for receiving or transmitting plant material from one or more plants or plant types to be evaluated;

means for identifying and/or selecting microorganism(s) and/or composition(s);

means for acquiring the microorganism(s) and/or composition(s);

means for associating the microorganism(s) and/or composition(s) with the plant material;

means for evaluating said plant(s) in the presence of said microorganism(s) and/or composition(s);

means for receiving or sending one or more microorganisms (or at least the identity thereof) and/or composition(s) to the first region, including in combination with plant material; and means for growing said plant(s) or other plants (preferably having similar properties) in the first region in the presence of said microorganism(s) and/or composition(s).

Means known to those skilled in the art may be used to provide the functionality required in the system of the third aspect. For example, conventional communication means, including the internet, may be used to convey the identities of plants/microorganisms; conventional carrier means may be used to convey the plant material/microorganisms/composition(s); conventional means and processes may be used to associate a microorganism and/or composition with plant material and conventional means for evaluating said plant(s) and/or the plant/microorganism and/or plant/composition associations may be used.

According to an embodiment, the system of the disclosure is embodied by a facility configured to transmit request(s) for an improvement in a plant(s) and subsequently to receive plant material and/or one or more microorganisms and/or the identities thereof, preferably following or as a result of an assessment of plant/microorganism associations. Preferably, the assessment is made using a method described herein, in particular embodiments a method of the first aspect, the seventh (and/or related) aspect, or the eighth (and/or related) aspect.

The system of the second aspect may additionally or alternatively be embodied by a facility configured to receive an identity of a plant(s) and/or relevant plant material from together with any relevant information; and send plant material and/or one or more microorganisms and/or the identities thereof and/or composition(s), preferably following or as a result of an assessment of plant/microorganism or plant/composition associations. Preferably, the assessment is made using a method described herein, in particular embodiments a method of the first aspect, the seventh (and/or related) aspect or the eighth (and/or related) aspect.

Accordingly to a fourth broad aspect of the disclosure, there is provided a microorganism acquired, selected, or isolated by a method as herein before described. In one embodiment, the microorganism is an endophyte. In one embodiment, the microorganism is unculturable.

In a fifth broad aspect of the disclosure, there is provided a method for the production of a composition to support plant growth, quality and/or health or a composition to suppress or inhibit the growth, quality and/or health of a plant, the method comprising the steps of a method herein before described and the additional step of combining the one or more microorganisms selected by the method with one or more additional ingredients.

In a sixth broad aspect of the disclosure, there is provided a composition comprising one or more microorganism of the fourth broad aspect or as prepared by a method of the fifth broad aspect.

In a seventh broad aspect of the disclosure there is provided a method for the selection of a composition which is capable of imparting one or more beneficial property to a plant, the method comprising at least the steps of:

a) culturing one or more microorganisms selected by a method of the first aspect of the disclosure in one or more media to provide one or more culture;

b) separating the one or more microorganism from the one or more media in the one or more culture after a period of time to provide one or more composition substantially free of microorganisms;

c) subjecting one or more plant (including for example seeds, seedlings, cuttings, and/or propagules thereof) to the one or more composition of step b);

d) selecting one or more composition from step c) if it is observed to impart one or more beneficial property to the one or more plants.

In an aspect of the disclosure related to (but distinct from) the seventh broad aspect of the disclosure there is provided a method for the selection of a composition which is capable of imparting one or more beneficial property to a plant, the method comprising at least the steps of:

a) culturing one or more microorganisms selected by a method of the first aspect of the disclosure in one or more media to form one or more culture;

b) inactivating the one or more culture of step a) to provide one or more composition containing one or more inactivated microorganisms;

c) subjecting one or more plant (including for example seeds, seedlings, cuttings, and/or propagules thereof) to the one or more composition of step b);

d) selecting one or more composition from step c) if it is observed to impart one or more beneficial property to the one or more plants.

In an eighth broad aspect of the disclosure there is provided a method for the selection of one or more microorganisms, which are capable of producing a composition which is capable of imparting one or more beneficial property to a plant, the method comprising at least the steps of:

a) culturing one or more microorganism selected by a method of the first aspect of the disclosure in one or more media to provide one or more culture;

b) separating the one or more microorganism from the one or more media in the one or more culture from step a)

after a period of time to provide one or more composition substantially free of microorganisms;

c) subjecting one or more plant (including for example seeds, seedlings, cuttings, and/or propagules thereof) to the one or more composition from step b);

d) selecting the one or more microorganisms associated with (or in other words used to produce the) one or more composition observed to impart one or more beneficial property to the one or more plants.

In an aspect related to (but distinct from) the eighth broad aspect of the disclosure there is provided a method for the selection of one or more microorganisms which are capable of producing a composition which is capable of imparting one or more beneficial property to a plant, the method comprising at least the steps of:

a) culturing one or more microorganism in one or more media to provide one or more culture;

b) separating the one or more microorganism from the one or more media in one or more culture after a period of time to provide one or more composition substantially free of microorganisms;

c) subjecting one or more plant (including for example seeds, seedlings, cuttings, and/or propagules thereof) to the one or more composition of step b);

d) selecting the one or more microorganisms associated with (or in other words used to produce the) one or more composition observed to impart one or more beneficial property to the one or more plants; and, e) using the one or more microorganisms selected in step d) in step a) of a method of the first, eighth or ninth aspects of the disclosure.

In a related aspect, step b) of the method of the eighth (and/or related) aspect could be substituted with the step of b) inactivating the one or more culture of step a) to provide one or more composition containing one or more inactivated microorganisms, and then using this composition in step c) of the process.

It should be appreciated that the methods of the first, seventh (and/or related) and eighth (and/or related) aspects may be combined in any combination, including the methods being run concurrently or sequentially in any number of iterations, with compositions and/or microorganisms selected or isolated from the methods being used individually or combined and used in iterative rounds of any one of the methods. By way of example, a method of the seventh (and/or related) aspect may be performed and a composition selected. The selection of a composition indicates that the one or more microorganism separated from the media in step b) is desirable for imparting beneficial properties to the one or more plant (as the one or more microorganism is capable of producing a selected composition). The one or more microorganism may then be used in another round of a method of the first aspect, seventh (and/or related) aspect or eighth (and/or related) aspect. Alternatively, the combination of methods could be run in reverse. This could be repeated any number of times in any order and combination. Accordingly the disclosure provides for the use of one or more microorganism, composition or plant acquired, selected or isolated by a method of the disclosure in any other method of the disclosure.

In a ninth broad aspect of the disclosure there is provided a composition obtained as a result of the methods of the seventh (and/or related) or eighth (and/or related) broad aspects of the disclosure.

In a tenth broad aspect of the disclosure there is provided a combination of two or more microorganisms acquired, selected, or isolated by a method as herein before described.

In another aspect, the disclosure provides the use of one or more composition and/or microorganism acquired, selected or isolated by a method of the disclosure for imparting one or more beneficial property to one or more plant.

It should be appreciated that methods of the disclosure may also involve applying steps a) to d) of the method of the first aspect on two or more different species of plant so as to identify combinations of microorganisms that may impart a positive benefit to one species and a negative benefit to another species simultaneously. For example, one may wish to identify a group of microorganisms that may simultaneously improve the growth and survival of a food crop and suppress or inhibit the growth of a competing crop or weed. This may be achieved by using two or more different plant species in step a) or running separate methods on different species and at appropriate points combining the microorganisms acquired in those methods and conducting further iterations.

The disclosure also provides plants selected in a method of the disclosure.

The disclosure also provides the use of a method of the disclosure in a plant breeding program, and a plant breeding program comprising conducting a method of the disclosure.

In another aspect, the disclosure provides a composition comprising one or more of the microorganisms listed in table 4. In one embodiment, the one or more microorganisms are endophytes.

In another aspect, the disclosure provides a composition comprising one or more microorganisms listed in table 3. In some aspects, a microbial consortium comprising at least one member chosen from the microbes listed in table 3 and combinations thereof are provided.

In another aspect, the disclosure provides a composition comprising one or more microorganisms listed in table 2. In some aspects, a microbial consortium comprising at least one member chosen from the microbes listed in table 2 and combinations thereof are provided.

In another aspect, the disclosure provides for the use of one or more microorganism listed in table 4 or a composition comprising same for increasing plant biomass. In one embodiment, the plant is maize. In one embodiment, the one or more microorganisms are endophytic. In some aspects, a microbial consortium comprising at least one member chosen from the microbes listed in table 4 and combinations thereof are provided.

In another aspect, the disclosure provides for the use of one or more microorganisms listed in table 3 or a composition comprising same for increasing carbohydrate concentrations in one or more plant. In one embodiment, the one or more plant is basil.

In another aspect, the disclosure provides for the use of one or more microorganisms listed in table 2 or a composition comprising same for increasing plant biomass. In one embodiment, the one or more plant is ryegrass.

The disclosure may also be said broadly to consist in the parts, elements, and features referred to or indicated in the specification of the application, individually or collectively, in any or all combinations of two or more of said parts, elements, or features, and where specific integers are mentioned herein which have known equivalents in the art to which the disclosure relates, such known equivalents are deemed to be incorporated herein as if individually set forth.

Further Embodiments of Accelerated Microbial Selection Methodology

Also described herein, is a method for selecting one or more microorganisms capable of imparting at least one beneficial property to a plant, comprising:

a) subjecting one or more plant to a growth medium in the presence of a first set of one or more microorganisms;
b) selecting one or more plant following step a);
c) acquiring a second set of one or more microorganisms from said one or more plant selected in step b);
d) repeating steps a) to c) one or more times, wherein the second set of one or more microorganisms acquired in step c) is used as the first set of microorganisms in step a) of any successive repeat; and
e) selecting one or more microorganisms that is associated with imparting a beneficial property to a plant.

Another embodiment taught herein, is a method for selecting one or more microorganisms capable of imparting at least one beneficial property to a plant, comprising:
a) subjecting one or more plant to a growth medium in the presence of a first set of one or more microorganisms;
b) selecting one or more plant following step a);
c) acquiring a second set of one or more microorganisms from said one or more plant selected in step b);
d) repeating steps a) to c) one or more times, wherein the second set of one or more microorganisms acquired in step c) is used as the first set of microorganisms in step a) of any successive repeat; and
e) isolating one or more microorganisms associated with imparting a beneficial property to a plant;
f) utilizing a molecular technique to characterize the one or more microorganisms isolated in step e); and
g) selecting one or more characterized microorganisms that is associated with imparting a beneficial property to a plant.

Further, the taught methods can include an additional step of h) combining the at least two microorganisms into a microbial consortium. In some instances, the microbes present at the end of the iterative accelerated microbial selection process will constitute a consortium. In other instances, one will select microbes from one or more accelerated microbial selection processes and then combine those microbes into a consortium. The consortium can be constructed with individual microbes identified in different accelerated microbial selection protocols. For instance, microbes identified in accelerated microbial selection protocols from previous years, geographic regions, plant species, soil types, etc, may be combined to construct a consortium.

In one embodiment, the one or more plant is ryegrass and the selecting of step b), of a second and any further successive repeat of steps a)-c), is based upon selecting the ryegrass plants with the largest biomass.

In another embodiment, the one or more plant is ryegrass and the selecting of step b), of a second and any further successive repeat of steps a)-c), is based upon selecting the ryegrass plants with the largest biomass, and wherein the one or more microorganisms comprise a member selected from the group consisting of: *Microbacterium ginsengiterrae, Bacillus cereus, Microbacterium oxydans, Rhizobium pusense, Curtobacterium ginsengisoli, Penicillium daleae, Brevundimonas vesicularis, Aeromicrobium ponti, Microbacterium hydrocarbonoxydans, Sphingopyxis chilensis, Arthrobacter keyser, Penicillium melinii, Rhizobium grahamii, Brevundimonas vesicularis, Rhizobium pusense, Curtobacterium ginsengisoli, Herbaspirillum rubrisubalbicans, Rhizobium etli, Exiguobacterium indicum, Mesorhizobium amorphae, Brevundimonas vesicularis, Arthrobacter keyser*, and combinations thereof.

In yet another embodiment, the one or more plant is basil and the selecting of step b), of a second and any further successive repeat of steps a)-c), is based upon selecting the basil plants with the greatest median sugar content.

Further, another embodiment teaches that the one or more plant is basil and the selecting of step b), of a second and any further successive repeat of steps a)-c), is based upon selecting the basil plants with the greatest median sugar content, and wherein the one or more microorganisms comprise a member selected from the group consisting of: *Sphingomonas mali, Flavobacterium micromati, Penicillium* sp., *Sphingobium chlorophenolicum, Massilia niastensis, Flavobacterium limicola, Rhizobium alamii, Sphingopyxis* sp., *Pelomonas aquatica, Azospirillum lipoferum, Mesorhizobium amorphae, Asticcacaulis taihuensis, Ralstonia solanacearum, Microbacterium foliorum, Trichoderma, Burkholderia megapolitana, Mesorhizobium amorphae, Umbelopsis* sp., *Aquabacterium fontiphilum, Rhodanobacter terrae, Sphingomonas mali, Sphingobium xenophagum, Pseudomonas moraviensis, Massilia niastensis, Flavobacterium limicola, Umbelopsis* sp., and combinations thereof.

In another embodiment, the one or more plant is maize and the selecting of step b), of a second and any further successive repeat of steps a)-c), is based upon selecting the maize plants with the largest biomass.

Still further, an embodiment teaches that the one or more plant is maize and the selecting of step b), of a second and any further successive repeat of steps a)-c), is based upon selecting the maize plants with the largest biomass, and wherein the one or more microorganisms comprise a member selected from the group consisting of: *Herbaspirillum frisingense, Acinetobacter* sp., *Xanthomonas translucens, Pseudomonas marginalis, Herbiconiux ginsengi, Burkholderia cepacia, Microbacterium oxydans, Pseudomonas moraviensis, Azotobacter chroococcum, Pseudomonas frederiksbergensis, Sphingomonas rosa, Rhizobium endophyticum, Bacillus thioparans, Terriglobus roseus, Novosphingobium rosa, Azospirillum lipoferum, Streptomyces thermocarboxydus, Herbaspirillum frisingense*, and combinations thereof.

The disclosure also presents a method of creating a microbial consortium capable of promoting at least one beneficial plant phenotypic trait, comprising:
a) subjecting at least one plant to a growth medium in the presence of a first plurality of microorganisms;
b) selecting at least one plant following step a);
c) acquiring a second plurality of microorganisms from said at least one plant selected in step b);
d) repeating steps a) to c) one or more times, wherein the second plurality of microorganisms acquired in step c) is used as the first plurality of microorganisms in step a) of any successive repeat;
e) isolating at least two microorganisms from said plurality of microorganisms that are associated with promoting at least one beneficial plant phenotypic trait;
f) utilizing a molecular technique to characterize the at least two isolated microorganisms;
g) selecting the at least two characterized microorganisms; and
h) combining the at least two microorganisms into a microbial consortia In a particular embodiment, the characterization of step f) comprises: determining the relative abundance of the at least two microorganisms that are associated with promoting at least one beneficial plant phenotypic trait.

In another embodiment, the characterization of step f) comprises: determining the relative abundance of the at least two microorganisms that are associated with promoting at least one beneficial plant phenotypic trait; and wherein the selecting of step g), comprises: choosing the at least two characterized microorganisms based on an increase in their relative abundance compared to their abundance from a previous iteration of steps a)-f). Also, the disclosure teaches an embodiment, wherein the at least two microorganisms chosen comprise microorganisms whose relative abundance increased at least 100%.

In an embodiment, the methods increase the frequency of the best microbes for a specific desired plant phenotype through iterative selection (selection on a plant phenotypic trait) and then the best consortia of microbes are isolated and applied as a seed or soil treatment. The disclosed methods are more powerful and efficient than traditional methods based upon mixing already known/characterized/identified microbes to create a microbial consortium. In embodiments, the present methods are not dependent upon the a priori existence of a known and characterized microbe. Rather, the iterative selection methods, in embodiments, are able to identify the best microbes for promoting a plant phenotypic trait, and only then are the microbes identified, if so desired.

In aspects, the directed evolution of a microbial consortium involves iterative selection of the best performing plants based upon the plants expression of a target trait and then subsequently transmitting the evolving microbial consortium to the next generation of plants through the iterative selection process. The iterative selection process can be repeated until the desired plant phenotype is achieved.

In an embodiment, directed evolution of a microbial community involves:
a) Populating the initial plant growth environment (soil or medium);
b) Growing plants without pressure;
c) Selecting best-performing individual plants (and the associated microbes); d) Recovering microbes from roots and foliage of selected plants;
e) Using these microbes to populate the soil/medium for the next round of plant growth and selection (many methods);
f) Repeating iterative selection process 2-5 (on average, can be any number) times until the improvement of the desired trait is achieved or plateaus;
g) After the terminal iteration, then isolating the microbes from the best-performing plants;
h) Reconstructing the microbial associations and developing a microbial consortia product.

The disclosed methods allow for the microbial consortia to be used with any other plant trait. Also, the methods taught herein enable improved fertilizer efficiency to minimize cost and environmental impact, allow for the production of more food per acre, and promote the production of more biomass for biofuels or lock up carbon.

In embodiments, methods taught herein use a multitude of molecular techniques, including: community fingerprinting—ARISA (Automated Ribosomal Intergenic Spacer Analysis); microbiome analysis to identify organisms via high throughput DNA sequencing & phylogenic analysis; microbial isolation & characterization via high throughput functional assays & improved culture techniques; quantitative analysis & microbe tracking via quantitative real time PCR (qRT-PCR) or fluorescent in situ hybridization (FISH) microscopy.

The taught methods allow for the monitoring of plant gene expression throughout the iterative process such that one can infer relationships between changes in the microbiome, plant gene expression, and the plant trait.

Thus, in embodiments, comparative analysis will enable one to identify novel plant genes and pathways that may serve as targets for crop improvement through: traditional breeding; plant genetic engineering; and targets for chemical induction or repression (i.e. drugable targets).

In an embodiment, the outcome of the methodology taught herein is microbes that improve targeted crop traits such as nutrient use efficiency, biological and physical challenges, as well as microbes than can assist crop breeding programs and improve the effectiveness and durability of transgenic crop traits.

In certain aspects, the accelerated microbial selection methodology creates multiple beneficial traits by using microbes (or consortia) with different beneficial effects in a single crop. Thus, the disclosed methods allow for the engineering of crop-microbe interactions via understanding of crop trait gene expression patterns and construction of recombinant microbes engineered to consolidate optimized activity in a single organism.

DEFINITIONS

Numbers and numerical ranges recited herein are to be understood to be modified by the term "about" as would be understood by one of ordinary skill in the art.

"About" can mean plus or minus a percent (e.g., ±5%) of the number, parameter, or characteristic so qualified, which would be understood as appropriate by a skilled artisan to the scientific context in which the term is utilized. Furthermore, since all numbers, values, and expressions referring to quantities used herein, are subject to the various uncertainties of measurement encountered in the art, then unless otherwise indicated, all presented values may be understood as modified by the term "about."

As used herein, the articles "a," "an," and "the" may include plural referents unless otherwise expressly limited to one-referent, or if it would be obvious to a skilled artisan from the context of the sentence that the article referred to a singular referent.

Where a numerical range is disclosed herein, then such a range is continuous, inclusive of both the minimum and maximum values of the range, as well as every value between such minimum and maximum values.

Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all subranges subsumed therein. For example, a stated range of from "1 to 10" should be considered to include any and all subranges between the minimum value of 1 and the maximum value of 10. Exemplary subranges of the range "1 to 10" include, but are not limited to, 1 to 6.1, 3.5 to 7.8, and 5.5 to 10.

As used herein the terms "microorganism" or "microbe" should be taken broadly. These terms, used interchangeably, include but are not limited to the two prokaryotic domains, Bacteria and Archaea, as well as eukaryotic fungi and protists.

The term "microbial consortia" refers to a subset of a microbial community of individual microbial species or strains of a species that can be described as carrying out a common function, or can be described as participating in, or leading to, or correlating with, a recognizable parameter or plant phenotypic trait. The community may comprise two or more species or strains of a species of microbes. In some instances, the microbes coexist within the community symbiotically.

The term "microbial community" means a group of microbes comprising two or more species or strains.

The term "directed evolution" is used in the broadest sense of the word "evolve" and does not necessarily refer to Mendelian inheritance. Thus, to "evolve" means to change. This change can be brought about by various parameters. In the examples that follow, a microbial community is evolved, i.e. the microbial community changes, over iterative selection steps according to the taught methods. In some embodiments, after several iterative rounds of accelerated microbial selection, the microbial community that results is drastically different from the microbial community present at the start of the method. Thus, in some embodiments, the methods take a random and heterogeneous microbial community, said members not necessarily working toward a desired function, but over the course of the iterative selection steps of the taught methods, a microbial community begins to emerge, wherein microbial species participate/correlate to a desired function, e.g. increasing a plant phenotypic trait of interest.

The term "accelerated microbial selection" or "AMS" is used interchangeably with the term "directed microbial selection" or "DMS" and refers to the iterative selection methodology elaborated upon in the disclosure.

The disclosure utilizes the term "plant" broadly to include all plant parts, seeds, seedlings, cuttings, propagules, root, stem, and/or foliar tissue. Further, a plant may be defined as the intimately associated plant rhizosphere.

A plant rhizosphere may include any component of the growth media influenced by the plant and its associated microbiome.

It should be appreciated that as referred to herein a "beneficial property to a plant" should be interpreted broadly to mean any property which is beneficial for any particular purpose including properties which may be beneficial to human beings, other animals, the environment, a habitat, an ecosystem, the economy, of commercial benefit, or of any other benefit to any entity or system. Thus, the benefit could be a desired change to a soil or growth medium. Accordingly, the term should be taken to include properties which may suppress, decrease, or block one or more characteristic of a plant, including suppressing, decreasing, or inhibiting the growth or growth rate of a plant. The disclosure may be described herein, by way of example only, in terms of identifying positive benefits to one or more plants or improving plants. However, it should be appreciated that the disclosure is equally applicable to identifying negative benefits that can be conferred to plants. Such beneficial properties include, but are not limited to, for example: improved growth, health and/or survival characteristics, suitability or quality of the plant for a particular purpose, structure, colour, chemical composition or profile, taste, smell, improved quality. In other embodiments, beneficial properties include, but are not limited to, for example: decreasing, suppressing or inhibiting the growth of a plant identified to be a weed; constraining the height and width of a plant to a desirable ornamental size; limiting the height of plants used in ground cover applications such as motorway and roadside banks and erosion control projects; slowing the growth of plants used in turf applications such as lawns, bowling greens and golf courses to reduce the necessity of mowing; reducing ratio of foliage/flowers in ornamental flowering shrubs; regulate production of and/or response to plant pheromones (resulting in increased tannin production in surrounding plant community and decreased appeal to foraging species).

As used herein, "improved" should be taken broadly to encompass improvement of a characteristic of a plant which may already exist in a plant or plants prior to application of the disclosure, or the presence of a characteristic which did not exist in a plant or plants prior to application of the disclosure.

By way of example, "improved" growth should be taken to include growth of a plant where the plant was not previously known to grow under the relevant conditions.

As used herein, "inhibiting and suppressing" and like terms should be taken broadly and should not be construed to require complete inhibition or suppression, although this may be desired in some embodiments.

To assist in describing the disclosure, the terms a "first set of one or more microorganisms" and a "second set of one or more microorganisms" may be used herein to distinguish the set or group of microorganism(s) applied in step a) and the set or group of microorganism(s) acquired in step c) of a method of the disclosure. In certain embodiments, the sets of microorganisms will be distinct; for example, the second set may be a subset of the first set, as a result of combining the first set with the plant and then selecting one or more plant based on one or more selection criterion. However, it should be appreciated that this may not always be the case and accordingly, the use of this terminology should not be construed in such a limited manner.

As is further described herein, microorganism(s) may be contained within a plant, on a plant, and/or within the plant rhizosphere or the plant growth medium. Accordingly, where reference is made herein to acquiring a second set of one or more microorganisms "from" a plant, unless the context requires otherwise, it should be taken to include reference to acquiring a second set of microorganisms contained within a plant, on a plant and/or within the plant rhizosphere, or also from the plant growth medium.

For ease of reference, the wording "associated with" may be used synonymously to refer to microorganism(s) contained within a plant, on a plant and/or within the plant rhizosphere.

As used herein, "isolate", "isolated" and like terms should be taken broadly. These terms are intended to mean that the one or more microorganism(s) has been separated at least partially from at least one of the materials with which it is associated in a particular environment (for example soil, water, plant tissue). "Isolate", "isolated" and like terms should not be taken to indicate the extent to which the microorganism(s) has been purified.

As used herein, "individual isolates" should be taken to mean a composition or culture comprising a predominance of a single genera, species or strain of microorganism, following separation from one or more other microorganisms. The phrase should not be taken to indicate the extent to which the microorganism has been isolated or purified. However, "individual isolates" preferably comprise substantially only one genus, species or strain of microorganism.

The term "growth medium" as used herein, should be taken broadly to mean any medium which is suitable to support growth of a plant. By way of example, the media may be natural or artificial including, but not limited to, soil, potting mixes, bark, vermiculite, hydroponic solutions alone and applied to solid plant support systems, and tissue culture gels. It should be appreciated that the media may be used alone or in combination with one or more other media. It may also be used with or without the addition of exogenous nutrients and physical support systems for roots and foliage.

A "composition to support plant growth, health, and/or quality" should be taken broadly to include compositions which may assist the growth, general health and/or survival of a plant, the condition of a plant, or assist in the maintaining or promoting any desired characteristic, quality, and/or trait. It should be taken to include maintaining or altering the production of one or more metabolite or other compound by a plant as well altering gene expression and the like. The phrase should not be taken to imply that the composition is able to support plant growth, quality and/or health on its own. However, in one embodiment the compositions are suitable for this purpose. Exemplary compositions of this aspect of the disclosure include but are not limited to plant growth media, plant mineral supplements and micronutrients, composts, fertilisers, potting mixes, insecticides, fungicides, media to protect against infection or infestation of pests and diseases, tissue culture media, seed coatings, hydroponic media, compositions that impart tolerance to drought or abiotic stress such as metal toxicity, compositions that modify soil pH.

A "composition to inhibit or suppress plant growth, health, and/or quality" should be taken broadly to include compositions which may assist in suppressing or inhibiting one or more characteristic, quality and/or trait of a plant, including its growth, general health and/or survival. It should be taken to include maintaining or altering the production of one or more metabolite or other compounds by a plant as well altering gene expression and the like. The phrase should not be taken to imply that the composition is able to suppress or inhibit plant growth, quality and/or health on its own. However, in one embodiment the compositions are suitable for this purpose. Exemplary compositions of this aspect of the disclosure include but are not limited to plant growth suppression media, weed killer, fertilisers, potting mixes, plant mineral supplements and micronutrients, composts, mixes, insecticides, fungicides, tissue culture media, seed coatings, hydroponic media, compositions that impart tolerance to drought or abiotic stress such as metal toxicity, and compositions that modify soil pH.

As used herein "inactivating" the one or more culture and "inactivated microorganisms" and like terms should be taken broadly to mean that the microorganisms are substantially inactivated, fixed, killed or otherwise destroyed. The term should not be taken to mean that all microorganisms are inactivated, killed or destroyed, however, this may be preferable. In one embodiment, the microorganisms are inactivated, fixed, killed or destroyed to the extent that self-sustained replication is no longer measurable using techniques known to one skilled in the art.

As used herein, a "composition substantially free of microorganisms" should be taken broadly and not be construed to mean that no microorganisms are present, although this may be preferred.

BRIEF DESCRIPTION OF THE DRAWINGS

These and other aspects of the present disclosure will become apparent from the following description, which is given by way of example only, with reference to the accompanying figures, in which:

FIG. 8). Triangles=rhizosphere communities identified in samples from microbe capture. Circles=rhizosphere communities from round 1 plants grown in Soil 5. Diamond=rhizosphere communities from round 1 plants grown in sterile sand & vermiculite. The MDS plot is constructed from data of the experiment from FIG. 8.

FIG. 16: shows that the methods of the disclosure drive dynamic change in relevant microbial abundance. For example, "Species 205" was not at a detectable abundance level in the natural soil, but the taught methods bring its abundance to 1642 after the capture step and an abundance of 2487 after R1. These data enable targeted isolation and selection of components of the evolved community for the construction of microbial consortia that can be linked to trait improvement by changes in relative abundance.

FIG. 17: is an overview of data obtained by utilizing the taught methods across a variety of plants: corn, ryegrass, and basil; and a variety of phenotypic plant traits: growth via endophytes in corn, growth in ryegrass, and ability to increase sugar content in basil.

DETAILED DESCRIPTION

Figure 1:
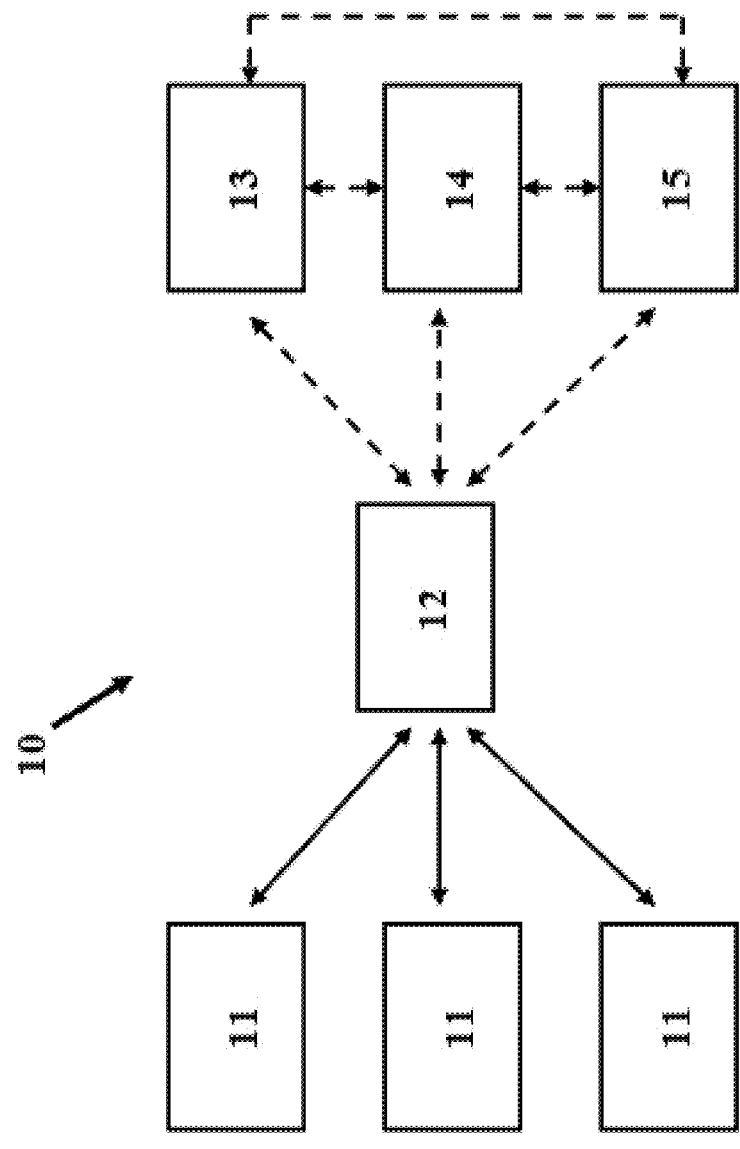
FIG. 1: shows a system according to an embodiment of the disclosure.

The following is a description of embodiments of the present disclosure. The disclosure will be further elucidated from the Examples provided hereafter.

The inventor(s) have found that one can readily identify microorganisms capable of imparting one or more beneficial property to one or more plants through use of a method of the disclosure. The method is broadly based on the presence of variability (such as genetic variability, or variability in the phenotype for example) in the plants and microbial populations used. The inventors have identified that this variability can be used to support a directed process of selection of one or more microorganisms, of use to a plant, and for identifying particular plant/microbe combinations which are of benefit for a particular purpose, and which may never have been recognised using conventional techniques.

Consequently, because the methods disclosed herein present an accelerated method of microbial selection, the methods are also applicable to a method of directed evolution of communities of microbes. That is, particular individual microbes and communities of microbes that are selected for by the accelerated selection methods lead to the evolution and development of the best consortia of microbes for producing a phenotypic plant trait of interest.

The methods of the disclosure may be used as a part of a plant breeding program. The methods may allow for, or at least assist with, the selection of plants which have a particular genotype/phenotype which is influenced by the microbial flora, in addition to identifying microorganisms and/or compositions that are capable of imparting one or more property to one or more plants.

In one aspect, the disclosure relates to a method for the selection of one or more microorganism(s) which are capable of imparting one or more beneficial property to a plant.

Broadly, the method comprises in one aspect, at least the steps of a) growing one or more plant in a growth medium in the presence of a first set of one or more microorganisms; b) selecting one or more plant following step a); and, c) acquiring a second set of one or more microorganisms associated with said one or more plant selected in step b). The one or more plants, growth medium and one or more microorganisms may be provided separately and combined in any appropriate order prior to step a). In particular, the disclosure provides an iterative method in which steps a) to c) may be repeated one or more times, wherein the one or more microorganisms acquired in step c) are used in step a) of the next cycle of the method. In one embodiment, steps a) to c) are repeated once. In another embodiment, steps a) to c) are repeated twice. In another embodiment, steps a) to c) are repeated three times. In another embodiment, steps a) to c) are repeated at least until a desired beneficial property is observed.

It will be appreciated that after a desired number of repeats of steps a) to c) the method may conclude with the acquisition of a set of one or more microorganisms from step c).

The set of microorganisms acquired during the iterative process of steps a) to c) can be a consortium of microbes that work together toward a common function or correlate with a function. Often, that common function relates to the development of a particular plant phenotypic trait of interest. By iteratively performing steps a)-c) the microbial community can evolve to include the most appropriate members of the community that correlate with a plant phenotypic trait of interest.

It should be appreciated that the methods do not require the identification of the microorganisms in the population acquired in step c) nor do they require a determination of the properties of individual microorganisms or combinations of microorganisms acquired. However, evaluation, identification, and/or a determination of the beneficial properties could be conducted if desired. For example, it may be preferred in some cases to isolate and identify the microbes in the final step of a method of the disclosure to determine their safety for commercial use and to satisfy regulatory requirements. In such cases, genetic and/or phenotypic analyses may be conducted.

Further, when developing a community, or consortia of microbes that cooperate towards, or correlate with, a particular function, it may be beneficial to know the identity of such consortia members, though this is not required.

In one embodiment, step a) is conducted using at least two plants. In other embodiments 10 to 20 plants are used. In yet other embodiments, 20 or more, 50 or more, 100 or more, 300 or more, 500 or more, or 1000 or more plants are used.

As noted hereinbefore, where two or more plants are used in a particular method of the disclosure they need not be the same variety or species.

For example, in one embodiment it may be desirable to select microorganisms that can impart a positive benefit to one plant variety or species and a negative benefit to another plant variety or species.

For example, the disclosed methods can be utilized to encourage the development of a desired phenotypic trait in a commercially important agriculture species while simultaneously imparting a negative influence on an undesirable weedy species that is often associated with the cultivation of the agricultural crop.

In one embodiment, where two or more microorganisms are acquired in step c), the method may further comprise the steps of separating the two or more microorganisms into individual isolates, selecting two or more individual isolates, and then combining the selected two or more isolates. This may result in the set of microorganisms acquired at the conclusion of a method of a disclosure.

However, in one embodiment, the combined isolates may then be used in step a) of successive rounds of the method. By way of example, from two, three, four, five, six, seven, eight, nine, ten, or more individual isolates may be combined. The inventors envisage an iterative method in which steps a) to c) are repeated one or more times, utilising these additional steps of separating, selecting, and combining with each repeat of the method, or interspersed or otherwise combined with a method in which individual isolates are not selected and combined.

In an embodiment, this procedure describes a process of evolving the microbial community, in the sense that the community (viewed as a plurality or community of microbes) changes and develops in response to the iterative accelerated selection procedure.

It is expected that these combinations will detect previously unknown, desirable property promoting (such as plant growth), synergistic interactions between microbes.

Using the iterative steps a) to c) will drive the starting population of two or more microorganisms toward microbes that interact with the plant to impart a desired property or characteristic. In other words, the process will allow for enrichment of suitable microorganisms within the plant microbiome.

As aforementioned, another way to characterize the iterative accelerated selection process is by viewing the process based upon the evolving community of microbes or consortia that work together toward a common function. Often, these microbial consortia will be correlated with helping to promote and develop a desired plant characteristic or phenotypic trait. Consequently, the disclosed methods present a process of directed evolution of microbial consortia. In aspects, this is a unique method by which to direct the evolution of microbial consortia, as the microbes do not have to be associated with one another naturally nor do the microbes have to ever have been naturally exposed to the plant or substrate utilized in the iterative selection process. Therefore, the directed evolution of microbial consortia achieved utilizing the present methods allows for, in some embodiments, the development of completely synthetic consortia that are highly specialized for working together to promote a plant phenotypic trait in a plant that the microbes would not naturally encounter.

Selection of individual isolates may occur on the basis of any appropriate selection criteria. For example, it may be random, it may be based on the beneficial property or properties observed by performing a method of the disclosure or, where information about the identity of the microorganism is known, it may be on the basis that the microorganism has previously been recognised to have a particular beneficial property.

In addition, two or more methods of the disclosure may be performed separately or in parallel and the microorganisms that result from each method combined into a single composition. For example, two separate methods may be performed, one to identify microorganisms capable of imparting one or more first beneficial property, and a second to identify microorganisms capable of imparting one or more second beneficial property. The separate methods may be directed to identifying microorganisms having the same beneficial property or having distinct beneficial properties. The microorganisms and plants used in the separate methods may be the same or different. If further optimisation of the microorganisms is desired, the single composition of microorganisms may be applied to one or more further rounds of a method of the disclosure. Alternatively, the single composition of microorganisms may be used, as desired, to confer the relevant properties to plant crops, without further optimisation. Combining two or more methods of the disclosure in this way allows for the selection and combination of microorganisms which may ordinarily be separated by time and/or space in a particular environment.

In certain embodiments of the disclosure, the methods may comprise growing or propagating one or more plants selected in step c) of the method, to grow the population of the second set of one or more microorganisms associated with the selected one or more plants, either at the conclusion of a method of the disclosure, or prior to using the second set of one or more microorganisms in step a) of any successive repeat of the method. If the one or more plants (with associated microorganisms) are grown or propagated at the conclusion of a method of the disclosure they may then be used or sold in that form.

Alternatively, one or more microorganisms may be isolated from the one or more plants, or one or more plant tissue and/or one or more plant part with associated microorganisms may be used as a crude source of the one or more microorganisms in any successive repeat of the disclosure, or for any other purpose at the conclusion of the method. In one embodiment, the seeds (with associated microorganisms) of one or more plant that has been grown or propagated may be obtained and used as a source of the one or more microorganisms in any successive repeat of the method. Alternatively, if obtained at the conclusion of a method of the disclosure, the seeds and associated microorganisms may be sold or used for any other purpose.

Further, the microbial community that has been evolved to impart and/or encourage the development of a plant phenotypic trait of interest may be sold or used for any purpose. In particular embodiments, the individual microbes, microbial consortia, or microbial community, derived by the present methods can be formulated as a composition that is utilized as a seed coating for commercially important agricultural crops.

Further, the individual microbes, or microbial consortia, or microbial communities, developed according to the disclosed methods can be combined with known actives available in the agricultural space, such as: pesticide, herbicide, bactericide, fungicide, insecticide, virucide, miticide, nemataicide, acaricide, plant growth regulator, rodenticide, anti-algae agent, biocontrol or beneficial agent. Further, the microbes, microbial consortia, or microbial communities developed according to the disclosed methods can be combined with known fertilizers. Such combinations may exhibit synergistic properties.

In some embodiments, when the microbe or microbial consortia identified according to the taught methods is combined with an active chemical agent one witnesses an additive effect on a plant phenotypic trait of interest.

In some embodiments, when the microbe or microbial consortia identified according to the taught methods is combined with a fertilizer one witnesses an additive effect on a plant phenotypic trait of interest.

In other embodiments, when the microbe or microbial consortia identified according to the taught methods is combined with an active chemical agent one witnesses a synergistic effect. The synergistic effect obtained by the taught methods can be quantified according to Colby's formula (i.e. (E)=X+Y−(X*Y/100). See Colby, R. S., "Calculating Synergistic and Antagonistic Responses of Herbicide Combinations", 1967 Weeds, vol. 15, pp. 20-22, incorporated herein by reference in its entirety. Thus, by "synergistic" is intended a component which, by virtue of its presence, increases the desired effect by more than an additive amount. The microbes and consortia of the present methods can synergistically increase the effectiveness of agricultural active compounds and also agricultural auxiliary compounds.

In other embodiments, when the microbe or microbial consortia identified according to the taught methods is combined with a fertilizer one witnesses a synergistic effect.

The composition comprising a microbial consortia developed according to the disclosure can be formulated with certain auxiliaries in order to improve the activity of a known active agricultural compound. This has the advantage that the amounts of active ingredient in the formulation may be reduced while maintaining the efficacy of the active compound, thus allowing costs to be kept as low as possible and any official regulations to be followed. In individual cases, it may also possible to widen the spectrum of action of the active compound since plants, where the treatment with a particular active ingredient without addition was insufficiently successful, can indeed be treated successfully by the addition of certain auxiliaries along with the disclosed microbial consortia. Moreover, the performance of the active may be increased in individual cases by a suitable formulation when the environmental conditions are not favorable.

Such auxiliaries that can be used in a composition comprising an active agricultural compound and a microbial consortia developed according to the disclosed methods can be an adjuvant. Frequently, adjuvants take the form of surface-active or salt-like compounds. Depending on their mode of action, they can roughly be classified as modifiers, activators, fertilizers, pH buffers, and the like. Modifiers affect the wetting, sticking, and spreading properties of a formulation. Activators break up the waxy cuticle of the plant and improve the penetration of the active ingredient into the cuticle, both short-term (over minutes) and long-term (over hours). Fertilizers such as ammonium sulfate, ammonium nitrate or urea improve the absorption and solubility of the active ingredient and may reduce the antagonistic behavior of active ingredients. pH buffers are conventionally used for bringing the formulation to an optimal pH.

Further methods and aspects of the disclosure are described herein after.

Microorganisms

As used herein the term "microorganism" should be taken broadly. It includes but is not limited to the two prokaryotic domains, Bacteria and Archaea, as well as eukaryotic fungi and protists.

By way of example, the microorganisms may include Proteobacteria (such as *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Delftia, Bradyrhizobiun, Sinorhizobium* and *Halomonas*), Firmicutes (such as *Bacillus, Paenibacillus, Lactobacillus, Mycoplasma*, and *Acetobacterium*), Actinobacteria (such as *Streptomyces, Rhodococcus, Microbacterium*, and *Curtobacterium*), and the fungi Ascomycota (such as *Trichoderma, Ampelomyces, Coniothyrium, Paecoelomyces, Penicillium, Cladosporium, Hypocrea, Beauveria, Metarhizium, Verticullium, Cordyceps, Pichea*, and *Candida*, Basidiomycota (such as *Coprinus, Corticium*, and *Agaricus*) and Oomycota (such as *Pythium, Mucor*, and *Mortierella*).

In one embodiment, the microorganism is an endophyte or an epiphyte or a microorganism inhabiting the plant rhizosphere. In one embodiment, the microorganism is a seed-borne endophyte.

In certain embodiments, the microorganism is unculturable. This should be taken to mean that the microorganism is not known to be culturable or is difficult to culture using methods known to one skilled in the art.

Microorganisms of use in the methods of the present disclosure (for example, the first set of one or more microorganisms) may be collected or obtained from any source or contained within and/or associated with material collected from any source. In some embodiments, the microorganisms are collected, obtained, captured, or otherwise derived, from a soil media (or any growth media). In some embodiments, the microorganisms are collected, obtained, captured, or otherwise derived, from a soil media (or any growth media) and are not otherwise associated with a particular plant.

In one embodiment, the first set of one or more microorganisms are obtained from any general terrestrial environment, including its soils, plants, fungi, animals (including invertebrates) and other biota, including the sediments, water and biota of lakes and rivers; from the marine environment, its biota and sediments (for example sea water, marine muds, marine plants, marine invertebrates (for example sponges), marine vertebrates (for example, fish)); the terrestrial and marine geosphere (regolith and rock, for example crushed subterranean rocks, sand and clays); the cryosphere and its meltwater; the atmosphere (for example, filtered aerial dusts, cloud and rain droplets); urban, industrial and other man-made environments (for example, accumulated organic and mineral matter on concrete, roadside gutters, roof surfaces, road surfaces).

In another embodiment the first set of one or more microorganisms are obtained from a source likely to favour the selection of appropriate microorganisms. By way of example, the source may be a particular environment in which it is desirable for other plants to grow, or which is thought to be associated with terroir. In another example, the source may be a plant having one or more desirable traits, for example a plant which naturally grows in a particular environment or under certain conditions of interest. By way of example, a certain plant may naturally grow in sandy soil or sand of high salinity, or under extreme temperatures, or with little water, or it may be resistant to certain pests or disease present in the environment, and it may be desirable for a commercial crop to be grown in such conditions, particularly if they are, for example, the only conditions available in a particular geographic location. By way of further example, the microorganisms may be collected from commercial crops grown in such environments, or more specifically from individual crop plants best displaying a trait of interest amongst a crop grown in any specific environment: for example the fastest-growing plants amongst a crop grown in saline-limiting soils, or the least damaged plants in crops exposed to severe insect damage or disease epidemic, or plants having desired quantities of certain metabolites and other compounds, including fibre content, oil content, and the like, or plants displaying desirable colours, taste or smell. The microorganisms may be collected from a plant of interest or any material occurring in the environment of interest, including fungi and other animal and plant biota, soil, water, sediments, and other elements of the environment as referred to previously.

In certain embodiments, the microorganisms are sourced from previously performed methods of the disclosure (for example, the microorganisms acquired in step c) of the method), including combinations of individual isolates separated from the second set of microorganisms isolated in step c) or combinations of microorganisms resulting from two or more separately performed methods of the disclosure.

While the disclosure obviates the need for pre-existing knowledge about a microorganism's desirable properties with respect to a particular plant species, in one embodiment a microorganism or a combination of microorganisms of use in the methods of the disclosure may be selected from a pre-existing collection of individual microbial species or strains based on some knowledge of their likely or predicted benefit to a plant. For example, the microorganism may be predicted to: improve nitrogen fixation; release phosphate from the soil organic matter; release phosphate from the inorganic forms of phosphate (e.g. rock phosphate); "fix carbon" in the root microsphere; live in the rhizosphere of the plant thereby assisting the plant in absorbing nutrients from the surrounding soil and then providing these more readily to the plant; increase the number of nodules on the plant roots and thereby increase the number of symbiotic nitrogen fixing bacteria (e.g. *Rhizobium* species) per plant and the amount of nitrogen fixed by the plant; elicit plant defensive responses such as ISR (induced systemic resistance) or SAR (systemic acquired resistance) which help the plant resist the invasion and spread of pathogenic microorganisms; compete with microorganisms deleterious to plant growth or health by antagonism, or competitive utilisation of resources such as nutrients or space; change the colour of one or more part of the plant, or change the chemical profile of the plant, its smell, taste or one or more other quality.

In one embodiment a microorganism or combination of microorganisms (the first set of one or more microorganisms) is selected from a pre-existing collection of individual microbial species or strains that provides no knowledge of their likely or predicted benefit to a plant. For example, a collection of unidentified microorganisms isolated from plant tissues without any knowledge of their ability to improve plant growth or health, or a collection of microorganisms collected to explore their potential for producing compounds that could lead to the development of pharmaceutical drugs.

In one embodiment, the microorganisms are isolated from the source material (for example, soil, rock, water, air, dust, plant or other organism) in which they naturally reside. The microorganisms may be provided in any appropriate form, having regard to its intended use in the methods of the disclosure. However, by way of example only, the microorganisms may be provided as an aqueous suspension, gel, homogenate, granule, powder, slurry, live organism or dried material. The microorganisms may be isolated in substantially pure or mixed cultures. They may be concentrated, diluted or provided in the natural concentrations in which they are found in the source material. For example, microorganisms from saline sediments may be isolated for use in this disclosure by suspending the sediment in fresh water and allowing the sediment to fall to the bottom. The water containing the bulk of the microorganisms may be removed by decantation after a suitable period of settling and either applied directly to the plant growth medium, or concentrated by filtering or centrifugation, diluted to an appropriate concentration and applied to the plant growth medium with the bulk of the salt removed. By way of further example, microorganisms from mineralized or toxic sources may be similarly treated to recover the microbes for application to the plant growth material to minimise the potential for damage to the plant.

In another embodiment, the microorganisms (including the first set of one or more microorganism and/or the second set of one or more microorganisms) are used in a crude form, in which they are not isolated from the source material in which they naturally reside. For example, the microorganisms are provided in combination with the source material in which they reside; for example, as soil, or the roots, seed or foliage of a plant. In this embodiment, the source material may include one or more species of microorganisms.

In an embodiment, a mixed population of microorganisms is used in the methods of the disclosure.

In embodiments of the disclosure where the microorganisms are isolated from a source material (for example, the material in which they naturally reside), any one or a combination of a number of standard techniques which will be readily known to skilled persons may be used. However, by way of example, these in general employ processes by which a solid or liquid culture of a single microorganism can be obtained in a substantially pure form, usually by physical separation on the surface of a solid microbial growth medium or by volumetric dilutive isolation into a liquid microbial growth medium. These processes may include isolation from dry material, liquid suspension, slurries or homogenates in which the material is spread in a thin layer over an appropriate solid gel growth medium, or serial dilutions of the material made into a sterile medium and inoculated into liquid or solid culture media.

In one embodiment, the material containing the microorganisms may be pre-treated prior to the isolation process in order to either multiply all microorganisms in the material, or select portions of the microbial population, either by enriching the material with microbial nutrients (for example, nitrates, sugars, or vegetable, microbial or animal extracts), or by applying a means of ensuring the selective survival of only a portion of the microbial diversity within the material (for example, by pasteurising the sample at 60° C.-80° C. for 10-20 minutes to select for microorganisms resistant to heat exposure (for example, bacilli), or by exposing the sample to low concentrations of an organic solvent or sterilant (for example, 25% ethanol for 10 minutes) to enhance the survival of actinomycetes and spore-forming or solvent-resistant microorganisms). Microorganisms can then be isolated from the enriched materials or materials treated for selective survival, as above.

In an embodiment of the disclosure endophytic or epiphytic microorganisms are isolated from plant material. Any number of standard techniques known in the art may be used and the microorganisms may be isolated from any appropriate tissue in the plant, including for example root, stem and leaves, and plant reproductive tissues. By way of example, conventional methods for isolation from plants typically include the sterile excision of the plant material of interest (e.g. root or stem lengths, leaves), surface sterilisation with an appropriate solution (e.g. 2% sodium hypochlorite), after which the plant material is placed on nutrient medium for microbial growth (see, for example, Strobel G and Daisy B (2003) Bioprospecting for microbial endophytes and their natural products. Microbiology and Molecular Biology Reviews 67 (4): 491-502; Zinniel D K et al. (2002) Isolation and characterisation of endophytic colonising bacteria from agronomic crops and prairie plants. Applied and Environmental Microbiology 68 (5): 2198-2208). In one preferred embodiment of the disclosure, the microorganisms are isolated from root tissue. Further methodology for isolating microorganisms from plant material are detailed herein after.

It should be appreciated that the second set of microorganisms acquired in step c) of a method of the disclosure may be isolated from a plant or plant material, surface or growth media associated with a selected plant using any appropriate techniques known in the art, including but not limited to those techniques described herein. However, in certain embodiments, as mentioned herein before, the microorganism(s) may be used in crude form and need not be isolated from a plant or a media. For example, plant material or growth media which includes the microorganisms identified to be of benefit to a selected plant may be obtained and used as a crude source of microorganisms for the next round of the method or as a crude source of microorganisms at the conclusion of the method. For example, whole plant material could be obtained and optionally processed, such as mulched or crushed. Alternatively, individual tissues or parts of selected plants (such as leaves, stems, roots, and seeds) may be separated from the plant and optionally processed, such as mulched or crushed. In certain embodiments, one or more part of a plant which is associated with the second set of one or more microorganisms may be removed from one or more selected plants and, where any successive repeat of the method is to be conducted, grafted on to one or more plant used in step a).

The methods of the disclosure may be described herein in terms of the second set of one or more microorganisms being isolated from their source material. However, unless the context requires otherwise, this should also be taken to include reference to the use of microorganisms in crude form in which they have not been isolated from the source material.

Plants

Any number of a variety different plants, including mosses and lichens and algae, may be used in the methods of the disclosure. In preferred embodiments, the plants have economic, social and/or environmental value. For example, the plants may include those of use: as food crops; as fibre crops; as oil crops; in the forestry industry; in the pulp and paper industry; as a feedstock for biofuel production; and/or, as ornamental plants. In other embodiments, the plants may be economically socially and or environmentally undesirable, such as weeds. The following is a list of non-limiting examples of the types of plants the methods of the disclosure may be applied to:

Food Crops:
Cereals (maize, rice, wheat, barley, sorghum, millet, oats, rye, triticale, buckwheat);
leafy vegetables (brassicaceous plants such as cabbages, broccoli, bok Choy, rocket; salad greens such as spinach, cress, lettuce);
fruiting and flowering vegetables (e.g. avocado, sweet corn, artichokes, curcubits e.g. squash, cucumbers, melons, courgettes, pumpkins; solononaceous vegetables/fruits e.g. tomatoes, eggplant, capsicums);
podded vegetables (groundnuts, peanuts, peas, soybeans, beans, lentils, chickpea, okra);
bulbed and stem vegetables (asparagus, celery, *Allium* crops e.g garlic, onions, leeks);
roots and tuberous vegetables (carrots, beet, bamboo shoots, cassava, yams, ginger, Jerusalem artichoke, parsnips, radishes, potatoes, sweet potatoes, taro, turnip, wasabi);
sugar crops including sugar beet (*Beta vulgaris*), sugar cane (*Saccharum officinarum*);
crops grown for the production of non-alcoholic beverages and stimulants (coffee, black, herbal and green teas, cocoa, tobacco);
fruit crops such as true berry fruits (e.g. kiwifruit, grape, currants, gooseberry, guava, feijoa, pomegranate), citrus fruits (e.g. oranges, lemons, limes, grapefruit), epigynous fruits (e.g. bananas, cranberries, blueberries), aggregate fruit (blackberry, raspberry, boysenberry), multiple fruits (e.g. pineapple, fig), stone fruit crops (e.g. apricot, peach, cherry, plum), pip-fruit (e.g. apples, pears) and others such as strawberries, sunflower seeds;
culinary and medicinal herbs e.g. rosemary, basil, bay laurel, coriander, mint, dill, *Hypericum*, foxglove, alovera, rosehips);
crop plants producing spices e.g. black pepper, cumin cinnamon, nutmeg, ginger, cloves, saffron, cardamom, mace, paprika, masalas, star anise;
crops grown for the production of nuts e.g. almonds and walnuts, Brazil nut, cashew nuts, coconuts, chestnut, macadamia nut, pistachio nuts; peanuts, pecan nuts;
crops grown for production of beers, wines and other alcoholic beverages e.g grapes, hops;
oilseed crops e.g. soybean, peanuts, cotton, olives, sunflower, sesame, lupin species and brassicaceous crops (e.g. canola/oilseed rape); and,
edible fungi e.g. white mushrooms, Shiitake and oyster mushrooms;

Plants Used in Pastoral Agriculture:
legumes: *Trifolium* species, *Medicago* species, and *Lotus* species; White clover (*T. repens*); Red clover (*T. pratense*); Caucasian clover (*T. ambigum*); subterranean clover (*T. subterraneum*); Alfalfa/Lucerne (*Medicago sativum*); annual medics; barrel medic; black medic; Sainfoin (*Onobrychis viciifolia*); Birdsfoot trefoil (*Lotus corniculatus*); Greater Birdsfoot trefoil (*Lotus pedunculatus*);
seed legumes/pulses including Peas (*Pisum sativum*), Common bean (*Phaseolus vulgaris*), Broad beans (*Vicia faba*), Mung bean (*Vigna radiata*), Cowpea (*Vigna unguiculata*), Chick pea (*Cicer arietum*), Lupins (*Lupinus* species);
Cereals including Maize/corn (*Zea mays*), Sorghum (*Sroghum* spp.), Millet (*Panicum miliaceum, P. sumatrense*), Rice (*Oryza sativa indica, Oryza sativa japonica*), Wheat (*Triticum sativa*), Barley (*Hordeum vulgare*), Rye (*Secale cereale*), Triticale (*Triticum×Secale*), Oats (*Avena fatua*);
Forage and Amenity grasses: Temperate grasses such as *Lolium* species; *Festuca* species; *Agrostis* spp., Perennial ryegrass (*Lolium perenne*); hybrid ryegrass (*Lolium hybridum*); annual ryegrass (*Lolium multiflorum*), tall fescue (*Festuca arundinacea*); meadow fescue (*Festuca pratensis*); red fescue (*Festuca rubra*); *Festuca ovina*; Festuloliums (*Lolium×Festuca* crosses); Cocksfoot (*Dactylis glomerata*); Kentucky bluegrass *Poa pratensis; Poa palustris; Poa nemoralis; Poa trivialis; Poa compresa; Bromus* species; *Phalaris* (*Phleum* species); *Arrhenatherum elatius; Agropyron* species; *Avena strigosa; Setaria italic;*
Tropical grasses such as: *Phalaris* species; *Brachiaria* species; *Eragrostis* species; *Panicum* species; Bahai grass (*Paspalum notatum*); *Brachypodium* species; and,
Grasses used for biofuel production such as Switchgrass (*Panicum virgatum*) and *Miscanthus* species;

Fibre Crops:
cotton, hemp, jute, coconut, sisal, flax (*Linum* spp.), New Zealand flax (*Phormium* spp.); plantation and natural forest species harvested for paper and engineered wood fibre products such as coniferous and broadleafed forest species;

Tree and Shrub Species Used in Plantation Forestry and Bio-Fuel Crops:
Pine (*Pinus* species); Fir (*Pseudotsuga* species); Spruce (*Picea* species); Cypress (*Cupressus* species); Wattle (*Acacia* species); Alder (*Alnus* species); Oak species (*Quercus* species); Redwood (*Sequoiadendron* species); willow (*Salix* species); birch (*Betula* species); Cedar (*Cedurus* species); Ash (*Fraxinus* species); Larch (*Larix* species); *Eucalyptus* species; Bamboo (*Bambuseae* species) and Poplars (*Populus* species).

Plants Grown for Conversion to Energy, Biofuels or Industrial Products by Extractive, Biological, Physical or Biochemical Treatment:
Oil-producing plants such as oil palm, jatropha, soybean, cotton, linseed;
Latex-producing plants such as the Para Rubber tree, *Hevea brasiliensis* and the Panama Rubber Tree *Castilla elastica;*
plants used as direct or indirect feedstocks for the production of biofuels i.e. after chemical, physical (e.g. thermal or catalytic) or biochemical (e.g. enzymatic pre-treatment) or biological (e.g. microbial fermentation) transformation during the production of biofuels, industrial solvents or chemical products e.g. ethanol or butanol, propane diols, or other fuel or industrial material including sugar crops (e.g. beet, sugar cane), starch-producing crops (e.g. C3 and C4 cereal crops and tuberous crops), cellulosic crops such as forest trees (e.g. Pines, Eucalypts) and Graminaceous and Poaceous plants such as bamboo, switch grass, *miscanthus;* crops used in energy, biofuel or industrial chemical production via gasification and/or microbial or catalytic conversion of the gas to biofuels or other industrial raw materials such as solvents or plastics, with or without the production of biochar (e.g. biomass crops such as coniferous, eucalypt, tropical or broadleaf forest trees, graminaceous and poaceous crops such as bamboo, switch grass, *miscanthus*, sugar cane, or hemp or softwoods such as poplars, willows; and, biomass crops used in the production of biochar;

Crops Producing Natural Products Useful for the Pharmaceutical, Agricultural Nutraceutical and Cosmeceutical Industries:

crops producing pharmaceutical precursors or compounds or nutraceutical and cosmeceutical compounds and materials for example, star anise (shikimic acid), Japanese knotweed (resveratrol), kiwifruit (soluble fibre, proteolytic enzymes);

Floricultural, Ornamental and Amenity Plants Grown for their Aesthetic or Environmental Properties:

Flowers such as roses, tulips, chrysanthemums;

Ornamental shrubs such as *Buxus, Hebe, Rosa, Rhododendron, Hedera*

Amenity plants such as *Platanus, Choisya, Escallonia, Euphorbia, Carex*

Mosses such as sphagnum moss

Plants Grown for Bioremediation:

*Helianthus, Brassica, Salix, Populus, Eucalyptus*

It should be appreciated that a plant may be provided in the form of a seed, seedling, cutting, propagule, or any other plant material or tissue capable of growing. In one embodiment the seed may surface-sterilised with a material such as sodium hypochlorite or mercuric chloride to remove surface-contaminating microorganisms. In one embodiment, the propagule is grown in axenic culture before being placed in the plant growth medium, for example as sterile plantlets in tissue culture.

Growth Medium

In one embodiment, the growth medium is a naturally occurring medium such as soil, sand, mud, clay, humus, regolith, rock, or water. In another embodiment, the growth medium is artificial. Such an artificial growth medium may be constructed to mimic the conditions of a naturally occurring medium, however, this is not necessary. Artificial growth media can be made from one or more of any number and combination of materials including sand, minerals, glass, rock, water, metals, salts, nutrients, water. In one embodiment, the growth medium is sterile. In another embodiment, the growth medium is not sterile.

The medium may be amended or enriched with additional compounds or components, for example, a component which may assist in the interaction and/or selection of specific groups of microorganisms with the plant and each other.

Further, in some embodiments, the medium may be amended or enriched with additional compounds or components, for example, a compound or composition which provides any specific plant, microbial, or soil benefit (e.g. molybdenum, humates) or modifies any aspect of any soil chemistry, microbial or animal properties e.g. the nitrification inhibitor dicyaniamide (DCD), or microbial product(s) such as biopesticide(s) or biofertilizer(s).

In certain embodiments of the disclosure, the growth medium may be pre-treated to assist in the survival and/or selection of certain microorganisms. For example, the medium may be pre-treated by incubating in an enrichment media to encourage the multiplication of endogenous microbes that may be present therein. By way of further example, the medium may be pre-treated by incubating in a selective medium to encourage the multiplication of specific groups of microorganisms. A further example includes the growth medium being pre-treated to exclude a specific element of the microbial assemblage therein; for example pasteurization (to remove spore-forming bacteria and fungi) or treatment with organic solvents such as various alcohols to remove microorganisms sensitive to these materials but allow the survival of actinomycetes and spore-forming bacteria, for example.

Methods for pre-treating or enriching may be informed by culture independent microbial community profiling techniques that provide information on the identity of microbes or groups of microbes present. These methods may include, but are not limited to, sequencing techniques including high throughput sequencing and phylogenetic analysis, or microarray-based screening of nucleic acids coding for components of rRNA operons or other taxonomically informative loci.

Growth Conditions

In accordance with the methods of the disclosure one or more plant is subjected to one or more microorganism and a growth medium. The plant is preferably grown or allowed to multiply in the presence of the one or more microorganism(s) and growth medium. The microorganism(s) may be present in the growth medium naturally without the addition of further microorganisms, for example in a natural soil. The growth medium, plant and microorganisms may be combined or exposed to one another in any appropriate order. In one embodiment, the plant, seed, seedling, cutting, propagule or the like is planted or sown into the growth medium which has been previously inoculated with the one or more microorganisms. Alternatively, the one or more microorganisms may be applied to the plant, seed, seedling, cutting, propagule or the like which is then planted or sown into the growth medium (which may or may not contain further microorganisms). In another embodiment, the plant, seed, seedling, cutting, propagule or the like is first planted or sown into the growth medium, allowed to grow, and at a later time the one or more microorganisms are applied to the plant, seed, seedling, cutting, propagule or the like and/or the growth medium itself is inoculated with the one or more microorganisms.

The microorganisms may be applied to the plant, seedling, cutting, propagule or the like and/or the growth medium using any appropriate techniques known in the art. However, by way of example, in one embodiment, the one or more microorganisms are applied to the plant, seedling, cutting, propagule or the like by spraying or dusting. In another embodiment, the microorganisms are applied directly to seeds (for example as a coating) prior to sowing. In a further embodiment, the microorganisms or spores from microorganisms are formulated into granules and are applied alongside seeds during sowing. In another embodiment, microorganisms may be inoculated into a plant by cutting the roots or stems and exposing the plant surface to the microorganisms by spraying, dipping or otherwise applying a liquid microbial suspension, or gel, or powder. In another embodiment the microorganism(s) may be injected directly into foliar or root tissue, or otherwise inoculated directly into or onto a foliar or root cut, or else into an excised embryo, or radicle or coleoptile. These inoculated plants may then be further exposed to a growth media containing further microorganisms, however, this is not necessary. In certain embodiments, the microorganisms are applied to the plant, seedling, cutting, propagule or the like and/or growth medium in association with plant material (for example, plant material with which the microorganisms are associated).

In other embodiments, particularly where the microorganisms are unculturable, the microorganisms may be transferred to a plant by any one or a combination of grafting, insertion of explants, aspiration, electroporation, wounding, root pruning, induction of stomatal opening, or any physical, chemical or biological treatment that provides the opportunity for microbes to enter plant cells or the intercellular space. Persons of skill in the art may readily appreciate a number of alternative techniques that may be used.

It should be appreciated that such techniques are equally applicable to application of the first set of one or more microorganisms and the second set of microorganisms when used in step a) of a successive repeat of the method.

In one embodiment the microorganisms infiltrate parts of the plant such as the roots, stems, leaves and/or reproductive plant parts (become endophytic), and/or grow upon the surface of roots, stems, leaves and/or reproductive plant parts (become epiphytic) and/or grow in the plant rhizosphere. In one preferred embodiment microorganism(s) form a symbiotic relationship with the plant.

The growth conditions used may be varied depending on the species of plant, as will be appreciated by persons skilled in the art. However, by way of example, for clover, in a growth room one would typically grow plants in a soil containing approximately $\frac{1}{3}^{rd}$ organic matter in the form of peat, $\frac{1}{3}^{rd}$ compost, and $\frac{1}{3}^{rd}$ screened pumice, supplemented by fertilisers typically containing nitrates, phosphates, potassium and magnesium salts and micronutrients and at a pH of between 6 and 7. The plants may be grown at a temperature between 22-24° C. in an 16:8 period of daylight:darkness, and watered automatically.

For example, in the case of winter wheat varieties, mainly sown in the Northern Hemisphere, it may be important to select plants that display early tillering after exposure of seed to a growth medium containing microorganisms under conditions of light and temperature similar to those experienced by the winter wheat seed in the Northern Hemisphere, since early tillering is a trait related to winter survival, growth and eventual grain yield in the summer Or, a tree species may be selected for improved growth and health at 4-6 months as these traits are related to the health and growth rate and size of trees of 10 years later, an impractical period product development using this disclosure.

Selection

Typically, following growth of the one or more plants in the presence of one or more microorganisms, one or more plant is selected based on one or more selection criterion. In one embodiment the plants are selected on the basis of one or more phenotypic traits. Skilled persons will readily appreciate that such traits include any observable characteristic of the plant, including for example growth rate, height, weight, colour, taste, smell, changes in the production of one or more compounds by the plant (including for example, metabolites, proteins, drugs, carbohydrates, oils, and any other compounds). Selecting plants based on genotypic information is also envisaged (for example, including the pattern of plant gene expression in response to the microorganisms, genotype, presence of genetic markers). It should be appreciated that in certain embodiments, plants may be selected based on the absence, suppression or inhibition of a certain feature or trait (such as an undesirable feature or trait) as opposed to the presence of a certain feature or trait (such as a desirable feature or trait).

Where the presence of one or more genetic marker is assessed, the one or more marker may already be known and/or associated with a particular characteristic of a plant; for example, a marker or markers associated with an increased growth rate or metabolite profile. This information could be used in combination with assessment based on other characteristics in a method of the disclosure to select for a combination of different plant characteristics that may be desirable. Such techniques may be used to identify novel QTLs which link desirable plant traits with a specific microbial flora—for example matching plant genotype to the microbiome type.

By way of example, plants may be selected based on growth rate, size (including but not limited to weight, height, leaf size, stem size, branching pattern, or the size of any part of the plant), general health, and survival, as well as other characteristic, as described herein before. Further non-limiting examples include selecting plants based on: speed of seed germination; quantity of biomass produced; increased root, and/or leaf/shoot growth that leads to an increased yield (herbage or grain or fibre or oil) or biomass production; effects on plant growth that results in an increased seed yield for a crop, which may be particularly relevant in cereal crops such as wheat, barley, oats, rye, maize, rice, sorghum, oilseed crops such as soybean, canola, cotton, sunflower, and seed legumes such as peas, beans; effects on plant growth that result in an increased oil yield, which may be particularly relevant in oil seed crops such as soybean, canola, cotton, jatropha and sunflower; effects on plant growth that result in an increased fibre yield (e.g. in cotton, flax and linseed) or for effects that result in an increased tuber yield in crops such as potatoes and sugar beet; effects on plant growth that result in an increased digestibility of the biomass which may be particularly relevant in forage crops such as forage legumes (alfalfa, clovers, medics), forage grasses (*Lolium* species; *Festuca* species; *Paspalum* species; *Brachiaria* species; *Eragrostis* species), forage crops grown for silage such as maize and forage cereals (wheat, barley, oats); effects on plant growth which result in an increased fruit yield which may be particularly relevant to pip fruit trees (such as apples, pears, etc), berry fruits (such as strawberries, raspberries, cranberries), stone fruit (such as nectarines, apricots), and citrus fruit, grapes, figs, nut trees; effects on plant growth that lead to an increased resistance or tolerance disease including fungal, viral or bacterial diseases or to pests such as insects, mites or nematodes in which damage is measured by decreased foliar symptoms such as the incidence of bacterial or fungal lesions, or area of damaged foliage or reduction in the numbers of nematode cysts or galls on plant roots, or improvements in plant yield in the presence of such plant pests and diseases; effects on plant growth that lead to increased metabolite yields, for example in plants grown for pharmaceutical, nutraceutical or cosmeceutical purposes which may be particularly relevant for plants such as star anise grown for the production of shikimic acid critical for the production of anti-influenza drug oseltamivir, or the production of Japanese knotweed for the extraction of resveratrol, or the production of soluble fibre and dietary enzyme products from kiwifruit, or for example increased yields of "condensed tannins" or other metabolites useful for inhibiting the production of greenhouse gases such as methane in grazing animals; effects on plant growth that lead to improved aesthetic appeal which may be particularly important in plants grown for their form, colour or taste, for example the colour intensity and form of ornamental flowers, the taste of fruit or vegetable, or the taste of wine from grapevines treated with microorganisms; and, effects on plant growth that lead to improved concentrations of toxic compounds taken up or detoxified by plants grown for the purposes of bioremediation.

Selection of plants based on phenotypic or genotypic information may be performed using techniques such as, but not limited to: high through-put screening of chemical components of plant origin, sequencing techniques including high through-put sequencing of genetic material, differential display techniques (including DDRT-PCR, and DD-PCR), nucleic acid microarray techniques, RNA-seq (Whole Transcriptome Shotgun Sequencing), qRT-PCR (quantitative real time PCR).

In certain embodiments of the disclosure, selection for a combination of plant traits may be desired. This can be achieved in a number of ways. In one embodiment, multiple rounds of iterative improvement for one trait, e.g. superior growth, are maintained until an acceptable level of growth is attained. Similar, but completely separate rounds of selection are undertaken to identify microorganisms that can confer at least different desirable traits, for example for improved flower colour. Such separate rounds of selection may be performed using an iterative or stacking approach or a combination of separate methods could be used, with the microorganisms that result from those separate rounds or methods being combined into a single composition. At this point the microorganism(s) could be developed into a product containing combinations of separately-fermented microorganisms each shown to improve a different plant attribute. In a further embodiment, the separately selected sets of microorganisms may be combined in sets of two or more and used in further methods of the disclosure. In another embodiment, the separately selected sets of microorganisms may be separated into individual isolates and then individual isolates combined in sets of two or more and used in further methods of the disclosure. In one embodiment, the combined microorganisms are applied to the plant and/or growth medium in the same iterative cycle. For example, in one combination, microorganisms able to improve plant growth are combined with microorganisms able to enhance flower colour. The combined microorganisms are then added to a plant growth medium in which the plants are grown for a suitable period, under suitable conditions. The degree of growth and flower colour is assessed and microbes are isolated from the best-performing plants for use in a succeeding iteration. Similar iterative rounds may be continued until an acceptable level of plant growth and flower colour is attained. This approach will aid the selection of microbes that synergistically improve plant performance; by way on non-limiting example, improve plant growth and flower colour to a degree better than that achieved if the microorganisms are applied simply as a combination of two separately-selected sets.

Harvesting

Following selection, one or more plants are harvested and plant tissues may be examined to detect microorganisms forming associations with the plants (for example, endophytic, epiphytic or rhizospheric associations).

The techniques described herein may be used in acquiring a second set of microorganisms at the conclusion of a method of the disclosure or for use in any successive repeat of the methods of the disclosure.

The one or more microorganisms may be isolated from any appropriate tissue of the plants selected; for example, whole plant, foliar tissue, stem tissue, root tissue, and/or seeds. In a embodiment, the microorganisms are isolated from the root tissue, stem or foliar tissues and/or seeds of the one or more plants selected.

In certain embodiments of the disclosure, the microorganisms may be acquired in crude form, in which they are not isolated from the source material in which they reside (such as plant tissue or growth media).

Where isolation of the microorganisms occurs, they may be isolated from the plants using any appropriate methods known in the art. However, by way of example, methods for isolating endophytic microbes may include the sterile excision of the plant material of interest (e.g. root, stem lengths, seed), surface sterilisation with an appropriate solution (e.g. 2% sodium hypochlorite), after which the plant material is placed on nutrient medium for microbial outgrowth, especially filamentous fungi. Alternatively, the surface-sterilised plant material can be crushed in a sterile liquid (usually water) and the liquid suspension, including small pieces of the crushed plant material spread over the surface of a suitable solid agar medium, or media, which may or may not be selective (e.g. contain only phytic acid as a source of phosphorus). This approach is especially useful for bacteria and yeasts which form isolated colonies and can be picked off individually to separate plates of nutrient medium, and further purified to a single species by well-known methods. Alternatively, the plant root or foliage samples may not be surface sterilised but only washed gently thus including surface-dwelling epiphytic microorganisms in the isolation process, or the epiphytic microbes can be isolated separately, by imprinting and lifting off pieces of plant roots, stem of leaves on to the surface of an agar medium and then isolating individual colonies as above. This approach is especially useful for bacteria and yeasts, for example. Alternatively, the roots may be processed without washing off small quantities of soil attached to the roots, thus including microbes that colonise the plant rhizosphere. Otherwise, soil adhering to the roots can be removed, diluted and spread out onto agar of suitable selective and non-selective media to isolate individual colonies of rhizospheric microbes. Further exemplary methodology can be found in: Strobel G and Daisy B (2003) Bioprospecting for microbial endophytes and their natural products. Microbiology and Molecular Biology Reviews 67 (4): 491-502; Zinniel D K et al. (2002) Isolation and characterisation of endophytic colonising bacteria from agronomic crops and prairie plants. Applied and Environmental Microbiology 68 (5): 2198-2208; Manual of Environmental Microbiology, Hurst et al., ASM Press, Washington D.C.

Methods for isolation may be informed by culture independent community profiling techniques that provide information on the identity and activity of microbes present in a given sample. These methods may include, but are not limited to, sequencing techniques including high throughput sequencing and phylogenetic analysis, or microarray-based screening of nucleic acids coding for components of rRNA operons or other taxonomically informative loci.

In embodiments of the disclosure where two or more microorganism are isolated from plant material and then separated into individual isolates, any appropriate methodology for separating one or more microorganism from each other may be used. However, by way of example, microbial extracts prepared from plant material could be spread on agar plates, grown at an appropriate temperature for a suitable period of time and the resulting microbial colonies subsequently selected and grown in an appropriate media (for example, streaked onto fresh plates or grown in a liquid medium). The colonies may be selected based on morphology or any other appropriate selection criteria as will be understood in the art. By way of further example, selective media could be used.

The one or more microorganisms may be harvested (including in isolated or crude form) from the plants (including the rhizosphere as described herein before) at any appropriate time point. In one embodiment they are harvested at any time after germination of the plant. For example, they can be isolated from the period shortly after germination (where survival in the first few days after germination is an issue, for example with bacterial and fungal root and collar rots), then at any stage after that, depending on the timing required for a plant to grow in order to evidence a discriminatory benefit that enables it's selection from the plant population (for example, to discriminate say the top 10 of 200 plants).

The inventor(s) has observed that different microorganisms may associate with a plant at different stages of the plant's life. Accordingly, harvesting a plant at different time points may result in selection of a different population of microorganisms. Such microorganisms may be of particular benefit in improving plant condition, survival and growth at critical times during its life.

In another embodiment of the disclosure, in the case of microorganisms that form an association with a plant that allows vertical transmission from one generation or propagule to the next (for example seed-endophytic or -epiphytic associations, or endophytic and epiphytic associations with plants/propagules multiplied vegetatively) the microorganisms may not be isolated from the plant(s). At the conclusion of a method of the disclosure, a target or selected plant itself may be multiplied by seed or vegetatively (along with the associated microorganisms) to confer the benefits) to "daughter" plants of the next generation or multiplicative phase. Similarly, where a successive repeat of the method is desired, plant material (whole plant, plant tissue, part of the plant) comprising the set of one or more microorganisms can be used in step a) of any successive repeat.

Stacking

The inventor(s) envisage advantages being obtained by stacking the means of selection (or the selection criteria) of plants in repeated rounds of the method of the disclosure. This may allow for acquiring a population of microorganisms that may assist a plant in having a number of different desirable traits, for example.

In this embodiment of the disclosure the one or more microorganisms acquired from the one or more plants selected, as previously described, is used in a second round or cycle of the method. In the first round, one or more plants may have been selected based on biomass. In the second round, one or more plants may be selected based on production of a particular compound. The microorganisms isolated from the second round of the method may then be used in a subsequent round, and so on and so on. Any number of different selection criteria may be employed in successive rounds of the method, as desired or appropriate.

In one embodiment, the selection criteria applied in each repeat of the method is different. However, in other embodiments of the disclosure, the selection criteria applied in each round may be the same. It could also be the same but applied at differing intensities with each round. For example, the selection criteria may be fibre levels and level of fibre required for a plant to be selected may increase with successive rounds of the method. The selective criteria may increase or decrease in successive rounds in a pattern that may be linear, stepped or curvilinear.

It should also be appreciated that in certain embodiments of the disclosure, where one or more microorganism(s) forms an endophytic or epiphytic relationship with a plant that allows vertical transmission from one generation or propagule to the next the microorganisms need not be isolated from the plant(s). At the conclusion of a method of the disclosure a target or selected plant itself may be multiplied by seed or vegetatively (along with the associated microorganisms) to confer the benefits) to "daughter" plants of the next generation or multiplicative phase. Similarly, where a successive repeat of the method is desired, plant material (whole plant, plant tissue, part of the plant) comprising the set of one or more microorganisms can be used in step a) of the successive repeat.

It should further be appreciated that two or more selection criterion may be applied with each iteration of the method.

Microorganisms and Compositions Containing Same

In addition to the methods described herein before, the disclosure relates to microorganisms selected, acquired, or isolated by such methods and compositions comprising such microorganisms. In its simplest form, a composition comprising one or more microorganisms includes a culture of living microorganism, or microorganisms in a live but inactive state(s), including frozen, lyophilised or dried cultures. However, the compositions may comprise other ingredients, as discussed below.

Thus, the disclosure provides, in some embodiments, for a composition comprising a microbial consortium that has been evolved to induce a beneficial property in a plant phenotypic trait.

The disclosure should also be understood to comprise methods for the production of a composition to support plant growth, quality and/or health or a composition to suppress or inhibit plant growth, quality and/or health, the method comprising the steps of a method herein before described and the additional step of combining the one or more microorganisms with one or more additional ingredients.

Skilled persons will readily appreciate the types of additional ingredients that may be combined with the one or more microorganisms, having regard to the nature of the composition that is to be made, the microorganisms to be used, and/or the method of delivery of the composition to a plant or its environment. However, by way of example, the ingredients may include liquid and/or solid carriers, microbial preservatives, microbial activators that induce specific metabolic activities, additives to prolong microbial life (such as gels and clays), wettable powders, granulated carriers, soil, sand, agents known to be of benefit to microbial survival and the growth and general health of a plant, peat, organic matter, organic and inorganic fillers, other microorganisms, wetting agents, organic and inorganic nutrients, and minerals.

Such compositions can be made using standard methodology having regard to the nature of the ingredients to be used. Compositions developed from the methods of the disclosure may be applied to a plant by any number of methods known to those skilled in the art. These include for example: sprays; dusts; granules; seed-coating; seed spraying or dusting upon application; germinating the seed in a bed containing suitable concentrations of the composition prior to germination and planting out of the seedlings; prills or granules applied next to the seed or plant during sowing or planting, or applied to an existing crop through a process such as direct drilling; application to plant cuttings or other vegetative propagules by dipping the cut surface or the propagule into liquid or powdered microbial substrate prior to planting; application to the soil as a "soil treatment" in the form of a spray, dust, granules or composted composition that may or may not be applied with plant fertilisers prior to or after sowing or planting of the crop; application to a hydroponic growth medium; inoculation into plant tissues under axenic conditions via injection of compositions or otherwise inoculated via a cut in such tissues, for the subsequent establishment of an endophytic relationship with the plant that extends to the seed, or propagative tissues, such that the plant can be multiplied via conventional agronomic practice, along with the endophytic microbe providing a benefit(s) to the plant.

In one embodiment, the disclosure provides a composition comprising one or more of the microorganisms listed in table 4. In another embodiment, the disclosure provides a composition comprising one or more microorganisms listed in table 3. In another embodiment, the disclosure provides a composition comprising one or more microorganisms listed in table 2.

In embodiments, the disclosure provides for a microbial consortium that contains at least one microbial species selected from the group consisting of: a member of the microorganisms of table 4, a member of the microorganisms of table 3, a member of the microorganisms of table 2, and combinations thereof.

Disjunctive Associations

In one aspect, the disclosure provides for methods of assembling disjunctive microbial communities that are not associated with one another in a natural setting. That is, the present method is capable of assembling microbial communities, or consortia, whose normal presence in a system would not bring the bacteria into close association with one another. In some aspects, the microbes are naturally located in physically remote locations from one another. In other aspects, the microbes may be located very close to one another physically, but they inhabit different ecological niches that prevent their close association. Thus, by utilizing the methods of the present disclosure, one is able to constructively bring together microbial species into close associations that are not naturally occurring.

In an embodiment, the methods of the present disclosure are able to identify at least one microbial species that is not normally associated with a plant community in a natural setting; whereby, when the microbial species is brought into association with the plant the microbial species' abundance increases disproportionately greater than the abundance of other microbial species.

Consequently, the present methods are able to identify "invasive" microbial species that when brought out of their normal ecological habitat and associated with a plant and substrate of interest, perform better than microbial species that are "native" to the plant or substrate in question.

In a particular embodiment, the at least one microbial species that is identified to perform better than expected, when associated with a plant of interest, is able to help the plant acquire a phenotypic trait of interest, e.g. biomass increase, sugar content, photosynthetic efficiency, water retention, growth on nutrient poor soils, etc.

Thus, by identifying microbes that are able to thrive outside of their natural ranges when associated with a particular plant and/or substrate of interest, the present disclosure can harness the ability of a microbe to be free from its coevolved constraints (e.g. from predators, landscape, nutrient constraints, etc.) and beneficially use that release on the microbe's population dynamics to increase a phenotypic trait of interest in the plant.

The present disclosure has discovered that microbes taken from their natural habitat and placed into association with a plant and/or substrate not normally encountered in their native range are able to increase their abundance disproportionately more than the microbial assemblages presently associated with said plants and/or substrates. The mechanism of this microbial increase may be the ability of the microbes to outcompete the resident assemblages. The microbes may also benefit from association with the plant in a symbiotic way that the resident assemblages do not. Whatever the particular mechanism involved, the present disclosure provides a method to harness the tremendous amount of microbial diversity present in the world's ecological regions and bring that diversity to bear on increasing desirable plant phenotypic traits.

Disparate Geographic Locations

In particular embodiments, the microbial community assemblages derived by the present methods are not naturally found in association with a particular plant and/or substrate. In some aspects, the microbial species forming the microbial community are all from the same geographic location. In other aspects, each microbial species forming the microbial community is from a different geographic location. A geographic location can be defined based upon the predominant soil type in a region, the predominant climate in a region, the predominant plant community present in a region, the distance between regions, the average rainfall in a region, among others.

In a particular embodiment, at least one microbial species that is a member of the microbial community derived by the disclosed method is native to, or was acquired from, a geographic region at least about: 1 m, 10 m, 100 m, 1 km, 10 km, 100 km, 1000 km, 10,000 km, 20,000 km, 30,000 km, or 40,000 km, from the location of the plant upon which a phenotypic trait is to be increased based upon the taught methods.

Genetically Modified Plants

In an aspect of the disclosure, methods are taught in which the microbial communities produced herein are associated with increasing the phenotypic response of a genetically altered plant.

For example, various plants have been genetically associated with commercial chemistries. Often, these genetic alterations enable the plant to be tolerant of the commercial chemical product, e.g. glyphosate resistance. Also, some plants have been genetically engineered to produce toxins that repel pests, e.g. plants producing *Bacillus thuringiensis* toxins.

The present disclosure provides a method to create beneficial microbial consortia that are correlated to improving a phenotypic trait of a genetically modified plant. The genetically modified plant may be modified to tolerate a particular chemical product (or products in the case of "stacked" chemical resistance) and/or may be genetically modified to produce a toxin. The present disclosure enables practitioners to improve a phenotypic trait of interest in these genetically modified plants by deriving microbial consortia that are tailored to the genetically modified plants environment. For example, glyphosate resistant plant communities inhabit particular ecological conditions. Farmers growing these crops often employ no tillage systems, as the need to constantly till the soil for weed eradication is alleviated by the ability to directly spray glyphosate on the crops. The microbes that inhabit these types of systems will be confronted with much different ecological parameters than a microbe that was found in a traditional tillage agriculture system where the level of physical disturbance would be high and repetitive. The methods taught herein enable the creation of microbial assemblages specifically adapted to the resident plant and its environment.

Methods of Producing Alternative Compositions

When microorganisms are cultured they may produce one or more metabolites, which are passed into the media in which they reside. Such metabolites may confer beneficial properties to plants.

Accordingly, the disclosure also provides a method for selecting or producing a composition capable of imparting one or more beneficial property to a plant, for example to support plant growth, quality and/or health, or for example to suppress or inhibit growth, quality and/or health of a plant, or to identify microorganisms that are capable of producing such a composition. In one embodiment, the composition is substantially free of microorganisms.

In one embodiment, the method is for the selection of a composition capable of imparting one or more beneficial property to a plant and comprises at least the steps of:
  a) culturing one or more microorganism selected by a method as herein before described in one or more media to provide one or more culture;
  b) separating the one or more microorganism from the one or more media after a period of time to provide one or more composition substantially free of microorganisms;
  c) subjecting one or more plant (including for example seeds, seedlings, cuttings, and/or propagules thereof) to the one or more composition from step b);
  d) selecting one or more composition of step c) if it is observed to impart one or more beneficial property to the one or more plants.

In another embodiment, the method is for the selection of a composition which is capable of imparting one or more beneficial property to a plant and comprises the steps of:
  a) culturing one or more microorganisms selected by a method of the first aspect of the disclosure in one or more media to form one or more culture;
  b) inactivating the one or more culture of step a) to provide one or more composition containing one or more inactivated microorganisms;
  c) subjecting one or more plant (including for example seeds, seedlings, cuttings, and/or propagules thereof) to the one or more composition of step b);
  d) selecting one or more composition from step c) if it is observed to impart one or more beneficial property to the one or more plants.

In one embodiment the method is for the selection of one or more microorganisms which are capable of producing a composition which is capable of imparting one or more beneficial property to a plant and comprises at least the steps of;
  a) culturing one or more microorganism selected by a method of the first aspect of the disclosure in one or more media to provide one or more culture;
  b) separating the one or more microorganism from the one or more media in the one or more culture from step a) after a period of time to provide one or more composition substantially free of microorganisms;
  c) subjecting one or more plant (including for example seeds, seedlings, cuttings, and/or propagules thereof) to the one or more composition from step b);
  d) selecting the one or more microorganisms associated with (or in other words used to produce the) one or more composition observed to impart one or more beneficial property to the one or more plants.

Another method of the disclosure comprises at least the steps of:
  a) culturing one or more microorganism in one or more media to provide one or more culture;
  b) separating the one or more microorganism from the one or more media in the one or more culture after a period of time to provide one or more composition substantially free of microorganisms;
  c) subjecting one or more plant (including for example seeds, seedlings, cuttings, and/or propagules thereof) to the one or more composition of step b);
  d) selecting the one or more microorganisms associated with (or in other words used to produce the) one or more composition observed to impart one or more beneficial property to the one or more plants; and,
  e) using the one or more microorganisms selected in step d) in step a) of a method of the first or eighth (and/or related) aspects of the disclosure.

In one embodiment of the methods of the previous two paragraphs, step b) of the methods could be substituted with the step of b) inactivating the one or more culture of step a) to provide one or more composition containing one or more inactivated microorganisms, and then using this composition in step c) of the process.

The microorganisms can be inactivated, fixed, killed or destroyed using any appropriate techniques know in the art. However, by way of example, one may use chemical agents and/or physical means to do so. In one embodiment, the cells are lysed. In another embodiment, cells are fixed by chemical means, so as to render the organisms non-viable, but retaining their structural integrity.

In certain embodiments of these methods, the microorganisms are cultured in two or more (preferably a large number, for example, from at least approximately 10 to up to approximately 1000) mixed cultures using media that can support the growth of a wide variety of microorganisms. Any appropriate media known in the art may be used. However, by way of example, growth media may include TSB (tryptic soy broth), Luria-Bertani (LB) broth, or R2A broth. In another embodiment, selective or enrichment media which are able to support the growth of microorganisms with an array of separate but desirable properties may be used. By way of example, the enrichment media referred to elsewhere herein may be used.

The microorganisms may be cultured in the media for any desired period. Following culture, the microorganisms are separated from the media and stored for later use. A separate composition also results. One or more plants in a suitable growth medium are then subjected to the composition (using any known methodology, or methodology as described herein before). After a period of time, growth of plants is assessed and plants selected (as described herein before, for example). Plants are preferably selected on the basis of size. However, other selection criteria as referred to herein may be used.

In one embodiment, the microorganism(s) producing the subset of compositions associated with the selected plants are recovered from storage. Two or more separate cultures of the microorganisms may then be mixed together and separated into two or more sub-cultures grown in two or more different media. This process can be repeated iteratively as many times as is deemed efficacious, with progressive steps refining down to fewer media and a narrower diversity of microorganisms until a desirable effect on the growth plants is achieved with a mixture of microbes that can be identified, grown and stored indefinitely as a standard starting inoculum for the production the composition.

Thus, in some embodiments, a microbial consortium is produced contains microbes that work together for the common function of promoting or inducing a plant to express particular phenotypic trait of interest.

Compositions and consortium produced by the disclosure may be used or formulated on their own or combined with one or more additional ingredients.

It should be appreciated that the general methodology described may be applicable to this aspect of the disclosure, including but not limited to growth media, plants, microorganisms, timing, iterative processing, and combinations thereof.

Additional System Based Methodology

The following methodology may be applied to a method of the disclosure for identifying one or more microorganisms as aforementioned.

FIG. 1 shows a system 10 according to an embodiment of the disclosure. System 10 includes requestors 11, request processor 12, growing facility 13, database or library 14 and depository 15.

Figure 2:
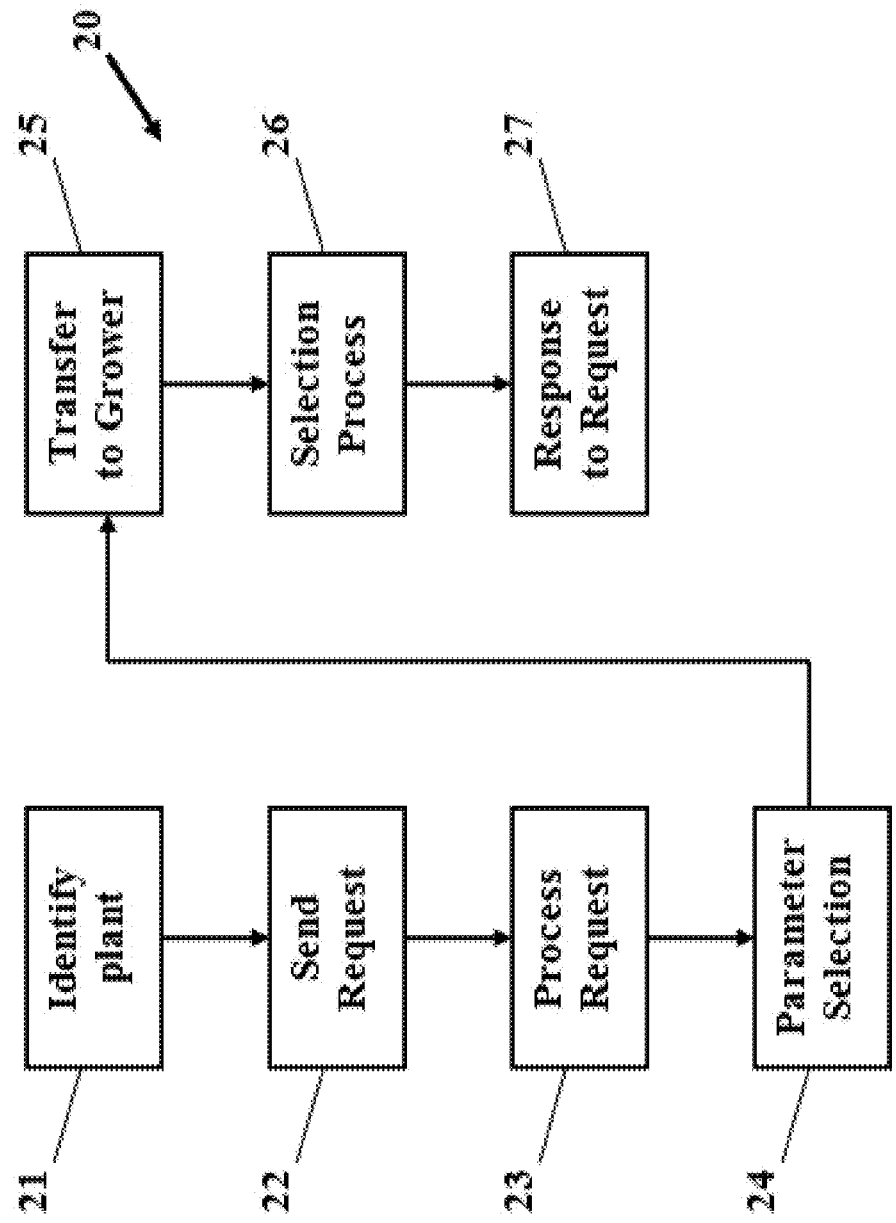
FIG. 2: shows the process flow of a method of an embodiment of the disclosure.
Figure 3:
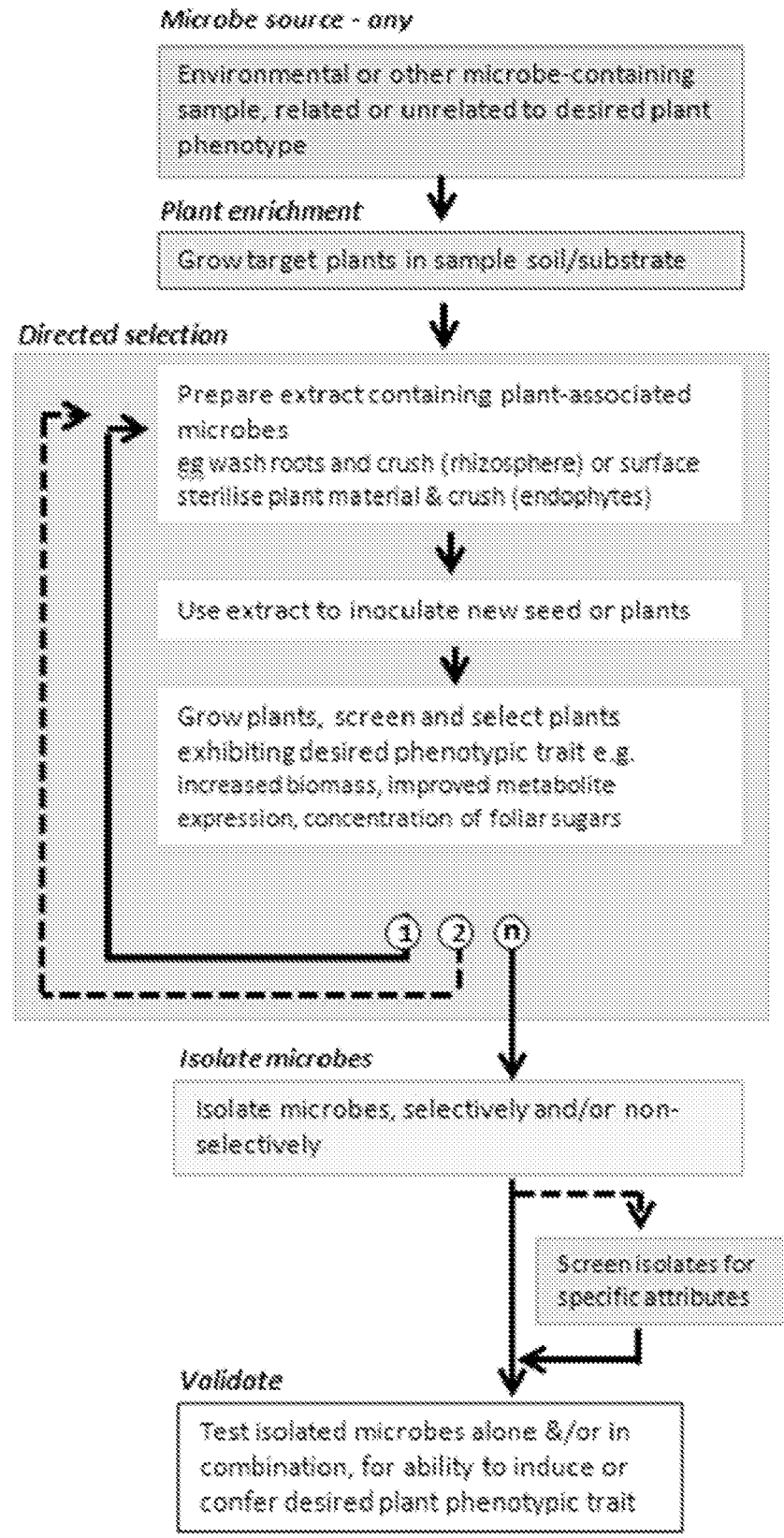
FIG. 3: shows a generalized process schematic of a disclosed method of accelerated microbial selection, also referred to herein as directed microbial selection. When the process is viewed in the context of a microbial community, the schematic is illustrative of a process of directed evolution of a microbial community.
Figure 4:
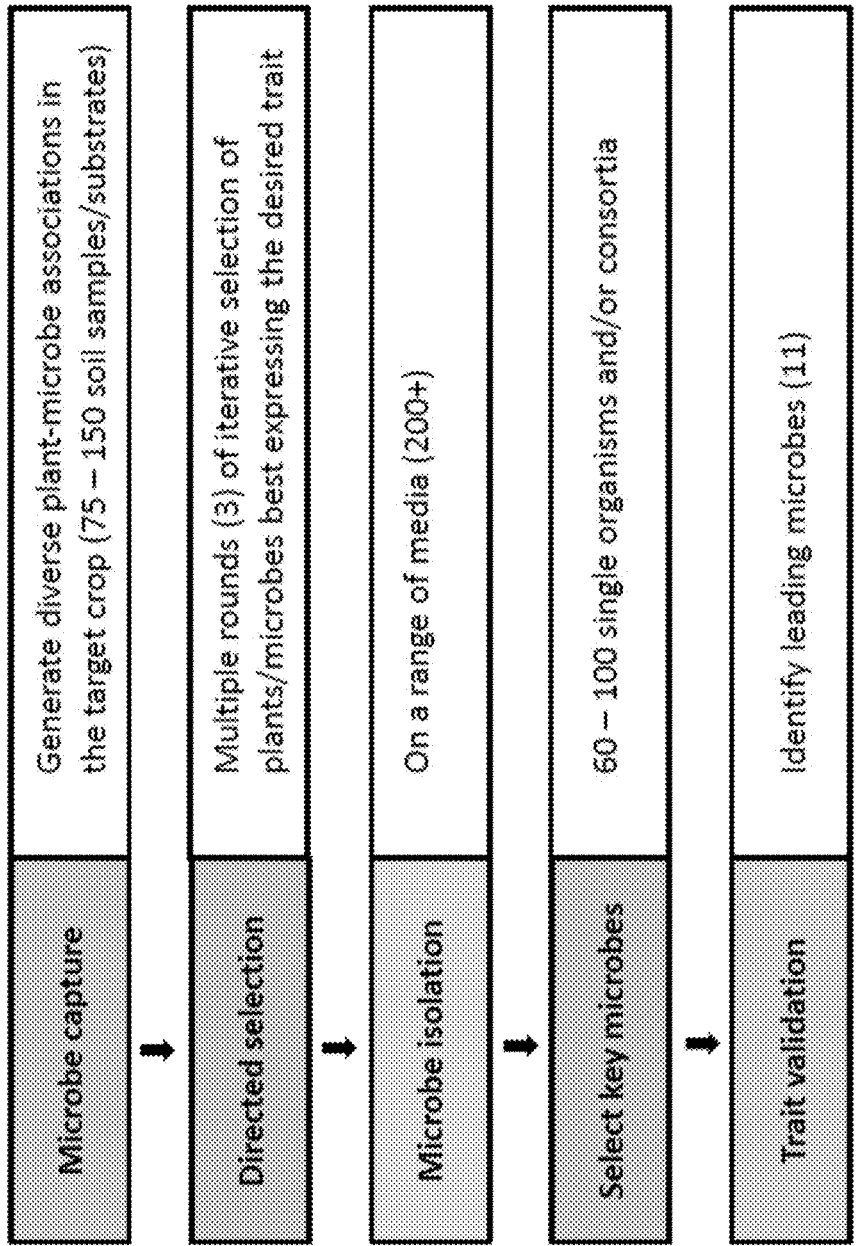
FIG. 4: shows a generalized process flow chart of an embodiment of the taught methods.
Figure 5:
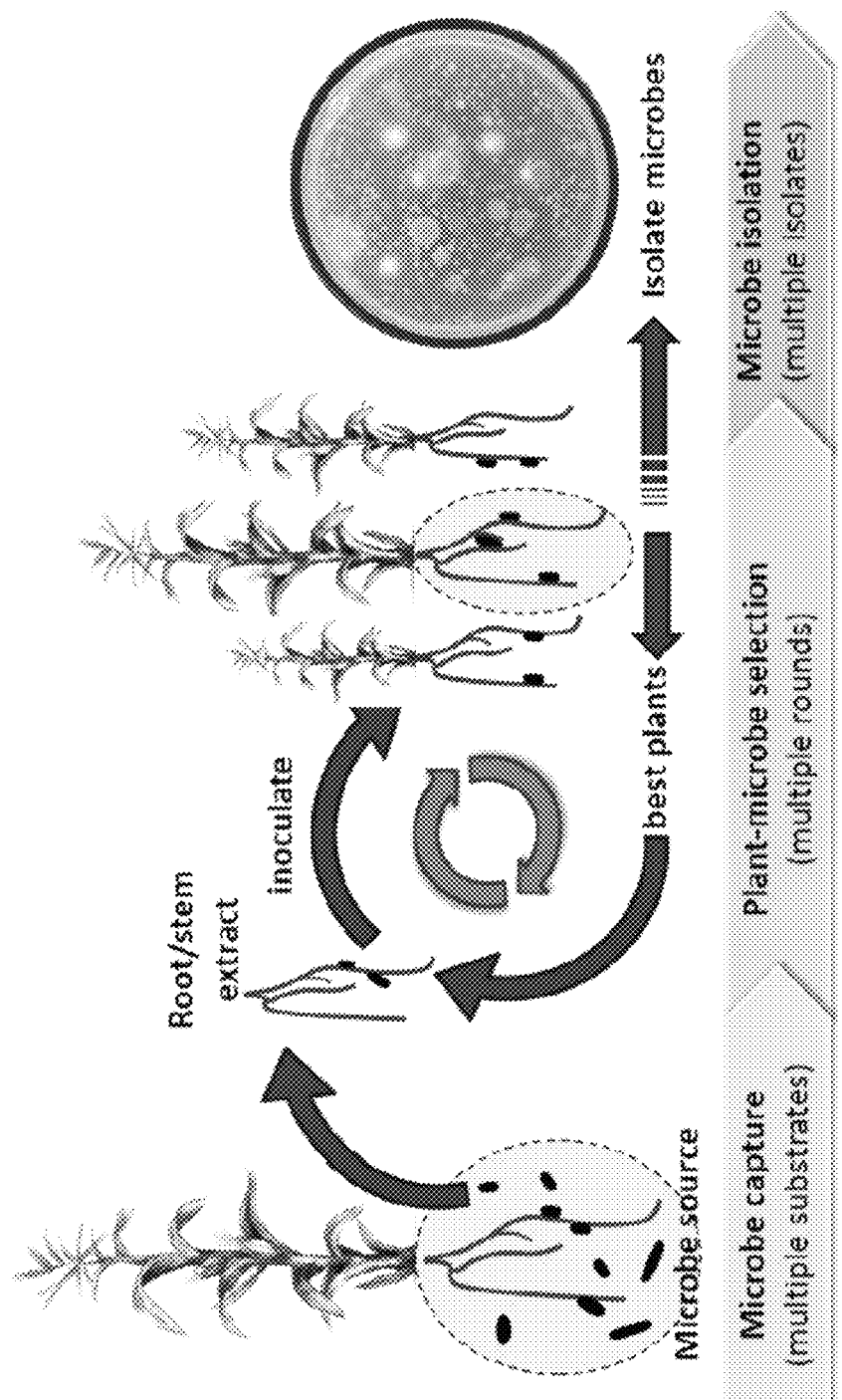
FIG. 5: shows a graphic representation and associated flow chart of an embodiment of the disclosed methods.
Figure 6:
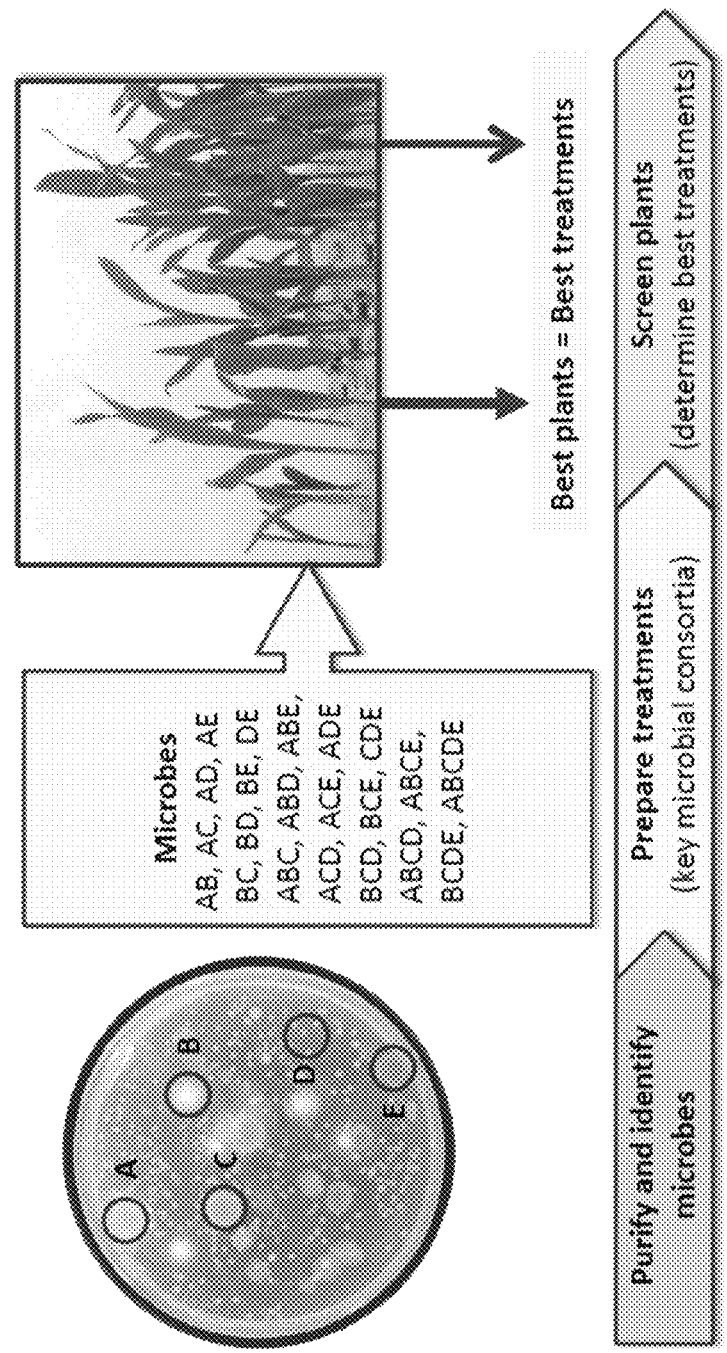
FIG. 6 shows a graphic representation and associated flow chart of an embodiment of the disclosed methods. The figure illustrates the ability to evolve microbial communities and selection of consortia for imparting a desirable phenotypic trait in a plant.
Figure 7:
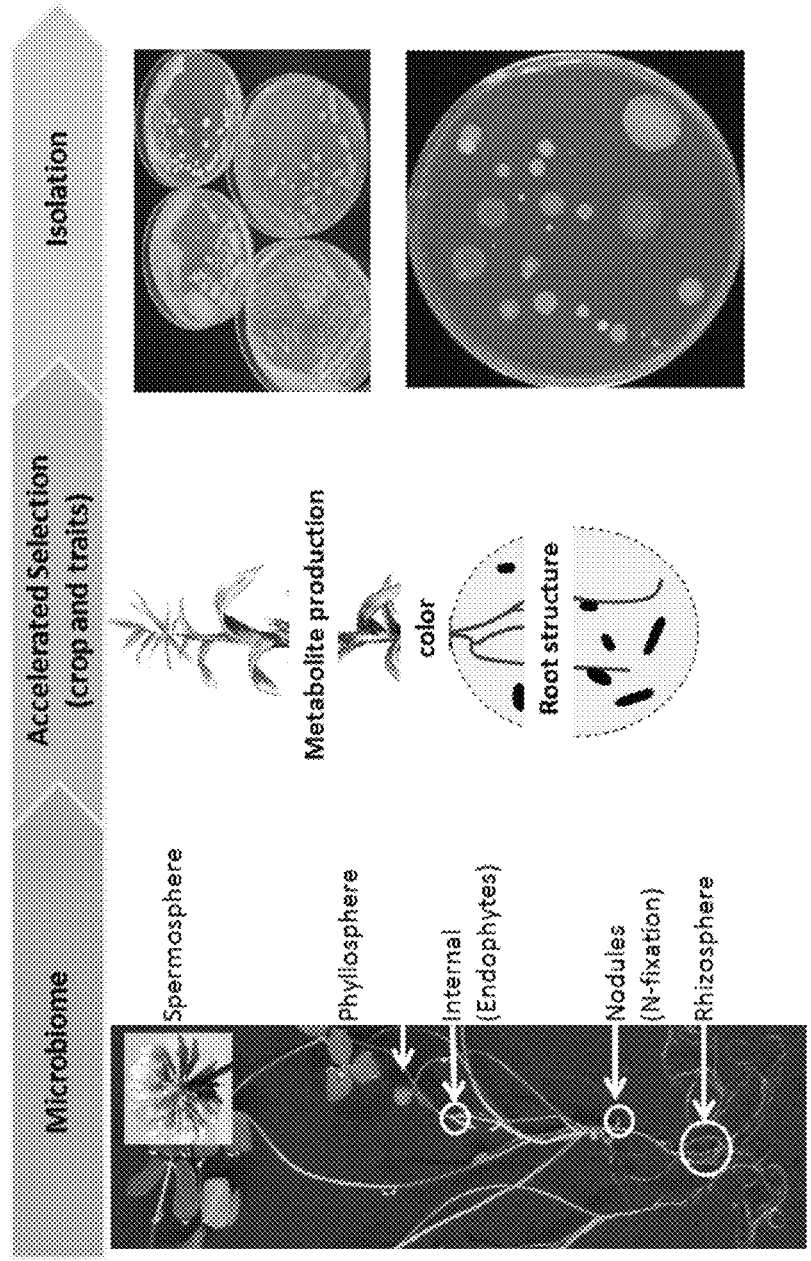
FIG. 7: shows a graphic representation and associated flow chart of an embodiment of the disclosed methods and illustrates that the methods can utilize microbes from a variety of sources (including multiple locations from a single plant) and can select microbes that help develop a myriad of plant phenotypic traits.
Figure 8:
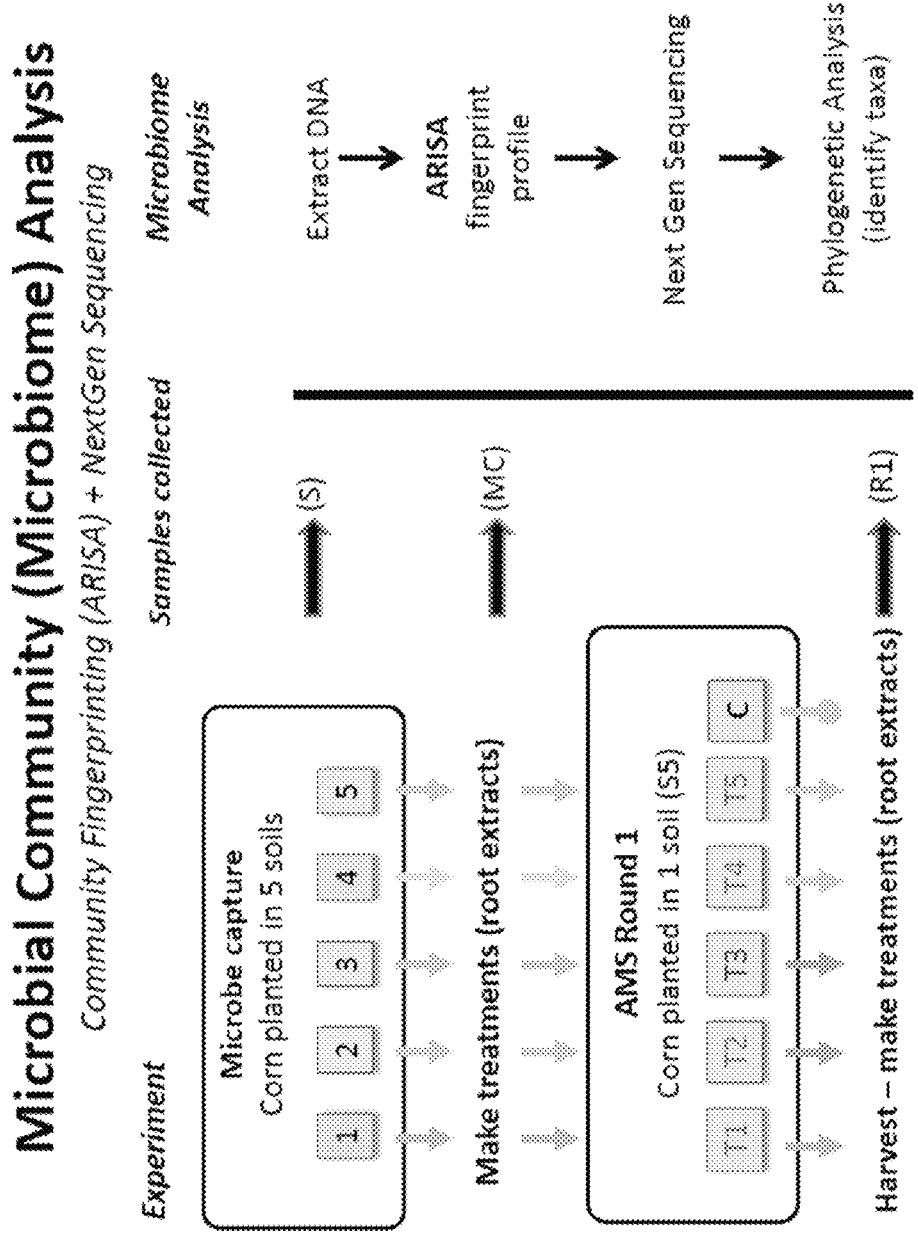
FIG. 8: shows a process of microbial community (microbiome) analysis utilizing community fingerprinting (ARISA)+NextGen Sequencing.
Figure 9:
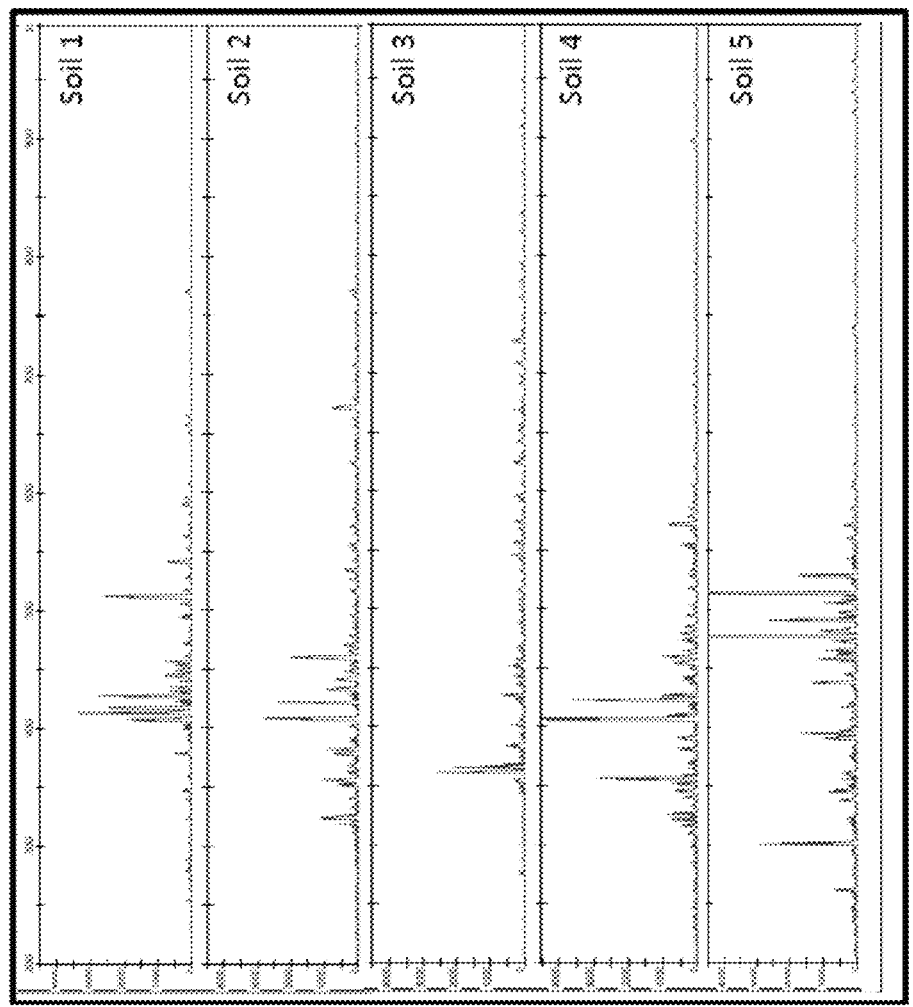
FIG. 9: shows ARISA microbial community fingerprinting of the microbial communities in 5 different soils. The operational taxonomic units (OTU) identified in each soil by NextGen sequencing are given.
Figure 10:
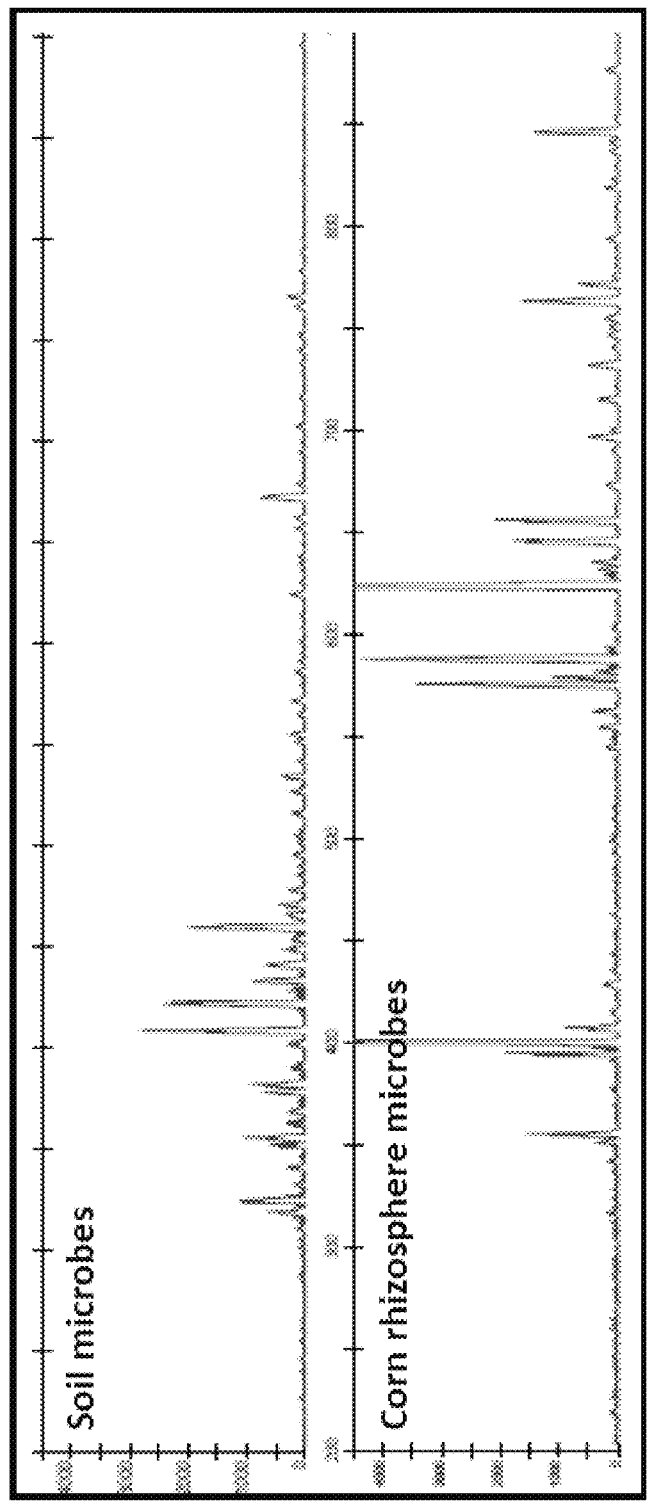
FIG. 10: shows ARISA microbial community fingerprinting of a soil sample and the rhizosphere community of a corn seedling grown in the same soil. The figure illustrates that a plant (i.e. corn) can amplify microbes present in its surroundings.
Figure 11:
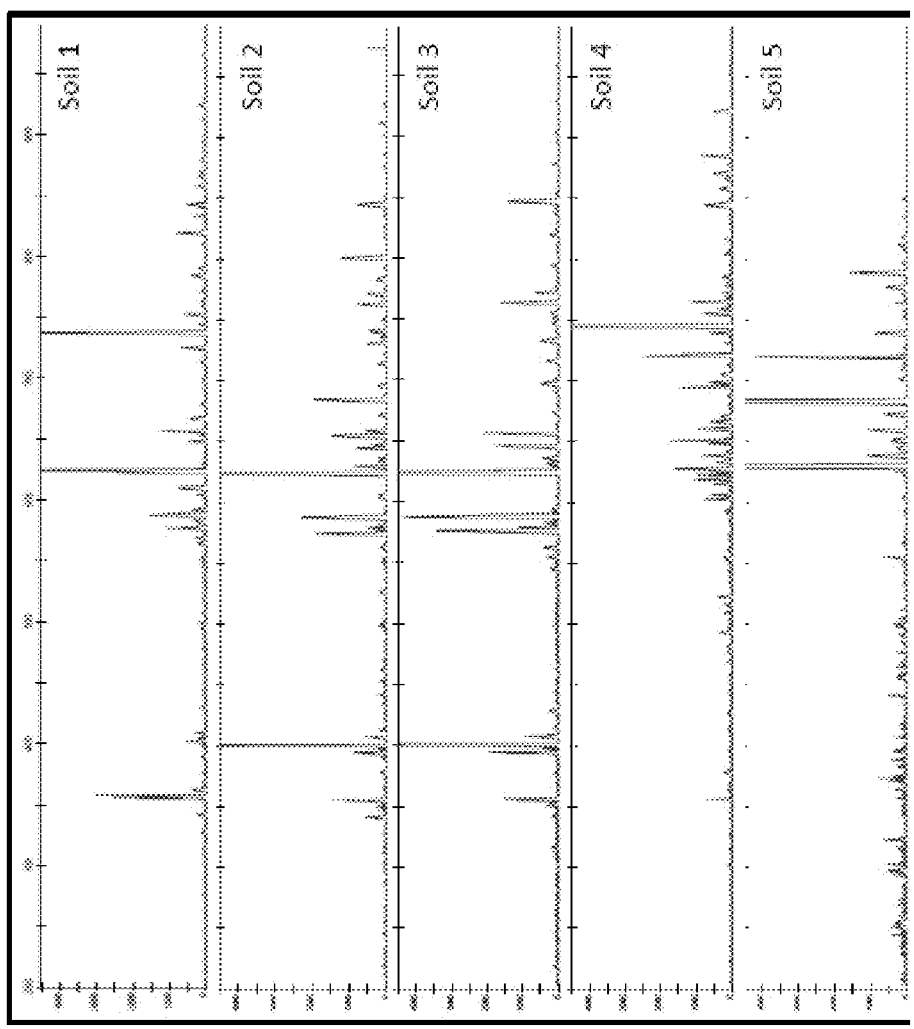
FIG. 11: shows ARISA microbial community fingerprinting across 5 soil types that have corn plants grown therein. The figure illustrates that a plant (i.e. corn) can "capture" different microbes depending upon the soil it is growing within.
Figure 12:
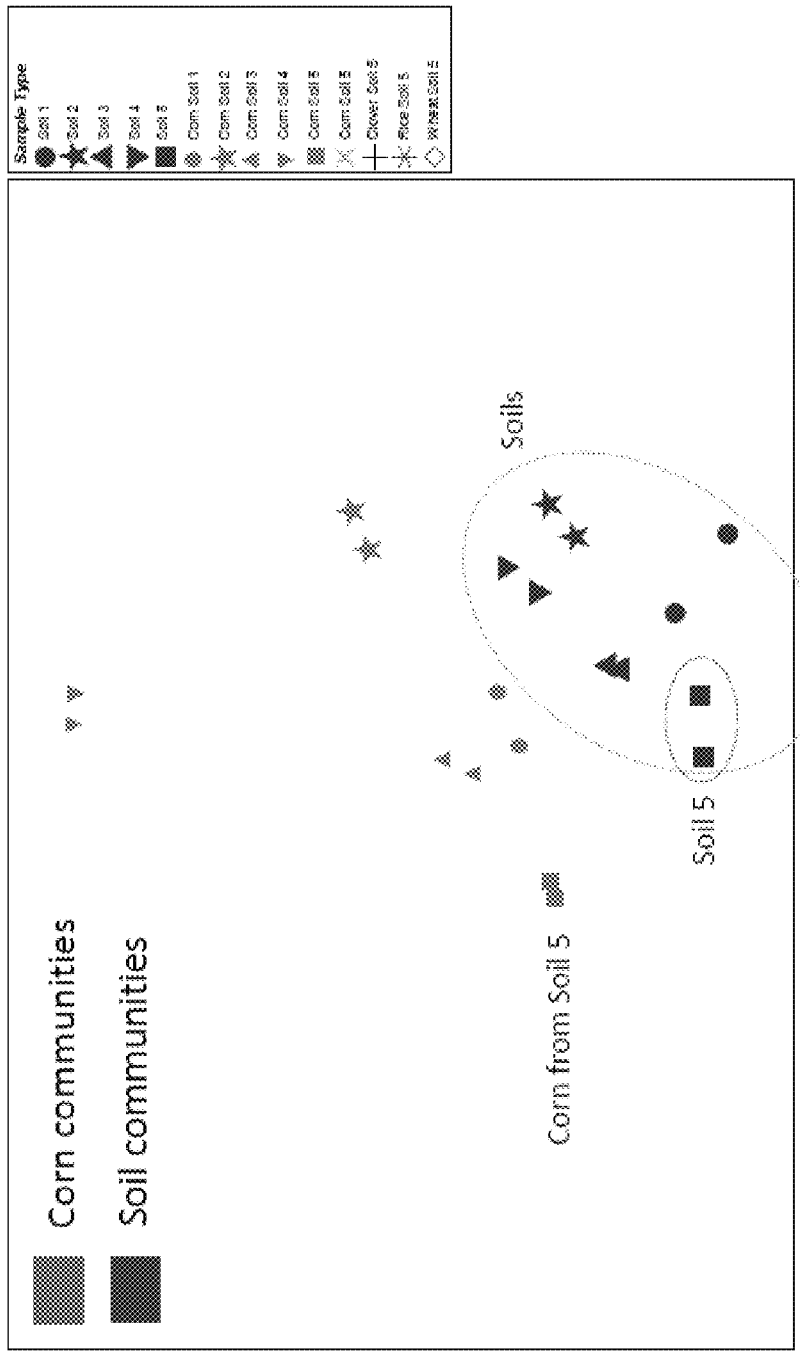
FIG. 12: shows the degree of similarity of the microbial communities associated with 5 soil types, and with or without the same variety of corn growing in each of the soils. The graphic illustrates that the microbial communities associated with the corn plants are distinct from the microbial communities with no corn across all 5 soil types. Thus, the methods disclosed herein are able to select for distinct microbial populations by utilizing a step of selecting for particular plants.
Figure 13:
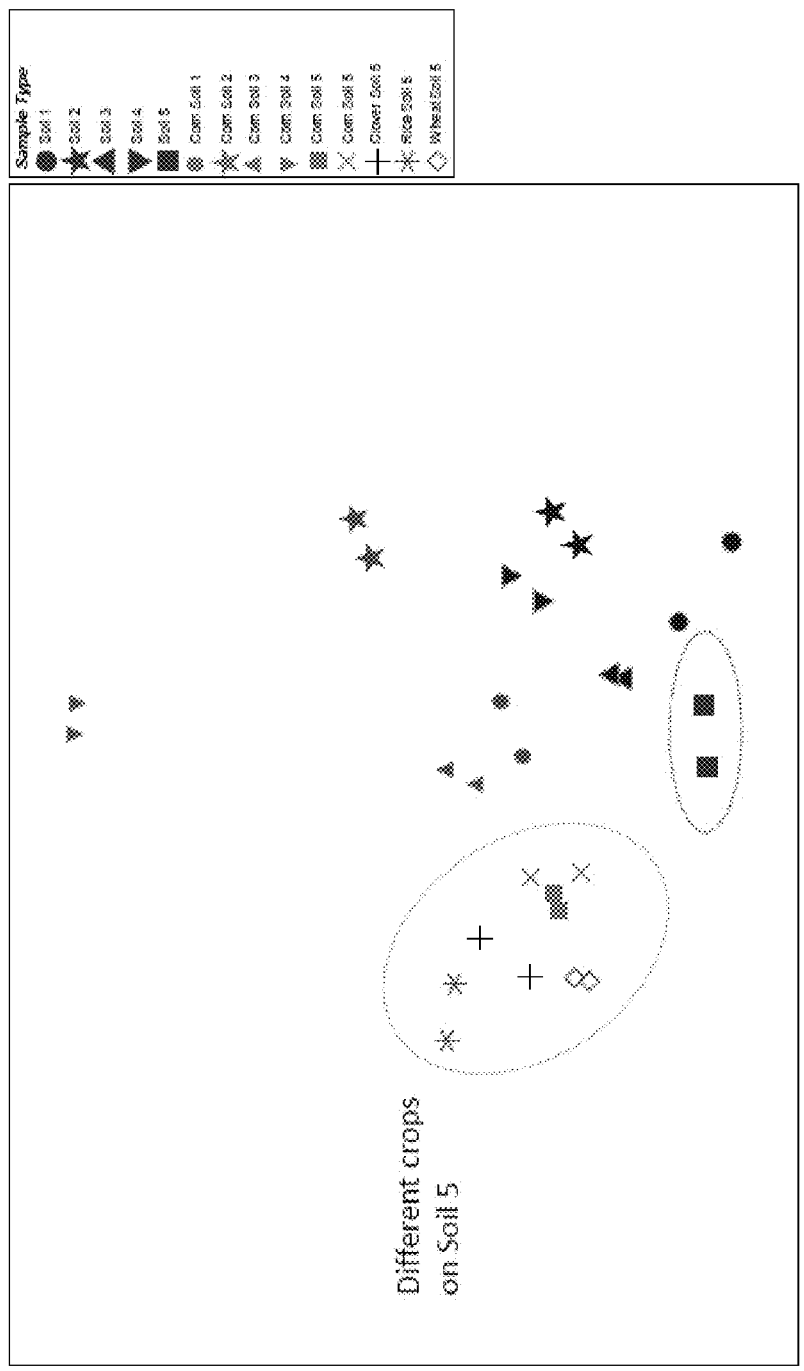
FIG. 13: shows the degree of similarity of the microbial communities associated with multiple crop types all grown within the same soil type. The graphic also shows the microbial communities associated with the single soil type with no crops grown therein. The graphic illustrates that the microbial communities associated with soils with no plants grown therein are different from those with plants growing therein. Further, each plant type can be seen to "capture" a particular community of microbes.
Figure 14:
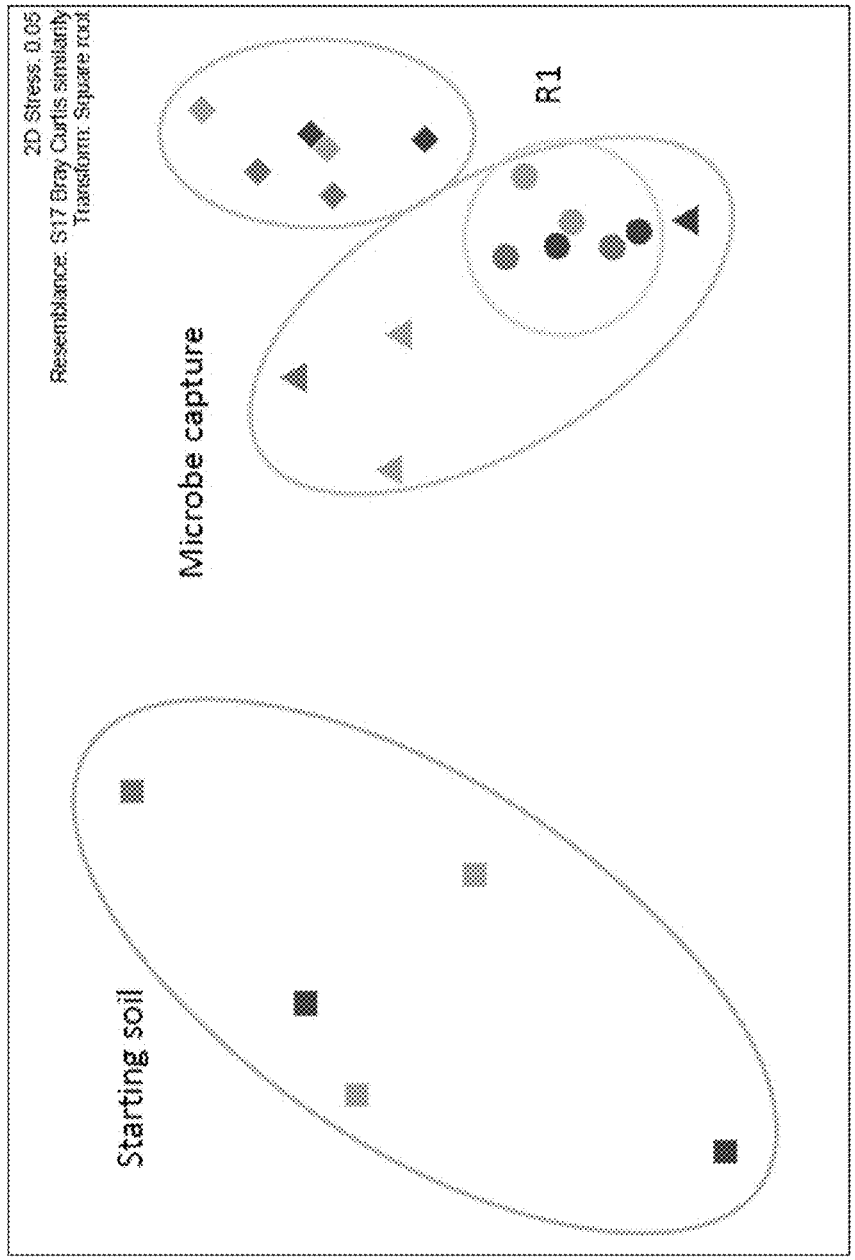
FIG. 14: shows NextGen Sequencing microbial community data that illustrates that the corn microbiome has changed after one round of accelerated microbial selection, also termed directed selection of microbes "DSM". The graphic shows the starting soil microbial community, the microbial community after "capture", and the microbial community after one round of selection (R1) according to the taught methods. Colored squares=communities identified in soil samples. Each color represents a different soil sample. Red symbols correspond to soil sample 5, as indicated in the experiment design graphic (i.e.
Figure 15:
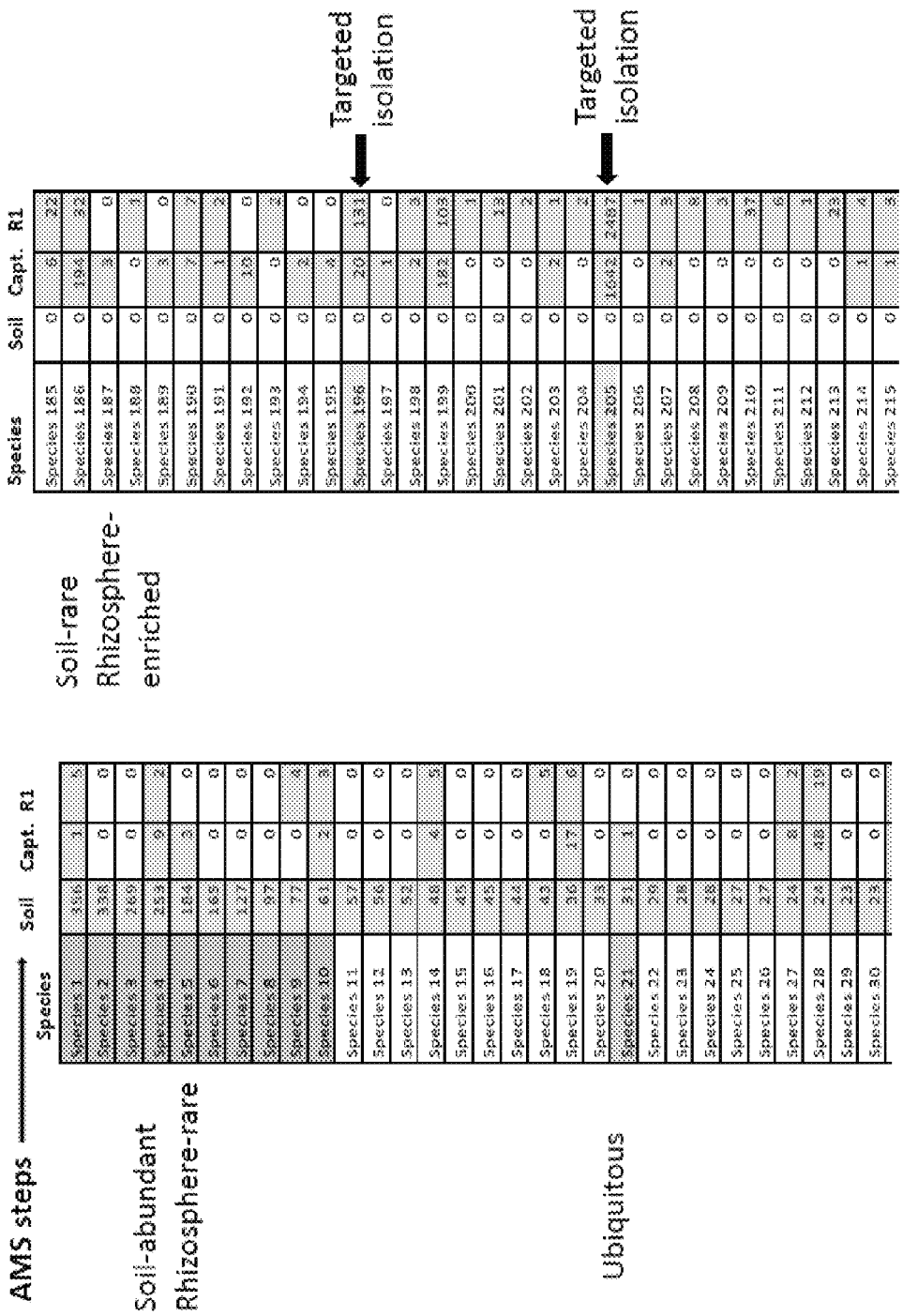
FIG. 15: shows that the methods of the disclosure drive dynamic change in relevant microbial abundance. The columns illustrate microbial abundance for the natural soil, microbial abundance after capture, and microbial abundance after Round 1 of a method as taught (R1). As can be seen, a microbial species that is normally ubiquitous in the soil "Species 21" is brought to below a detectable abundance level after R1. Also, "Species 205" that was not at a detectable abundance level in the natural soil is brought to an abundance of 1642 after the capture step and an abundance of 2487 after R1. Further, the methods also brought "Species 196" up from below detectable limits in natural soil to 131 after R1.
Figure 18:
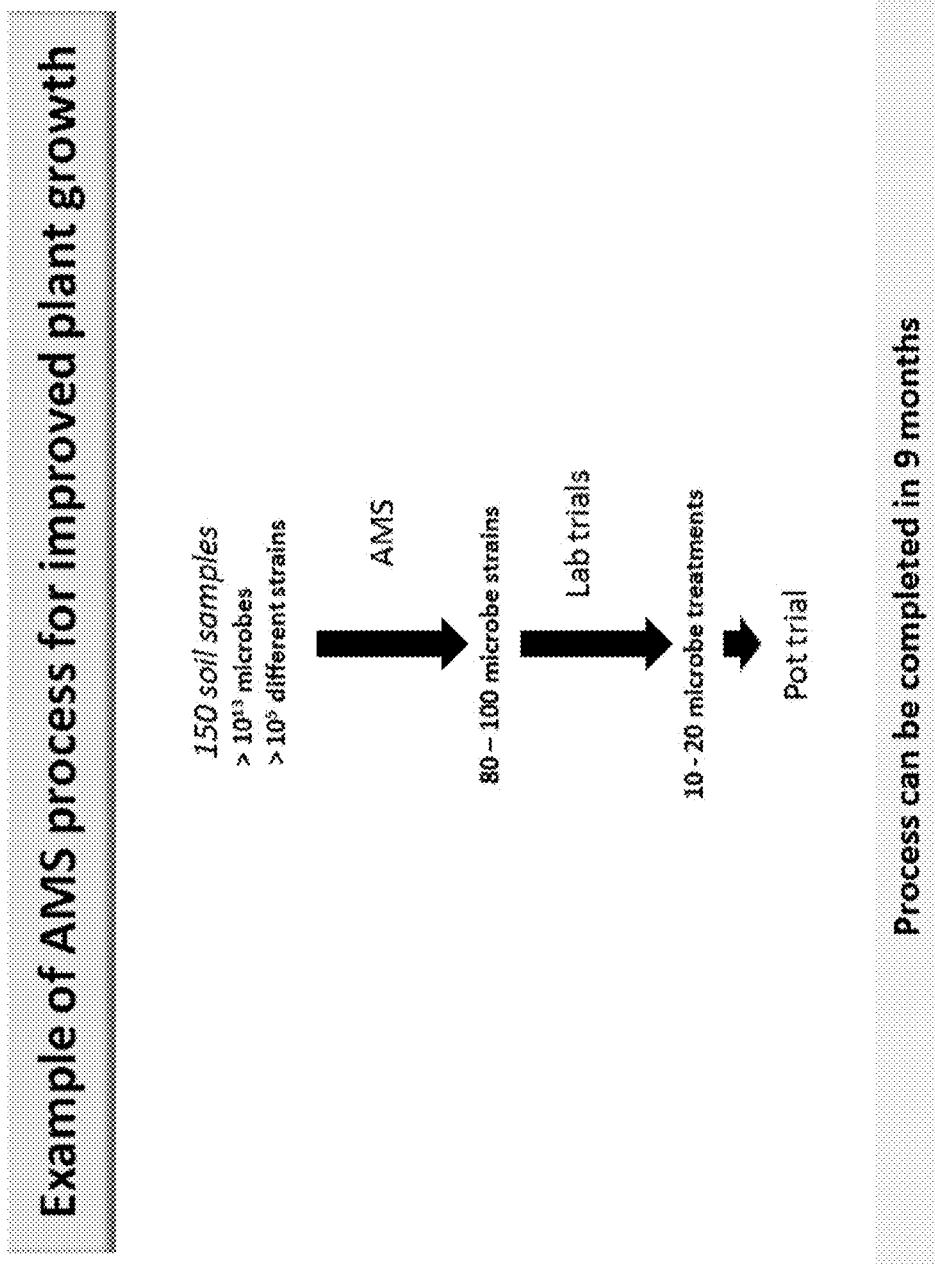
FIG. 18: is an overview of an experimental protocol implementing an accelerated method of microbial selection to improve the growth of a plant in 9 months.

FIG. 2 provides a flow chart illustrating a method 20 according to an embodiment of the disclosure. The steps shown in FIG. 2 will be described with reference to the system 10 shown in FIG. 1.

This system aspect of the disclosure is described in terms of identifying one or more microorganism that may impart one or more desired properties to one or more plants, with particular reference to the first, or eighth (and/or related) aspects of the disclosure. However, it should be appreciated that it is equally applicable to the identification of one or more compositions that may impart one or more desired property to one or more plant, or one or more microorganism that produces a composition that may impart one or more desired property to one or more plant, as herein before described, and summarised in the seventh (and/or related) and eighth (and/or related) aspects of the disclosure. Accordingly, unless the context requires otherwise, when describing the embodiments of the disclosure in this section of the specification, reference to the first aspect of the disclosure should be taken to also include reference to the seventh (and/or related) and eighth (and/or related) aspects of the disclosure, and reference to one or more microorganism should be taken to include reference to one or more composition.

The method begins at step 21 with a requestor 11 identifying a plant (or a class or group of plants). Reasons why particular plants or types of plants may be identified will be apparent to those skilled in the art. However, by way of example, it may have been found that a plant noted in general for having a high growth rate is growing at lower rates or not at all, there may simply be a desire to improve on existing growth rates or there may be a desire to introduce a plant to a different climate/environment/geographical region. The disclosure is not limited to conferring improvements to particular plant(s) and may be used to inhibit growth or otherwise adversely affect the plant(s).

At step 22, the requestor 11 sends the plant and/or the identity thereof to a request processor 12. The requestor 11 may provide further relevant information such as why or what properties they are seeking to improve. While only one request processor 12 is shown, it will be appreciated that more than one may be provided in the system 10.

Where a requestor 11 identifies a class or group of plants, more than one plant variety may be evaluated. Alternatively or additionally, selection of a one or more plant variety may be made elsewhere within the system 10 based on the group or class identified, including following evaluation of different varieties including using different microorganisms in accordance with methods of the disclosure.

Requests may conveniently be received over the internet via a web browser, although the disclosure is not limited thereto. Use of a web browser may additionally or alternatively be used to enable a requestor 11 to view reports on the progress being made in response to their request. For example, measures of growth may be provided.

At step 23, the request processor 12 receives and processes the request, essentially by initiating the performance of the method for the selection of one or more microorganism according to the first aspect of the disclosure. Note that the request processor 12 may or may not actively perform the method of the first aspect, or may only perform parts thereof.

According to particular embodiments, the request processor 12 may act as an intermediary or agent between the requestor 11 and the parties able to perform the method of the first aspect. Also, different arrangements may be made in response to different requests. For example, for one request, the environment around the request processor 12 may be suitable for evaluating a particular plant but unsuitable for another, requiring the assistance of a third party facility. This could be due to a desire to test in a particular soil type, altitude or climate. Other factors will also be apparent although it is appreciated that "artificial" environments may be used. Furthermore, varying degrees of user interaction may take place at the request processor 12. According to one embodiment, a computer processor selects parameters or conditions for a study based on data input by a requestor 11. As will be appreciated, providing a structured information request may help to effect this, and where necessary, reference may be made to databases including database 14.

At step 24, parameters of the evaluation process are selected. For example, reference may be made to database 14 for microorganisms that may provide the desired improvement in the plant(s). While little data to date has been provided in the art on microorganisms having beneficial associations with particular plant varieties, this will be improved upon through ongoing operation of the methods of the disclosure and stored in database 14. Other parameters such as plant type(s) and environmental conditions may also be selected.

At step 25, the request (or portions thereof) and evaluation parameters are sent to growing facility 13 which may obtain suitable microorganisms from depository 15. These may or may not have been previously identified. While only one growing facility 13 and one depository 15 are shown, it will be appreciated that the disclosure is not so limited. Furthermore, any two or more of request processor 12, growing facility 13, database 14 and depository 15 may be co-located and/or under the same control.

At step 26, a selection process is performed, preferably according to the selection method of the first aspect.

At step 27, a response is sent to the request. A response may be sent to the requestor 11 and/or to a third party and preferably includes at least one of at least a subset of the results generated at step 26, identification of plant(s), plant(s), identification of microorganism(s), microorganism(s), or plant(s) provided in association with microorganisms, namely those that have been shown to provide benefits at step 26.

At step 28, database 14 may be updated with results of the selection process of step 26. This step may be performed prior to step 27, including periodically or at other various stages which the selection process is conducted. Preferably, at least details of new beneficial associations between plant(s) and microorganisms are recorded. It will be appreciated that incompatible or less beneficial associations will also preferably be recorded, thereby over time building a knowledge framework of plants and microorganisms.

It will be appreciated that one or more of the steps of FIG. 2 may be omitted or repeated. For example, growing facility 13 may generate results at step 26 and in response thereto, one or more of steps 21 to 26 may be repeated.

Thus, the disclosure provides means and methods to improve plant(s) (or growth or other characteristics thereof). This is achieved by enabling a requestor 11 in a first geographical region (e.g. country) or otherwise defined environment (e.g. by parameters or characteristics affecting growing conditions such as such soil salinity or acidity) to access microbiological biodiversity not present or of limited presence in the first region for the purposes of plant improvement in the first or another region. The other region may be or in a foreign country but may be otherwise defined by characteristics of that environment that affect a plant rather than being defined by political boundaries. Consequently, the disclosure may enable a requestor to obtain the beneficial effects of a particular microorganism(s) on a particular plant(s) in a first region, even though such microorganism(s) may not be present or are of limited presence in the first region.

An example implementation of the system embodiment of the disclosure is provided below.

1. A company in say New Zealand (home company), enters into a contractual relationship with a second, say overseas, company (overseas company).
2. The overseas company agrees to send seeds, cuttings or other plant propagules (foreign cultivar) to the home company from plant cultivars adapted to the environment(s) in its own, or other foreign countries, in order to gain access to elements of New Zealand's terrestrial and marine microbial biodiversity that are able to form beneficial plant-microorganism associations with the foreign cultivar.
3. The nature of the benefit may encompass increased plant productivity, for example through any one or more of but not limited to: increased root or foliar mass, or through an increase in efficiency in nutrient utilisation through nitrogen fixation by diazatrophs such as *Klebsiella* or *Rhizobium*, or through release of plant nutrients from the soil, such as phosphates released soil through the production of microbial phytases, or through improvements in plant phenotype for example date of flowering, or changes in physical form e.g. colour, frequency of root or foliar branching, or changes in chemical profile including compounds associated with taste, smell or properties which make the plant suitable for a particular purpose.
4. In New Zealand, the home company identifies which indigenous microorganisms can form an association with the foreign plant by exposing the seed to the microorganisms, with or without knowledge of their likely effects on the plant, by the method of germinating the seed and growing the plant in a growing material that ensures contact of the plant during its growth with indigenous microorganisms via seed coating, direct inoculation into the seed or germinating seedling and/or contamination of the growing medium. The disclosure is not limited to this arrangement or methodology. For example, it may be apparent that microorganisms present in soil other than in New Zealand may provide benefits and testing may be conducted in such regions in addition to or instead of New Zealand. Also, artificial environments may be created. Referring to the immediately prior example, this may be achieved by obtaining soil and/or microorganisms from such regions and conducting the tests in say New Zealand. As will be apparent, such embodiments may include provision for artificial control of climatic conditions among other parameters. Thus, the disclosure is not limited to conducting testing in a region based on its indigenous microorganisms—the microorganisms may be artificially introduced so as to conduct the testing elsewhere than in the microorganisms' natural environment.
5. The period of growth and the physical conditions under which they take place may vary widely according to plant species and specific plant improvement traits, including based on parameters desired or specified by the overseas company. After the relevant period of plant growth the nature of possible plant-microorganisms associations may be determined by microbiological assessment to determine whether microorganisms have formed an endophytic, epiphytic or rhizospheric association with the foreign crop.
6. Where such association(s) are demonstrated the microorganisms form a collection of (say New Zealand indigenous) microorganisms able to associate with the (say foreign) crop or plant.
7. In one embodiment of the disclosure, microbial isolates of the collection may, for example, be coated on to seeds, inoculated into seeds or seedlings, or inoculated into a growing medium that may or may not be sterile.
8. After a suitable period the plants are assessed for improved root and foliar growth or other desired characteristics designed to identify the plant-microorganism associations most able to provide benefit to the plant in the manner desired by the overseas company.
9. Examples of selection criteria are provided herein before, and where identical parameters of the second, overseas environment are not present in the home or test region (i.e., New Zealand in the example), similar parameters most similar to those in the overseas environment and that may be considered acceptable to the overseas company may be selected. As mentioned in 4 above, the disclosure also includes introducing foreign material or creating otherwise artificial conditions in the home or test region.
10. The steps involving growing one or more plant in the presence of one or more microorganism, selecting one or more plants with desired characteristics, and acquiring the microorganism(s) forming an association with the plant will be repeated one or more time.
11. Elite microorganisms providing commercially-significant benefit to the growth of the foreign cultivar are identified by this process and may be shipped to the overseas company for further testing and selection in the foreign environment.
12. In a further embodiment the overseas company will agree that microorganisms found on, or in, the seed, cuttings or propagules of the foreign cultivar will be added to the collection of the home company to enlarge the collection for use both on that cultivar or on other foreign cultivars received for similar testing from other companies.

In an alternative embodiment, the microbial isolates able to form plant-microorganism associations with the foreign cultivar i.e., the collection, are sent to the second company for testing and selection, such that items 7-11 above are performed by and/or in the grounds of the second company. This may be performed by or under the control of the first company.

As a further embodiment, rather than identifying and using predetermined microorganism(s) of a collection, the home company may simply expose the seed to indigenous microorganisms, with or without knowledge of their likely effects on the plant, for example by germinating the seed and growing the plant in a growing material that ensures contact of the plant during its growth with indigenous microorganisms via seed coating, direct inoculation into the seed or germinating seedling and/or contamination of the growing medium or otherwise. As will be apparent, the home company may additionally or alternatively arrange for similar testing in other regions, where the same or different microorganisms may be present. The period of growth and the physical conditions under which they take place may vary widely according to plant species and specific plant traits desired by the overseas company. After a period of plant growth the nature of possible plant-microorganism associations may be determined in a similar manner to that described above.

EXAMPLES

The disclosure is now further described by the following non-limiting examples.

Example 1

Identification of Microorganisms Able to Improve the Sugar Content of Forage Crops Such as Ryegrass Step 1. Untreated ryegrass seeds are planted in a wide variety of soils in small pots. Soils may include additional amendments comprising pure cultures of microorganisms, mixtures of microorganisms or materials containing microorganisms derived from other sources.

Step 2. After a suitable period of growth, say 1 month, the plants are washed out of the soil, and the microorganisms isolated from roots and stems/foliage, either as individual isolates in pure culture, or as mixed populations e.g. as a microbial suspension from an aqueous root crush and/or a stem/foliar crush.

Step 3. The microorganisms are then added to a plant growth medium into which untreated ryegrass seeds are planted. Alternatively, the microorganism(s) are mixed into a suitable seed coating material e.g. a gel, and coated onto seeds before being planted into a similar plant medium. Alternatively, the seeds are geminated and then exposed to the microorganisms for a short period (usually between 1-24 hours to maximise the chance that the microbes may form an endophytic or epiphytic association with the germinating plant) and then planted into a similar growth medium. In each of these cases the growing medium may be initially sterile, although this is not essential.

Step 4. After a period of suitable growth, e.g. 4-6 weeks, foliar growth is assessed and sugar content of crushed foliage determined using a refractometer or other method known to a person skilled in the art. The plants with the highest values for both foliar yield and/or sugar content are selected, and their root and foliar microorganisms isolated and prepared as in Step 2. The process from step 2 to step 3 may then be repeated iteratively, with or without modification of the selection criteria for sugar content relative to foliar yield.

Step 5. After this iterative process has been conducted to the point at which improvement in the sugar content is deemed to be sufficient, the best-performing plants are selected and the microorganisms associated with them are isolated and used to develop a commercial product that improves sugar content of ryegrass.

In an aspect, the product produced from the selected microorganisms is a microbial consortium that is specialized to improve the sugar content of ryegrass. In another aspect, a composition comprising a microbial consortium specialized to improve the sugar content of ryegrass is produced.

Example 2

Identification of Microorganisms Able to Improve the Tittering of Grain Crops Such as Wheat In the case of winter wheat varieties, mainly sown in the Northern Hemisphere, it may be important to select plants that display early tillering after exposure of seed to a growth medium containing microorganisms under conditions of light and temperature similar to those experienced by winter wheat seed in the Northern Hemisphere, since early tillering is a trait related to winter survival, growth, and eventual grain yield in the summer.

Step 1. Untreated wheat seeds are planted in a wide variety of soils or microbial substrates in small pots. Soils may include additional amendments comprising pure cultures of microorganisms, mixtures of microorganisms or materials containing microorganisms that are derived from other sources.

Step 2. After a suitable period of growth period, say 1 month, the plants are washed out of the soil, and the microorganisms isolated from roots and stems/foliage, either as individual isolates in pure culture, or as mixed populations e.g. as a microbial suspension from an aqueous root crush and/or a stem/foliar crush.

Step 3. The microorganisms are then added to a plant growth medium into which untreated wheat seeds are planted. Alternatively, the microorganism(s) are mixed into a suitable seed coating material e.g. a gel, and coated onto seeds before being planted into a similar plant medium. Alternatively, the seeds are geminated and then exposed to the microorganisms for a short period (usually between 1-24 hours to maximise the chance that the microbes may form an endophytic or epiphytic association with the germinating plant) and then planted into a similar growth medium. In each of these cases, the growing medium may be initially sterile, although this is not essential.

Step 4. Tillering is assessed after a suitable period of growth. Plants with the first tillers and/or the greatest number of tillers over a specific time period are selected, and their root and foliar microorganisms isolated and prepared as in Step 2. The process from step 2 to step 3 may then be repeated iteratively, with or without modification of the selection criteria for tillering relative to eventual grain yield.

Step 5. After this iterative process has been conducted to the point at which improvement in tillering is deemed to be sufficient, the best-performing plants are selected and the microorganisms associated with them are isolated and used to develop a commercial product that improves the speed and degree of wheat tillering.

In an aspect, the product produced from the selected microorganisms is a microbial consortium that is specialized to improve the speed and degree of wheat tillering. In another aspect, a composition comprising a microbial consortium specialized to improve the speed and degree of wheat tillering is produced.

Example 3

Use of an Accelerated Microbial Selection Process to Select Seed-Borne Endophytes Conveying a Beneficial Crop Trait Forage grasses expressing beneficial traits such as insect-resistance and improved tolerance to both biotic and abiotic stressors via strains of the seed-borne fungus *Neotyphodium* sp. have been widely adopted by farmers in New Zealand and elsewhere.

It would be desirable to extend the benefits of traits similar to those expressed by this seed-borne fungus and other similar species in the fungal family, to a broader range seed-borne endophytic microbes thereby providing access to a much wider range of beneficial crop traits.

Step 1. Untreated ryegrass seeds are planted in a wide variety of soils in small pots. Soils may include additional amendments comprising pure cultures of microorganisms, mixtures of microorganisms or materials containing microorganisms that derived from other sources.

Step 2. After a suitable period of growth, the plants are washed out of the soil, surface sterilised with a combination of ethanol and sodium hypochlorite or other methods known to people skilled in the art, and the endophytic microorganisms (endophytes) isolated from internal tissues of roots and stems/foliage and seeds, either as individual isolates in pure culture, or as mixed populations e.g. as a microbial suspension from an aqueous root crush and/or a stem/foliar crush.

Step 3. The endophytic microorganisms are then added to a plant growth medium into which pre-germinated surface-sterilised ryegrass seeds are planted (seeds checked for sterility by germinating on nutrient agar plates). Alternatively, the microorganism(s) are mixed into a suitable seed coating material e.g. a gel, and coated onto surface-sterilised seeds before being planted into a similar plant medium. Alternatively, the surface-sterilised seeds are geminated on nutrient agar plates, checked for sterility and then exposed to the microorganisms for a short period (usually between 1-24 hours to maximise the chance that the microbes may form an endophytic or epiphytic association with the germinating plant) and then planted into a similar growth medium. In each of these cases the growing medium may be initially sterile, although this is not essential and further microorganisms may be applied to the growth medium and/or plant.

Step 4). After a period of suitable growth, e.g. 4-6 weeks, plants are assessed for expression of the desired phenotype. Phenotypes may include improved color, plant form, metabolite expression, or the like.

Step 5). Selected plants are permitted to grow onward to the point of seed set. At this stage a subset of seeds from each plant may be screened for endophyte carriage using culture dependent or independent methods. The remaining seeds from plants yielding positive results in the screen are germinated and planted without microbial addition in a further round of selection to enrich for endophyte carriage and the ability to transmit the desired phenotype as described in steps 3-5.

Alternatively, endophytic microbes may be acquired from a subset of seeds from each plant either as isolates from surface sterilised seeds or as explants, or as a microbial suspension prepared, for example, by crushing the surface sterilised seed in aqueous solution. Isolates and preparations are used as an inoculum for plants arising from surface sterilised seeds as described in step 3.

In a further variation of the method, the selection for seed transmission of the trait may take place in the following generation by surface sterilising a subset of seeds (with or without prior screening) from the selected plants of the prior generation and allowing them to germinate and grow on for the period at which point phenotypic screening is conducted as generally described in steps 3 and 4 (i.e. prior to seed set). Plants exhibiting the desired phenotype in this generation (i.e. by seed transmission), are selected and either tissue explants are prepared, and/or microbes isolated from plant tissues, and/or crude microbial suspensions made by crushing the surface foliage or roots in an aqueous solution. One or a combination of these preparations are used as an inoculum for further iterative rounds of growth and selection and seed harvest, as described in steps 3-5. Alternatively, the remaining seeds of plants exhibiting the desired seed-borne trait may be germinated and planted without microbial addition in a further round of selection to enrich for endophyte carriage and the ability to transmit the desired phenotype as described in steps 3-5.

Step 6). At the end of successive rounds of this iterative process, as determined by the generation of a desired seed-borne phenotype, the best seed lines are selected for commercial assessment and cultivar development.

Example 4

Use of an Accelerated Microbial Selection Process to Acquire Microbes Capable of Improving the Growth of Ryegrass (*Lolium perenne*)

Ryegrass is often grown in fertile soil and is an important crop in forage production. It would be desirable therefore to use the process of directed selection to identify a group of microbes that are able to increase the biomass of ryegrass in a fertile substrate without experimentally-imposed selection pressures.

Seventy-three soil samples (treatments) from the North Island of New Zealand were used as a source of microbial diversity for the start of the process. Soil samples were mixed with sand:vermiculite (1:1 or 1:2) as required to increase drainage and volume. Samples were placed in ten replicate 28 ml tubes and planted with ryegrass seeds (*Lolium perenne* cultivar One50, nil endophyte). Seeds were watered with a misting hose until germinated, then showered to saturation three times weekly with additional watering as required to prevent seedlings drying out. For standard growing conditions see Table 1.

TABLE 1

| Standard growing conditions | |
|---|---|
| Variable | Conditions |
| Watering | Three times each week to saturation with water or synthetic fertilizer |
| Temperature | Constant 22-24° C. |
| Daylight period | 16 hr followed by 8 hr darkness |
| Seed sterilization | 15 min in 1-2% sodium hypochlorite followed by 30 min quenching in sodium thiosulphate as described by Miche and Balandreau (2001) |
| Volume of soil/replicate | 28 ml |
| Randomisation | All treatment replicates and controls were spatially randomised |

Round 1 Selection

Sixty days after sowing (DAS) four plants from each sample were selected and processed to provide the microbial inoculum for the first round of selection. Foliage was cut 2 cm above the substrate and discarded. The roots and attached stems were shaken free of soil, washed to remove most soil fragments and drained before the roots and stems were combined in plastic bags. This material was then crushed within the bag with 10 mls of water added to suspend the root material. The liquid portion of the resulting suspension was used as the initial microbial inoculum. Surface-sterilised seeds were soaked for one hour in 1 ml of the root suspension for each sample. Soaked seeds were then planted into 28 ml tubes (15 reps for each treatment) containing potting mix (Kings Plant Barn, New Zealand; granulated bark, peat moss, pumice, and slow-release fertilisers) moistened with tap water. The remaining root suspension was made up to a sufficient final volume with SDW and 2 ml was pipetted over the planted seeds. After planting, the seeds were thinly covered with fresh dry substrate. Pots were subsequently watered with tap water 3 times weekly.

Round 2 Selection

At 118 DAS the foliage was harvested, weighed and treatments selected to provide microbial inoculum for the second round of selection. Only the 8 largest plants from each of the 21 treatments with the greatest mean foliar weight of the original 73 treatments were chosen for processing. In addition four composite treatments of four plants each were created from the sixteen individual plants with the greatest foliar biomass. Foliage was cut 2 cm above substrate level and weighed. The roots and basal stems of each plant were shaken free of substrate then rinsed, combined in plastic bags, crushed and used to inoculate the second round of selection in the same way as described for selection round 1, with the exception that 30 replicates were planted for each treatment and the final volume of inoculum was 65 mls.

Round 3 Selection

Plants from the second round of selection were harvested at 39 DAS. Foliage was cut 2 cm above substrate, weighed and discarded. The three largest plants from the top 15 treatments were selected to create the inoculum for selection round 3. Roots and stems were crushed as described above and used for 30 replicates of each treatment.

Microbial Isolation

Foliage from round 3 selection was harvested and weighed at 63 DAS and the largest plants from the five treatments with the greatest mean foliar weights were selected to provide inoculum for microbial isolations. The roots and 2 cm stems were rinsed and then crushed in plastic bags as described previously. A small volume of the inoculum was drawn off to make a ten-fold dilution series plated on R2A. Pieces of crushed root from each of the preparations were also inoculated into 10 ml N-deficient semi-solid malate (NDSM) medium (Eckford et al, 2002. After 2-4 days incubation at room temperature the resulting pellicles were drawn off and spread onto R2A agar for isolation of individual colonies. A selective isolation step for actinomycetes was performed in which ethanol was added to the root suspension at a final concentration of 25%, incubated at room temperature (RT) for 30 min then plated on R2A. For fungal isolations, pieces of crushed root were embedded in molten PDA (cooled to 45° C.). After 24-72 hr incubation at 25° C. R2A and PDA plates were examined under a dissecting microscope. Bacterial and fungal colonies were assessed for abundance, grouped according to morphology and representative isolates were picked and streaked onto fresh R2A or PDA plates. Standard methods were used to identify isolates to species level by DNA extraction, PCR amplification and sequencing of 16S rRNA genes (bacteria) or ITSS region (fungi).

Microbial Evaluation

Microbial evaluation was performed on 61 individual isolates and 28 consortia chosen on the basis of abundance, diversity, and species characteristics. Selected isolates were spread on R2A (bacteria) or PDA (fungi), incubated at 25° C. for 72 hours then scraped off the agar surface with added SDW into sterile containers. Bacteria were harvested into 2 ml SDW. Fungi were sieved through a sterile tea strainer with 5-10 ml SDW to remove clumps of mycelia and pieces of attached agar. Serial dilutions of the harvested cells were plated and incubated at 25° C. for 24 hours to estimate the number of colony forming units (CFU) in each suspension. Dilution volumes corresponding to $1\times10^7$ (bacteria) and $1\times10^3$ (fungi) CFU per ml were calculated from these plate counts. Ryegrass seeds (One50 nil endophyte) were soaked for one hour in microbe suspensions then individually planted in 28 ml tubes containing moistened potting mix. Two milliliters of isolate suspension was pipetted over the seeds which were then covered with substrate. All plants were subsequently watered with tap water 3 times weekly. Foliage was cut and weighed at 41 DAS. Roots were washed, blotted dry and weighed. The microbial treatments that resulted in plant biomass gains of at least 5% over the microbe-free controls are shown in Table 2.

TABLE 2

Microbial treatments associated with increased ryegrass biomass

| Treatment BDNZ # | % IOC FW | % IOC RW | % IOC BM | ID |
|---|---|---|---|---|
| 58918 | 22.9 | 25.4 | 23.5 | *Microbacterium ginsengiterrae* |
| 58900 | 25.3 | 7.7 | 21.3 | *Bacillus cereus* |
| 58913 | 21.5 | 16.6 | 20.4 | *Microbacterium oxydans* |
| Consortium | 18.9 | 5.1 | 15.8 | *Rhizobium pusense, Curtobacterium ginsengisoli* |
| 59084 | 21.8 | −7.4 | 15.2 | *Penicillium daleae* |
| 58894 | 13.3 | 4.3 | 11.3 | *Brevundimonas vesicularis* |
| 58910 | 13.6 | 2.3 | 11.1 | *Aeromicrobium ponti* |
| 58895 | 11.2 | 5.5 | 9.9 | *Microbacterium hydrocarbonoxydans* |
| 58911 | 8.9 | 5.3 | 8.1 | *Sphingopyxis chilensis* |
| 58950 | 7.8 | 8.4 | 7.9 | *Arthrobacter keyser* |
| 59088 | 13.6 | −14.6 | 7.3 | *Penicillium melinii* |
| 58892 | 8.4 | 0.4 | 6.6 | *Rhizobium grahamii* |
| 58948 | 8.6 | −2.2 | 6.2 | *Brevundimonas vesicularis* |
| Consortium | 5.1 | 9.7 | 6.2 | *Rhizobium pusense, Curtobacterium ginsengisoli, Herbaspirillum rubrisubalbicans* |
| 58891 | 6.7 | −0.2 | 5.1 | *Rhizobium etli* |
| Consortium | 4.9 | 5.6 | 5.0 | *Exiguobacterium indicum, Mesorhizobium amorphae, Brevundimonas vesicularis, Arthrobacter keyser* |

FW = fresh foliar weight; RW = fresh root weight; BM = plant biomass (roots + foliage)
Italics indicate a significant IOC (increase over controls; Fisher's LSD)
ID - Putative identification based on closest sequence match in RDPII and/or NCBI databases The three microbial treatments that resulted in a significant increase in foliar weights (Fisher's LSD) were all isolated from the site that produced the greatest increase in foliar weight in the third selection round.

These results provide evidence that the method for directed selection of microbes, also referred to herein as accelerated microbial selection, described by the present disclosure is capable of identifying a set of microbes that significantly improve the growth of ryegrass grown under favorable conditions.

Furthermore, as indicated by Table 2, the methods are able to identify microbial consortia that significantly improve the growth of ryegrass grown under non-selective conditions.

Example 5

Use of an Accelerated Microbial Selection Process to Identify Microbes Able to Improve the Water-Soluble Carbohydrate Content of Basil (*Ocium basilicum*)

Soil samples from 43 sites in the North Island of New Zealand were used as a source of microbial diversity for this process.

Samples were mixed with sand:vermiculite (1:2) as required to increase drainage and volume. Each sample was used to fill five replicate 28 ml tubes which were planted with 3-5 basil seeds (*Ocium basilicum*, variety Sweet Genovese) per tube. Seedlings were germinated in a plant growth room under conditions described in Table 1. Watering was carried out with tap water as required to prevent wilting.

Approximately 14 DAS the plants were harvested and the foliage cut and discarded. For each sample the basal stems and roots were shaken free of soil, rinsed in sterile distilled water (SDW) and the replicates combined in a plastic bag. The plant material was then crushed thoroughly within the plastic bags. 10 ml SDW was added to the crushed roots and the resulting suspension used as the microbial inoculum for the first selection round.

Basil seeds were soaked for a minimum of one hour in the root extract then planted into 28 ml tubes containing potting mix (40% v/v peat, 30% composted pine bark, 30% fine pumice, adjusted to pH 6.1 with lime) moistened with 6 ml of liquid fertiliser (Miracle-Gro, Scotts Australia Pty Ltd). The remaining root suspension was diluted with 40 ml of SDW and 2 ml was pipetted over the seeds. Ten replicate tubes were prepared for each sample alongside a set of 20 no-microbe controls that were prepared using seeds soaked in sterile distilled water. All tubes were randomised across racks. Seedlings were germinated in a plant growth room under conditions described above. After germination each tube was weeded to leave one randomly selected seedling.

Round 1 Selection

At 20 DAS half of the plants from each treatment were randomly selected for harvest. The remainder of the plants were retained in the growth room for preparation of extracts to inoculate the second round of selection. Plants selected for harvest were removed from the pots, washed to remove adherent potting mix, dried on paper towels and weighed before being placed into a 2 ml tube containing a single stainless steel ball bearing. Samples were then frozen at $-20°$ C. pending analysis for water soluble carbohydrate.

The concentration of water soluble carbohydrate (WSC) in plant extracts was determined using the anthrone method as generally described by Yemm and Willis (Biochem. J. 1954, 57: 508-514). Whole-plant extracts were prepared by bead beating for 2 minutes at 22 hz. One mL of sterile distilled water was then added to each sample. After mixing, 0.5 mL of the liquid suspension was transferred a 96-well microtube block which was placed in a boiling water bath for 30 minutes. Each block was then transferred to a cold water bath for five minutes followed by centrifugation at 3000 rcf for 10 minutes to pellet debris. Supernatants were recovered, diluted 1:25 in SDW, and 40 µL samples transferred to new 96-well microtube blocks. Samples were then overlaid with 200 µL of freshly-prepared anthrone solution (2 mg/mL in 70% sulphuric acid). Blocks were cooled for 5 minutes in an ice-cold water bath, mixed by inversion, placed in a boiling water bath for 60 seconds, then immediately returned to the cold water bath. Once cooled, a 100 µl sample of each reaction was transferred to a flat-bottomed microtitre tray and the absorption measured at 600 nm on a SpectraMax M5e spectrophotometer. Glucose standards were prepared in ultra-pure water and processed as per plant extracts to generate a calibration curve. Results are reported in glucose equivalents (mg) per gram of plant tissue.

Twenty of the 43 treatments yielded a positive increase in median sugar content over the no-microbe control.

Round 2 Selection

The 13 treatments yielding the greatest median sugar content were selected for the second selection round. Microbial extracts were prepared from the remaining 5 plants in each treatment and applied to basil seeds according to the procedure described above with the exception that the number of replicates was increased to 30 for each treatment and 60 for no-microbe controls.

Fifteen days after sowing (DAS) 15 of the plants from each treatment were harvested. The remainder of the plants were retained in the growth room for subsequent isolation experiments. Plants selected for harvest were removed from pots and processed for analysis of water soluble carbohydrate as described previously, with the exception that the anthrone solution was prepared in 80% sulphuric acid to reduce formation of precipitates.

Eight of the 13 treatments yielded a positive increase in median sugar content over the no-microbe control. At this point the rounds of iterative selection were concluded and microbial isolations were performed.

Microbial Isolation

Bacteria and fungi were isolated from up to five of the remaining plants from each of the seven treatments with the greatest median WSC. For each treatment, the roots and lower 1 cm of stem material from each plant were shaken free of substrate and rinsed in sterile distilled water then divided into two portions. One portion was surface sterilized in 6.6% Dettol® (active ingredient: chloroxylenol 4.8%) for 1 minute followed by 3 rinses in SDW for 1 min each. The surface sterilized roots were cut into pieces (about 1-2 cm long) using sterile scissors and dropped into test tube containing NDSM medium (Eckford et al., 2002). After 2-4 days incubation at room temperature the tubes were observed and obvious pellicles drawn off and purified by subculture on R2A agar (Difco).

The roots from one portion were combined in a plastic bag and crushed within the bag with 10 mls of water added to suspend the root material. Pieces of crushed root were retrieved and either placed on PDA plates, or embedded in molten PDA at $45°$ C. Ten-fold serial dilutions of the suspension were prepared in SDW and used to prepare spread plates on R2A agar (Difco). R2A and PDA plates were incubated at $25°$ C. and examined under a dissecting microscope after 24-72 hours incubation. Colonies were assessed for abundance, grouped according to morphology and representative isolates were picked and streaked for purity onto fresh R2A or PDA plates. Standard methods were used to identify isolates to species level by DNA extraction, PCR amplification and sequencing of 16S rDNA (bacteria) or ITSS region (fungi).

Microbial Evaluation

Two rounds of microbial evaluation were performed on isolates selected on the basis of abundance, diversity, and species characteristics. In the first evaluation round, 80 treatments were tested comprising 68 individual isolates and 12 consortia.

Selected bacterial and fungal isolates were cultured on R2A and PDA plates respectively and suspensions prepared in SDW for inoculation of seeds as generally described in example 4.

The suspensions were diluted to $1 \times 10^7$ (bacteria) and $1 \times 10^3$ (fungi) per ml for use as individual treatments. Consortia were prepared using equal volumes of each individual microbial suspension. Basil seeds were soaked for one hour in microbial suspensions then planted into 28 ml tubes containing commercial potting mix (described in example 4) that had been moistened with 6 ml of tap water. Two ml of microbial suspension was pipetted over the top of each seed. Thirty replicates were prepared for each treatment and 45 replicates were prepared for the no-microbe control.

Thirteen DAS 15 plants from each treatment and 22 no-microbe controls were selected for harvest and WSC determination. Sample preparation was performed as described previously with the exception that after bead beating, 0.8 ml of SDW was added to each tube and a second round of bead beating was performed. A 0.5 mL sample of the resulting mixed suspension was then transferred to a 96-well microtube dilution block and stored at −20° C. Blocks were thawed and assayed for carbohydrate as previously described.

A total of 36 microbial treatments yielded median carbohydrate concentrations greater than microbe-free controls. This data was used to generate a refined set of 44 treatments comprising 34 individual isolates and 10 consortia for a second round of microbial evaluation. Treatments were selected on the basis of results for increased WSC and included individual isolates that performed well in consortia, as well as new consortia prepared from highly ranked microbes.

Microbial treatments were prepared and the basil seed was soaked and planted as described above with the exception that the number of treatment replicates was increased to 45 and no-microbe controls increased to 90.

All plants were harvested 14 days after sowing and processed for WSC analysis as described above, with the exception that blocks were frozen overnight after the first 30 minute heating step. Samples were then thawed and processed as previously described. A dilution series of a single basil sample was loaded onto all blocks to serve as an internal control and enable normalisation of between-block variation.

A total of 20 microbial treatments yielded median WSC concentrations greater than microbe-free controls with 11 treatments yielding greater than 5% increases over the control (IOC; Table 3).

The treatment yielding the highest median carbohydrate concentration was a new microbial consortium of the three top-ranking individual isolates from the first round of microbial evaluation.

TABLE 3

Microbial treatments yielding carbohydrate concentrations greater than microbe-free controls in round 2 microbial evaluation.

| Treatment BDNZ # | ID | % IOC |
|---|---|---|
| 60706, 60784, 61090 | Sphingomonas mali, Flavobacterium micromati, Penicillium sp. | 14.0 |
| 60695, 60696, 60697, 60698, 60699, 60700 | Sphingobium chlorophenolicum, Massilia niastensis, Flavobacterium limicola, Rhizobium alamii, Sphingopyxis sp., Pelomonas aquatica | 12.4 |
| 60587 | Azospirillum lipoferum | 11.4 |
| 60732, 60739, 60740, 60744, 61082 | Mesorhizobium amorphae, Asticcacaulis taihuensis, Ralstonia solanacearum, Microbacterium foliorum, Trichoderma | 10.6 |
| 60805 | Burkholderia megapolitana | 10.2 |
| 60732 | Mesorhizobium amorphae | 7.9 |
| 61043 | Umbelopsis sp | 7.5 |
| 60734 | Aquabacterium fontiphilum | 7.2 |
| 60797 | Rhodanobacter terrae | 7.1 |
| 60706 | Sphingomonas mali | 7.1 |
| 60578, 60580, 60696, 60697, 61043 | Sphingobium xenophagum, Pseudomonas moraviensis, Massilia niastensis, Flavobacterium limicola, Umbelopsis sp. | 5.0 |
| No-microbe control | | 0.0 |

ID - putative identification based on closest match in NCBI and/or RDPII databases These results provide evidence that the method for directed selection of microbes, also referred to herein as accelerated microbial selection, described by the present disclosure is capable of producing a set of microbes that improve the production of water soluble carbohydrate in basil.

Furthermore, as indicated by Table 3, the methods are able to identify microbial consortia that significantly improve the concentration of water soluble carbohydrate in basil.

Example 6

Identification of Endophytic Microbes that Improve the Growth of Maize (Zea mays)

Endophytic microbes are closely associated with or contained within plant tissues, therefore may be less exposed to competition and stressors than microbes associated with the plant rhizosphere. It would be desirable to create a group of endophytic microbes that are capable of promoting maize growth by means such as increasing plant biomass or grain yield. In this example an endophytic microbe is defined as one that is still viable after surface sterilisation of maize plant tissues with 6.6% Dettol® (active ingredient: chloroxylenol 4.8%) for 1 minute.

Seventy-three soil samples from the North Island of New Zealand were used as the source of microbial diversity. Soil samples (treatments) were mixed with sterile sand:vermiculite (1:1 or 1:2) as required to increase drainage and volume. The resulting mixtures were placed in 28 ml tubes and planted with 15 replicates of maize (Pioneer Zea mays hybrid seeds 37Y12) in each treatment. Seedlings were watered with a misting hose until germinated, then showered to saturation three times weekly with additional watering as required. For remaining standard growing conditions see Table 1.

Three plants from each treatment were selected at 60 days after sowing (DAS). The stems of the maize plants were cut 5 cm above the soil and discarded. The roots and attached stems were shaken free of soil, washed to remove soil fragments and drained before the roots and stems were combined in plastic bags. This material was then crushed within the bag with 10 ml of water added to suspend the root material. The liquid portion of the resulting suspension was used as the microbial inoculum for a non-selective enrichment round. The purpose of this extra round was to increase the abundance of microbes growing within maize tissues. Surface-sterilised maize (37Y12) seeds were soaked for one hour in 1 ml of the root suspension for each sample. Soaked seeds were then planted into 28 ml tubes (15 reps for each treatment) containing sterile sand and vermiculite 1:2 moistened with 6 ml Phostrogen® soluble plant food (diluted 1/450 v/v in sterile distilled water). The remaining root suspension was made up to a final volume of 40 ml using sterile distilled water (SDW) and 2 ml was pipetted over the planted seeds.

Round 1 Selection

Sixty days after sowing (DAS) the five largest plants in each treatment were selected and processed to provide the microbial inoculum for the first round of selection. The foliage of each of the selected plants was cut 5 cm above substrate level and discarded. The remaining basal stem and roots were washed thoroughly in tap water to remove any adherent soil and then combined within treatments in plastic bags before being surface sterilised with 6.6% Dettol® for 1 minute to select for endophytic microbes. Roots were then rinsed 3 times in SDW for 1, 5 then 10 minutes with agitation. Rinsed roots were crushed within the plastic bags as described above, and suspended in a final volume of 20 ml SDW. The resulting suspension was used to inoculate 15 surface-sterilised maize seeds (Pioneer Zea mays P9400) by soaking them for one hour in 10 ml of the inoculum before they were planted into sterile sand:vermiculite 1:3 moistened with sterile synthetic fertiliser (Fahraeus, 1957). The remaining suspension was made up to a final volume of 40 ml for each treatment and 2 ml was pipetted over the top of each planted seed. Thirty replicate tubes of microbe-free control seeds were soaked in SDW and pipetted with 2 mls of water per tube in a duplicate process free of microbial inoculum. After planting the seeds were covered with fresh dry substrate. Pots were watered with SDW for the first week after planting to maintain sterile conditions, then with tap water three times weekly.

Round 2 Selection

Plants were harvested at 26 DAS. Foliage was cut and weighed as described above. The remaining basal stem and roots of each plant were rinsed clean, blotted dry with fresh paper towels then weighed and bagged individually. The inoculum for the second round of selection was prepared from the 20 treatments yielding the greatest mean biomass and the five largest individual plants from all treatments. The roots and basal stems of the 10 largest plants from each selected treatment were pooled, surface sterilised and crushed as described above. The five largest individual plants were processed individually as above. Thirty replicates (Pioneer P9400 seeds) were planted for each of the 25 treatments in sterile sand:vermiculite 1:3 moistened with sterile synthetic fertiliser.

Round 3 Selection

Plants were harvested at 26 DAS and processed as described previously. The six largest plants from the 7 treatments yielding the greatest mean biomass were selected to create the inoculum for the third round of selection. Plants were grown for 28 days, harvested and assessed as described for previous rounds. The roots and basal stems of the three largest plants from the top three treatments were pooled, and the two largest plants in the experiment were selected individually to provide inoculum for microbial isolation.

Microbial Isolation

Microbial isolations were performed on root suspensions used to inoculate the R3 selection and on the suspensions prepared from the R3 plants selected above. Bacterial and fungal isolations were performed as generally described above using R2A, PDA and NDSM media. A selective isolation step for actinomycetes was performed in which ethanol was added to the root suspension at a final concentration of 25%, incubated at RT for 30 min then plated on R2A. Plates were examined after 1-7 days incubation at 25° C. Colonies were assessed for abundance, grouped according to morphology and representative isolates were picked and subcultured on to R2A. Standard methods were used to identify isolates to species level by DNA extraction, PCR amplification and sequencing of 16S rRNA gene (bacteria) or ITSS regions (fungi).

Microbial Evaluation Rounds

Two rounds of microbial evaluation were performed. In the first evaluation round 79 strains were selected based on abundance, diversity and species characteristics. Bacterial isolates were prepared and used to inoculate surface-sterilised seeds as described in example 4, with the exception that maize seeds (P9400) were used. Fungal strains were plated on PDA, incubated at 25° C. for 7 days then scraped off plates with 5-10 ml SDW and sieved through a tea strainer to remove clumps of mycelia and pieces of attached agar. The number of spores/hyphae was determined using a Neubauer improved haemocytometer and compound microscope and a dilution series of $5\times10^2$, $1\times10^3$ and $2\times10^3$ was prepared. Each dilution was then pipetted over 10 planted seeds thereby totalling 30 seeds per replicate each at 3 dose levels. For both fungi and bacteria, surface-sterilised maize seeds (Pioneer P9400) were planted in 28 ml tubes containing sterile potting mix (40% peat, 30% composted pine bark, 30% fine pumice, adjusted to pH 6.1 with lime) moistened with Fahraeus solution (Fahraeus, 1957) before being covered with fresh dry substrate. All plants were subsequently watered with tap water 3 times weekly.

Plants were harvested 24 DAS and both foliage and roots were weighed. Microbial isolates yielding an average increase in foliar and/or root weight over microbe-free controls were selected for a second round of evaluation. The chosen strains were processed and planted as described above, with the exception that seeds were soaked and inoculated with fungal strains at a concentration of $1\times10^3$ rather than three dilutions and 15 replicates were planted for all strains. Foliage and roots were harvested and weighed at 20 DAS. The results are shown in Table 4. Four of the isolates resulted in significantly higher biomass than the microbe-free controls.

TABLE 4

Endophytic microbes producing increased maize biomass

| BDNZ # | Count | % IOC FW | % IOC RW | % IOC BM | ID |
|---|---|---|---|---|---|
| 57119 | 12 | *13.1* | 9.9 | 11.8 | Herbaspirillum frisingense |
| 57583 | 14 | *14.3* | 5.1 | 10.6 | Acinetobacter sp. |
| 57122 | 15 | 9.6 | 12.2 | 10.6 | Xanthomonas translucens |
| 57115 | 14 | *14.4* | 3.9 | 10.2 | Pseudomonas marginalis |
| 57535 | 12 | *10.7* | 8.9 | 10.0 | Herbiconiux ginsengi |
| 57148 | 12 | 10.0 | 9.8 | 9.9 | Burkholderia cepacia |
| 57531 | 14 | 6.4 | *14.7* | 9.7 | Microbacterium oxydans |
| 57150 | 14 | *11.8* | 6.1 | 9.5 | Pseudomonas moraviensis |
| 57597 | 15 | 9.5 | 8.6 | 9.1 | Azotobacter chroococcum |
| 57155 | 14 | 7.8 | 10.6 | 8.9 | Pseudomonas frederiksbergensis |
| 57154 | 15 | 6.6 | 8.4 | 7.3 | Sphingomonas rosa |
| 57602 | 14 | 6.2 | 8.6 | 7.2 | Rhizobium endophyticum |
| 57619 | 15 | 8.5 | 4.8 | 7.0 | Bacillus thioparans |
| 57127 | 15 | 4.0 | 11.0 | 6.8 | Terriglobus roseus |
| 57612 | 15 | 8.2 | 3.9 | 6.5 | Novosphingobium rosa |
| 58016 | 14 | 4.7 | 8.6 | 6.2 | Azospirillum lipoferum |
| 57565 | 12 | 5.6 | 5.1 | 5.4 | Streptomyces thermocarboxydus |
| 57613 | 15 | 7.3 | 1.6 | 5.0 | Herbaspirillum frisingense |

Italics indicate a significant difference from microbe free control (Fisher's LSD); % IOC, percentage increase over controls
Putative ID based on closest match in RDPII database to partial 16S rRNA sequence These results provide evidence that the method for directed selection of microbes, also referred to herein as accelerated microbial selection, described by the present disclosure is capable of producing a set of endophytic microbes that improve the growth of maize.

Furthermore, the microbes provided in Table 4 can be utilized to identify microbial consortia that are capable of improving the growth of maize.

The disclosure has been described herein, with reference to certain embodiments, in order to enable the reader to practice the disclosure without undue experimentation. However, a person having ordinary skill in the art will readily recognise that many of the components and parameters may be varied or modified to a certain extent or substituted for known equivalents without departing from the scope of the disclosure. It should be appreciated that such modifications and equivalents are herein incorporated as if individually set forth. In addition, titles, headings, or the like are provided to enhance the reader's comprehension of this document, and should not be read as limiting the scope of the present disclosure.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

BIBLIOGRAPHY

Pikovskaya R I (1948). Mobilization of phosphorus in soil connection with the vital activity of some microbial species. *Microbiologia* 17:362-370, incorporated by reference herein.

Miche, L and Balandreau, J (2001). Effects of rice seed surface sterilisation with hypochlorite on inoculated *Burkholderia vietamiensis. Appl. Environ. Microbiol.* 67(7): p 3046-3052, incorporated by reference herein.

Fahraeus, G. (1957). *J. Gen Microbiol.* 16: 374-381, incorporated by reference herein.

Ruth Eckford, R., Cook, F. D., Saul, D., Aislabie J., and J. Foght (2002) Free-living Heterotrophic Bacteria Isolated from Fuel-Contaminated Antarctic Soils. *Appl. Environ. Microbiol* 68(10):5181. Yemm and Willis (Biochem. J. 1954, 57: 508-514), incorporated by reference herein.

Colby, R. S., "Calculating Synergistic and Antagonistic Responses of Herbicide Combinations, 1967 Weeds, vol. 15, pp. 20-22, incorporated by reference herein.

PCT/NZ2012/000041, filed Mar. 16, 2012, (WO2012/125050A1), incorporated by reference herein.

What is claimed is:

1. An iterative plant phenotypic trait based screening method for selecting one or more microorganisms capable of imparting a beneficial phenotypic trait to a cereal plant, comprising:
   a) growing a plurality of cereal plants in a growth medium, in the presence of a first set of one or more microorganisms;
   b) selecting at least one cereal plant from said plurality, following step a), based upon a beneficial phenotypic trait exhibited by the cereal plant relative to other cereal plants of said plurality;
   c) acquiring a second set of one or more microorganisms from the at least one cereal plant selected in step b), or rhizosphere surrounding the at least one cereal plant selected in step b);
   d) repeating steps a) to c) one or more times, wherein the second set of one or more microorganisms acquired in step c) is used as the first set of one or more microorganisms in step a) of any successive repeat; and
   e) selecting one or more microorganisms that is associated with imparting a beneficial phenotypic trait to a cereal plant.

2. The method according to claim 1, wherein the selecting one or more microorganisms of step e) comprises: isolating one or more microorganisms associated with imparting a beneficial phenotypic trait to a cereal plant.

3. The method according to claim 1, wherein the selecting one or more microorganisms of step e) comprises: utilizing a molecular technique to characterize the one or more microorganisms associated with imparting a beneficial phenotypic trait to a cereal plant.

4. The method according to claim 1, wherein at least two microorganisms associated with imparting a beneficial phenotypic trait to a cereal plant are selected in step e).

5. The method according to claim 1, wherein the cereal plant is a member of the Poaceae family.

6. The method according to claim 1, wherein the cereal plant is selected from the genus: *Zea, Sorghum, Panicum, Oryza, Triticum, Hordeum, Secale, Triticale*, or *Avena*.

7. The method according to claim 1, wherein the cereal plant is *Zea mays*.

8. The method according to claim 1, wherein the cereal plant is *Oryza sativa*.

9. The method according to claim 1, wherein the cereal plant is *Oryza sativa indica* or *Oryza sativa japonica*.

10. The method according to claim 1, wherein the cereal plant is a *Triticum* spp.

11. The method according to claim 1, wherein the second set of one or more microorganisms are acquired from the at least one cereal plant in step c).

12. The method according to claim 1, wherein the second set of one or more microorganisms are acquired from a root, stem, and/or foliar tissue from the at least one cereal plant in step c).

13. The method according to claim 1, wherein the second set of one or more microorganisms are acquired from the rhizosphere in step c).

14. The method according to claim 1, wherein the at least one cereal plant selected in step b) exhibits a superior beneficial phenotypic trait, relative to other cereal plants of said plurality, selected from the group consisting of: growth rate, height, weight, production of metabolite, production of protein, production of carbohydrate, production of oil, leaf size, stem size, general health, survivability, speed of seed germination, quantity of biomass produced, root growth, leaf growth, shoot growth, grain yield, fibre yield, oil yield, seed yield, and combinations thereof.

15. The method according to claim 1, wherein said first set of one or more microorganisms in step a) are obtained by a microbial capture step, comprising: growing a plurality of cereal plants in a growth medium, in the presence of one or more microorganisms, and acquiring said first set of one or more microorganisms from the plurality of cereal plants, or growth medium surrounding the plurality of cereal plants.

16. The method according to claim 1, wherein said first set of one or more microorganisms in step a) are obtained by a microbial capture step, comprising: growing a plurality of cereal plants in a natural soil, in the presence of one or more microorganisms existing in the natural soil, and acquiring said first set of one or more microorganisms from the plurality of cereal plants, or growth medium surrounding the plurality of cereal plants.

17. The method according to claim 1, wherein said first set of one or more microorganisms in step a) are obtained from a pre-existing microbial collection, database, library, or depository.

18. An iterative plant phenotypic trait based screening method for selecting one or more microorganisms capable of imparting a beneficial phenotypic trait to a plant, comprising:
   a) growing a plurality of plants in a growth medium, in the presence of a first set of one or more microorganisms;
   b) selecting at least one plant from said plurality, following step a), based upon a beneficial phenotypic trait exhibited by the plant relative to other plants of said plurality;
   c) acquiring a second set of one or more microorganisms from stem and/or foliar tissue of the at least one plant selected in step b);

d) repeating steps a) to c) one or more times, wherein the second set of one or more microorganisms acquired in step c) is used as the first set of one or more microorganisms in step a) of any successive repeat; and e) selecting one or more microorganisms that is associated with imparting a beneficial phenotypic trait to a plant.

19. The method according to claim 18, wherein the selecting one or more microorganisms of step e) comprises: isolating one or more microorganisms associated with imparting a beneficial phenotypic trait to a plant.

20. The method according to claim 18, wherein the plant is a member of the Poaceae family.

21. The method according to claim 18, wherein the plant is selected from the genus: *Zea, Sorghum, Panicum, Oryza, Triticum, Hordeum, Secale, Triticale,* or *Avena*.

22. The method according to claim 18, wherein the at least one plant selected in step b) exhibits a superior beneficial phenotypic trait, relative to other plants of said plurality, selected from the group consisting of: growth rate, height, weight, production of metabolite, production of protein, production of carbohydrate, production of oil, leaf size, stem size, general health, survivability, speed of seed germination, quantity of biomass produced, root growth, leaf growth, shoot growth, grain yield, fibre yield, oil yield, seed yield, and combinations thereof.

23. The method according to claim 18, wherein said first set of one or more microorganisms in step a) are obtained by a microbial capture step, comprising: growing a plurality of plants in a growth medium, in the presence of one or more microorganisms, and acquiring said first set of one or more microorganisms from the plurality of plants, or growth medium surrounding the plurality of plants.

24. The method according to claim 18, wherein said first set of one or more microorganisms in step a) are obtained by a microbial capture step, comprising: growing a plurality of plants in a natural soil, in the presence of one or more microorganisms existing in the natural soil, and acquiring said first set of one or more microorganisms from the plurality of plants, or growth medium surrounding the plurality of plants.

25. The method according to claim 18, wherein said first set of one or more microorganisms in step a) are obtained from a pre-existing microbial collection, database, library, or depository.

26. An iterative plant phenotypic trait based screening method for selecting one or more microorganisms capable of imparting a beneficial phenotypic trait to a plant, comprising:

a) growing a plurality of plants in a growth medium, in the presence of a first set of one or more microorganisms;

b) selecting at least one plant from said plurality, following step a), based upon an above-ground beneficial phenotypic trait exhibited by the plant relative to other plants of said plurality;

c) acquiring a second set of one or more microorganisms from the at least one plant selected in step b), or rhizosphere surrounding the at least one plant selected in step b);

d) repeating steps a) to c) one or more times, wherein the second set of one or more microorganisms acquired in step c) is used as the first set of one or more microorganisms in step a) of any successive repeat; and e) selecting one or more microorganisms that is associated with imparting a beneficial phenotypic trait to a plant.

27. The method according to claim 26, wherein the plant is a member of the Poaceae family.

28. The method according to claim 26, wherein the at least one plant selected in step b) exhibits a superior above-ground beneficial phenotypic trait, relative to other plants of said plurality, selected from the group consisting of: above-ground growth rate, height, leaf size, stem size, general health, survivability, quantity of above-ground biomass produced, leaf growth, shoot growth, grain yield, fibre yield, seed yield, and combinations thereof.

29. An iterative plant phenotypic trait based screening method for selecting one or more microorganisms capable of imparting a beneficial phenotypic trait to a plant, comprising:

a) growing a plurality of plants in a growth medium, in the presence of a first set of one or more microorganisms;

b) selecting at least one plant from said plurality, following step a), based upon a beneficial phenotypic trait exhibited by the plant relative to other plants of said plurality;

c) acquiring a second set of one or more microorganisms from the at least one plant selected in step b), or rhizosphere surrounding the at least one plant selected in step b), wherein said second set of one or more microorganisms are not acquired from a root nodule;

d) repeating steps a) to c) one or more times, wherein the second set of one or more microorganisms acquired in step c) is used as the first set of one or more microorganisms in step a) of any successive repeat; and e) selecting one or more microorganisms that is associated with imparting a beneficial phenotypic trait to a plant.

30. The method according to claim 29, wherein the plant is a member of the Poaceae family.

* * * * *